US 6,596,539 B1

(12) United States Patent
Stemmer et al.

(10) Patent No.: US 6,596,539 B1
(45) Date of Patent: *Jul. 22, 2003

(54) MODIFICATION OF VIRUS TROPISM AND HOST RANGE BY VIRAL GENOME SHUFFLING

(75) Inventors: Willem P. C. Stemmer, Los Altos, CA (US); Phillip Patten, Menlo Park, CA (US); Nay Wei Soong, Sunnyvale, CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/183,037

(22) Filed: Oct. 30, 1998

Related U.S. Application Data

(63) Continuation-in-part of application No. 08/962,236, filed on Oct. 31, 1997, now abandoned.

(51) Int. Cl.[7] ............................................. C12N 15/00
(52) U.S. Cl. ............................. 435/440; 435/5; 435/6; 435/455; 435/456; 435/457
(58) Field of Search .................... 435/5, 6, 440–455, 435/456, 457

(56) References Cited

U.S. PATENT DOCUMENTS

| | | |
|---|---|---|
| 5,264,563 A | 11/1993 | Huse |
| 5,470,725 A | 11/1995 | Borriss et al. |
| 5,523,388 A | 6/1996 | Huse |
| 5,593,972 A | 1/1997 | Weiner et al. |
| 5,605,793 A | 2/1997 | Stemmer |
| 5,698,426 A | 12/1997 | Huse |
| 5,723,323 A | 3/1998 | Kauffman et al. |
| 5,763,192 A | 6/1998 | Kauffman et al. |
| 5,770,434 A | 6/1998 | Huse |
| 5,808,022 A | 9/1998 | Huse |
| 5,811,238 A * | 9/1998 | Stemmer et al. ............... 435/6 |
| 5,814,476 A | 9/1998 | Kauffman et al. |
| 5,817,483 A | 10/1998 | Kauffman et al. |
| 5,824,469 A | 10/1998 | Horwitz et al. |
| 5,824,514 A | 10/1998 | Kauffman et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,862,514 A | 1/1999 | Huse et al. |
| 5,866,363 A | 2/1999 | Pieczenik |
| 5,871,974 A | 2/1999 | Huse |
| 5,928,905 A | 7/1999 | Stemmer et al. |
| 5,939,250 A | 8/1999 | Short |
| 5,955,358 A | 9/1999 | Huse |
| 5,958,672 A | 9/1999 | Short |
| 5,965,408 A | 10/1999 | Short |
| 5,976,862 A | 11/1999 | Kauffman et al. |

(List continued on next page.)

FOREIGN PATENT DOCUMENTS

| | | |
|---|---|---|
| EP | 0 229 046 | 5/1994 |
| EP | 544 809 B1 | 12/1998 |
| EP | 563 296 B1 | 3/1999 |
| WO | WO 86/05803 | 10/1986 |

(List continued on next page.)

OTHER PUBLICATIONS

Stemmer, W.P., "Rapid evolution of a protein in vitro by DNA shuffling [see comments].", NATURE, (Aug. 4, 1994) 370(6488):389–91.*

(List continued on next page.)

*Primary Examiner*—Laurie Scheiner
*Assistant Examiner*—J. S. Parkin
(74) *Attorney, Agent, or Firm*—Margaret A. Powers; Norman J. Kruse; Townsend and Townsend and Crew, LLP

(57) ABSTRACT

The invention relates to a method and compositions for modifying a phenotype of a virus, such as viral tropism and host range, by iterative sequence recombination of variant viruses and selection of improved variants.

16 Claims, 9 Drawing Sheets

U.S. PATENT DOCUMENTS

| | | | |
|---|---|---|---|
| 5,989,553 A | | 11/1999 | Johnston et al. |
| 6,001,574 A | | 12/1999 | Short et al. |
| 6,004,788 A | | 12/1999 | Short |
| 6,030,779 A | | 2/2000 | Short |
| 6,054,267 A | | 4/2000 | Short |
| 6,057,103 A | | 5/2000 | Short |
| 6,096,548 A | * | 8/2000 | Stemmer .................... 435/440 |
| 6,117,679 A | * | 9/2000 | Stemmer .................... 435/440 |
| 6,132,970 A | | 10/2000 | Stemmer |

FOREIGN PATENT DOCUMENTS

| | | |
|---|---|---|
| WO | WO 90/14424 | 11/1990 |
| WO | WO 90/14443 | 11/1990 |
| WO | WO 92/03461 | 3/1992 |
| WO | WO 92/06176 | 4/1992 |
| WO | WO 92/06204 | 4/1992 |
| WO | WO 92/11272 | 7/1992 |
| WO | WO 94/11496 | 5/1994 |
| WO | WO 95/22625 | 8/1995 |
| WO | WO 96/31613 | 10/1996 |
| WO | WO 96/33207 | 10/1996 |
| WO | WO 97/20078 | 6/1997 |
| WO | WO 97/35957 | 10/1997 |
| WO | WO 97/35966 | 10/1997 |
| WO | WO 98/13485 | 4/1998 |
| WO | WO 98/13487 | 4/1998 |
| WO | WO 98/27230 | 6/1998 |
| WO | WO 98/31816 | 7/1998 |
| WO | WO 98/31837 | 7/1998 |
| WO | WO 99/06834 | 2/1999 |
| WO | WO 99/19506 | 4/1999 |
| WO | WO 99/21979 | 5/1999 |
| WO | WO 99/23107 | 5/1999 |
| WO | WO 99/29902 | 6/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/65927 | 12/1999 |
| WO | WO 00/04190 | 2/2000 |
| WO | WO 00/06718 | 2/2000 |
| WO | WO 00/09727 | 2/2000 |
| WO | WO 00/18778 | 4/2000 |
| WO | WO 00/18906 | 5/2000 |

OTHER PUBLICATIONS

Stemmer, W.P., "DNA shuffling by random fragmentation and reassembly: in vitro recombination for molecular evolution.", Proceedings Of The National Academy Of Sciences Of The United States Of America, (Oct. 25, 1994) 91(22):10747–51.*

Zhang, J.H., et al.,"Directed evolution of a fucosidase from a galactosidase by DNA shuffling and screening.", Proceedings Of The National Academy Of Sciences Of The United States Of America, (Apr. 29, 1997) 94(9):4504–9.*

Conley, A.J., et al., "Neutralization of primary human immunodeficiency virus type 1 isolates by the broadly reactive anti–V3 monoclonal antibody, 447–52D.", Journal Of Virology (Nov. 1994) 68(11):6994–7000.*

Affholter, Joseph and Stemmer, Willem P. G.; *Directed Evolution of Proteins and Pathways by DNA Shuffling, Book of Abstracts, 216th ACS National Meeting,* Boston, Aug. 23–27, 1998, BIOT–042.

Howard, Russell J.; *Chemistry of the future: Exploitation of the Power of Biology, Book of Abstracts, 216th ACS National Meeting,* Boston, Aug. 23–27, 1998, BTEC–045.

Juha Punnonen, *Evolution of DNA Vaccine Vectors by Gene Shuffling, The First Gordon Research Conference on Genetic Vaccines/DNA Vaccines,* Plymouth State College, Plymouth, NH, Jul. 20–25, 1997.

J. Punnonen et al., *Evolution of Genetic Vaccines by DNA Shuffling, Abstract #227, Molecular Aspects of Viral Immunity, Keystone Symposium on Molecular and Cellular Biology,* Tamarron, Colorado, Feb. 16–22, 1998.

Soong, Nay–Wei; Patten, Phillip A. and Stemmer, Willem PC; *Directed Evolution of Novel Retroviral Tropisms by DNA Shuffling, Abstract, Retroviruses, 1998 Meeting,* May 26–31, 1998, Cold Spring Harbor Laboratory, Cold Spring Harbor, New York.

Soong, Nay–Wei, Nomura, Laurel and Stemmer, Willem PC; *DNA Shuffling as a Tool to Evolve Desired Retroviral Phenotypes, Abstract, p. 228, Gene Therapy, 1998 Meeting,* Sep. 23–27, 1998, Cold Spring Harbor Laboratory, Cold Spring Harbor, New York.

Soong, Nay–Wei, Patten, Phillip A. and Stemmer, Willem PC; *Directed Evolution of Novel Retroviral Tropisms by DNA Shuffling, Abstract #97, Programs & Abstracts, 1st Annual Meeting of the American Society of Gene Therapy,* May 28–31, 1998, Seattle, Washington.

Stemmer, Willem P. C., *Directed Evolution of Proteins, Pathways, Episomes and Viruses by DNA Shuffling, FASEB Journal 12(8): A1303, Meeting of the American Society for Biochemistry and Molecular Biology,* Washington, D.C., U.S.A., May 16–20, 1998.

Stemmer, W. P. C.; Crameri, A. and Minshull, J.; *Molecular Evolution of Genes and Pathways by DNA Shuffling, FASEB Journal 11(9): A1124, 17th International Congress of Biochemistry and Molecular Biology in conjunction with the Annual Meeting of the American Society for Biochemistry and Molecular Biology,* San Francisco, CA, USA, Aug. 24–29, 1997.

Stemmer, Willem P. C., *DNA Sequence Evolution by Sexual PCR, Experientia (Basel) 52(ABSTR): A25, 28th Annual Meeting of the Swiss Societies for Experimental Biology (USGEB/USSBE),* Zuerich–Irchel, Switzerland, Mar. 27–29, 1996.

Chang et al., "Evolution of a cytokine using DNA family shuffling," *Nature Biotech.*, 17:793–797 (1999).

Christians et al., "Directed evolution of thymidine kinase for AZT phosphorylation using DNA family shuffling," *Nature Biotechnology,* 17:259–264 (1999).

Crameri et al., "Molecular Evolution Of An Arsenate Detoxification Pathway By DNA Shuffling", *Nat. Biotechnol.,* 15(5):436–438 (1997).

Crameri et al., "DNA Shuffling Of A Family Of Genes From Diverse Species Accelerates Directed Evolution", *Nature,* 391(3664):288–291 (1998).

Crameri et al., "Improved Green Fluorescent Protein By Molecular Evolution Using DNA Shuffling", *Nat. Biotechnol.,* 14(3):315–319 (1996).

Crameri et al., "Construction And Evolution Of Antibody–Phage Libraries By DNA Shuffling", *Nat. Med.,* 2(1):100–102 (1996).

Crameri et al., "Combinatorial Multiple Cassette Mutagenesis Creates All The Permutations Of Mutant And WildType Sequences", *Biotechniques,* 18(2):194–196 (1995).

Gates et al., "Affinity Selective Isolation Of Ligands From Peptide Libraries Through Display On A Lac Repressor 'Headpiece Dimer'", *J. Mol. Biol.,* 255(3):373–386 (1996).

Minshull et al., "Protein evolution by molecular breeding," *Curr. Opin. Chem. Biol.,* 3:284–290 (1999).

Ness et al., "DNA shuffling of subgenomic sequences of subtilisin," *Nature Biotech.,* 17:893–896 (1999).

Stemmer, "DNA Shuffling by Random Fragmentation and Reassembly: In Vitro Recombination for Molecular Evolution" *Proc. Natl. Acad. Sci. USA*, 91(22):10747–10751 (1994).

Stemmer, "Searching Sequence Space", *Biotechnology*, 13:549–553 (1995).

Stemmer, "The Evolution of Molecular Computation", *Science*, 270(5241):1510 (1995).

Stemmer, "Sexual PCR and Assembly PCR" *Encyclopedia Mol. Biol.*, VCH Publishers, New York, pp. 447–457 (1996).

Stemmer et al., "Single–Step Assembly Of A Gene And Entire Plasmid From Large Numbers Of Oligodeoxyribonucleotides", *Gene*, 164(1):49–53 (1995).

Stemmer et al., "Molecular breeding of viruses for targeting and other clinical properties," *Tumor Targeting*, 4:59–62 (1999).

Zhang et al., "Directed Evolution Of A Fucosidase From A Galactosidase By DNA Shuffling And Screening", *Proc. Natl. Acad. Sci. USA*, 94(9):4504–4509 (1997).

Adey, et al., "Preparation of Second–Generation Phage Libraries," In: *Phage Disp. Pept. Proteins by Academic Press, Inc.*, Chapter 16:277–291 (1996).

Crameri, et al., "$10^{20}$–Fold Aptamer Library Amplification Without Gel Purification," *Nucleic Acids Research* 21(18):4410 (1993).

Stemmer, et al., "Selection of an Active Single Chain Fv Antibody from a Protein Linker Library Prepared by Enzymatic Inverse PCR," *Biotechniques* 14(2):256–265 (1993).

Stemmer, et al., "Increased Antibody Expression from *Escherichia coli* Through Wobble–Base Library Mutagenesis by Enzymatic Inverse PCR," *Gene* 123(1):1–7 (1993).

Stemmer, et al., "Enzymatic Inverse PCR: A Restriction Site Independent, Single–Fragment Method for High–Efficiency, Site–Directed Mutagenesis," *Biotechniques* 13(2):214–220 (1992).

Stemmer, et al., "Expression of Antibody Fv Fragments Specific for a Heavy Metal Chelate (Indium–EDTA) in *E. coli*," Meeting of the Keystone Symposia on Molecular and Cellular Biology, Keystone, Colorado, USA, Apr. 8–14, 1991, *J. Cell Biochem Suppl* 0 (15 Part G), 217 (1991).

Stemmer, et al., "A 20–Minute Ethidium Bromide/HighSalt Extraction Protocol for Plasmid DNA," *BioTechiques* 10(6):726 (1991).

Conley, A. J., et al. *Neutralization of Primary Human Immunodeficiency Virus Type 1 Isolates by the Broadly Reactive Anti–V3 Monoclonal Antibody, 447–52D, Journal of Virology*, Nov. 1994, vol. 68, No. 11 pages 6994–7000.

Forte, P., et al., *Human CD4 produced in lymphoid cells of transgenic mice binds HIV gp120 and modifies the subsets of mouse T–cell populations, Immunogenetics*, 1993, vol. 38, pp. 455–459.

Harouse, J. M., et al., *Infection of SK–N–MC Cells, a CD4–Negative Neuroblastoma Cell Line, with Primary Human Immunodeficiency Virus Type 1 Isolates, Journal of Virology*, Oct. 1996, vol. 70, No. 10, pp. 7290–7294.

He, J., et al., *CCR3 and CCR5 are co–receptors for HIV–1, infection of microglia, Nature*, Feb. 13, 1997, vol. 385, pp. 645–649.

Joag, S. V., et al., *Chimeric Simian/Human Immunodeficiency Virus That Causes Progressive Loss of CD4$^+$ T Cells and AIDS in Pig–Tailed Macaques, Journal of Virology*, May, 1996, vol. 70, No. 5, pp. 3189–3197.

Law, Y. M., et al., *Human CD4 Restores Normal T Cell Development and Function in Mice Deficient in Murine CD4, J. Exp. Med*, Apr. 1994, vol. 179, pp. 1233–1242.

Maassab, H. F. and DeBorde, D.C., *Characterization of an Influenza A Host Range Mutant, Virology*, 1983, vol. 130, pp. 342–350.

Aldrovandi et al., "Replication and Pathogenicity of Human Immunodeficiency Virus Type 1 Accessory Gene Mutants in SCID–hu Mice," *J. Virology* 70(3):1505–1511 (Mar. 1996).

Asjo et al., "Replicative Capacity of Human Immunodeficiency Virus From Patients with Varying Severity of HIV Infection," *The Lancet* pp. 660–662 (Sep. 20, 1986).

Bonyhadi et al., "The SCID–hu Mouse: an in vivo model for HIV–1 infection in humans," *Mol. Med. Today* pp. 246–253 (Jun. 1997).

Cheng–Mayer et al., "Biologic Features of HIV–1 That Correlate with Virulence in the Host," *Science* 240:80–82 (Apr. 1, 1988).

Fenyo et al., "Distinct Replicative and Cytopathic Characteristics of Human Immunodeficiency Virus Isolates," *J. Virology* 62(11):4414–4419 (Nov. 1988).

Gao et al., "Molecular Cloning and Analysis of Functional Envelope Genes from Human Immunodeficiency Virus Type 1 Sequence Subtypes A through G," *J. Virology* 70(3):1651–1667 (Mar. 1996).

Kamel–Reid et al., "Engraftment of Immune–Deficient Mice with Human Hematopoietic Stem Cells," *Science* 242:1706–1709 (Dec. 23, 1988).

Klotman et al., "Transgenic models of HIV–1," *AIDS* 9(4):313–324 (1995).

Lewis et al., "Developing animal models for AIDS research—progress and problems," *TIBTECH* 13:142–150 (Apr. 1995).

McCune et al., "The SCID–hu Mouse: Murine Model for the Analysis of Human Hematolymphoid Differentiation and Function," *Science* 241:1632–1639 (Sep. 23, 1988).

McCune et al., "Suppression of HIV Infection in AZT-Treated SCID–hu Mice," *Science* 247:564–566 (Feb. 2, 1990).

Morrow et al., "Small animals Are Not Susceptible to Human Immunodeficiency Virus Infection," *J. Gen. Virol.* 68:2253–2257 (1987).

Mosier et al., "Rapid Loss of CD4+ T Cells in Human–P-BL–SCID Mice by Noncytopathic HIV Isolates," *Science* 260:689–692 (Apr. 30, 1993).

Mosier et al., "Human Immunodeficiency Virus Infection of Human–PBL–SCID Mice," *Science* 251:791–794 (Feb. 15, 1991).

Mosier et al., "Transfer of a functional human immune system to mice with severe combined immunodeficiency," *Nature* 335: 256–259 (Sep. 15, 1988).

Mosier, "Modeling AIDS in a Mouse," *Hospital Practice* 31(9):41–60 (Sep. 15, 1996).

Robertson et al., "Recombination in HIV–1," *Nature* 374:124–126 (Mar. 9, 1995).

Ruprecht et al., "Development of Antiviral Treatment Strategies in Murine Models," *Aids Res. Human Retroviruses* 8(6):997–1011 (1992).

Temin, "Retrovirus variation and evolution," *Genome* 31:17–22 (1989).

Tersmette et al., "Evidence for a Role of Virulent Human Immunodeficiency Virus (HIV) Variants in the Pathogenesis of Acquired Immunodeficiency Syndrome: Studies on Sequential HIV Isolates," *J. Virology* 63(5):2118–2125 (May 1989).

* cited by examiner

```
                    ┌─────────────────────┐
                    │ STARTING (PARENTAL) │
                    │   VIRAL GEROME(S)   │
                    └─────────────────────┘
              (1)              ▲              (2)
        ┌──────────────────────┴──────────────────────┐
              EITHER PATH (1) OR (2), OR BOTH
```

```
        ▼                                              ▼
┌──────────────────┐  ITERATIVE      ITERATIVE  ┌──────────────────┐
│   SELECT FOR     │  RECYCLE        RECYCLE    │ SHUFFLE GENOME   │
│  REPLICATION IN  │ ┌── ─ ─ ─    ─ ─ ─ ──┐    │    SEQUENCES     │
│ NON-HUMAN CELLS  │ │                     │    │                  │
└──────────────────┘ │                     │    └──────────────────┘
        │            │                     │            │
        ▼            │                     │            ▼
┌──────────────────┐ │                     │   ┌──────────────────────┐
│ SHUFFLE GENOME   │ │                     │   │   SELECT SHUFFLED    │
│  SEQUENCES OF    │ │                     └── │GENOMES FOR REPLICATION│
│ SELECTED GENOMES │ │                         │  IN NON-HUMAN CELLS  │
└──────────────────┘                           └──────────────────────┘
```

Figure shows flowchart with "OBTAIN SELECTED SHUFFLED VARIANT GENOMES CAPABLE OF REPLICATION IN NON-HUMAN CELLS" leading to TRANSGENIC NON-HUMAN ANIMAL (E.G., MOUSE), then "INFECT NON-HUMAN ANIMAL WITH INFECTIOUS SELECTED SHUFFLED VIRUS", then "RECOVER REPLICATED SHUFFLED VIRAL GENOME(S)", with ITERATIVE RECYCLE loops.

FIG. 3.

(A)
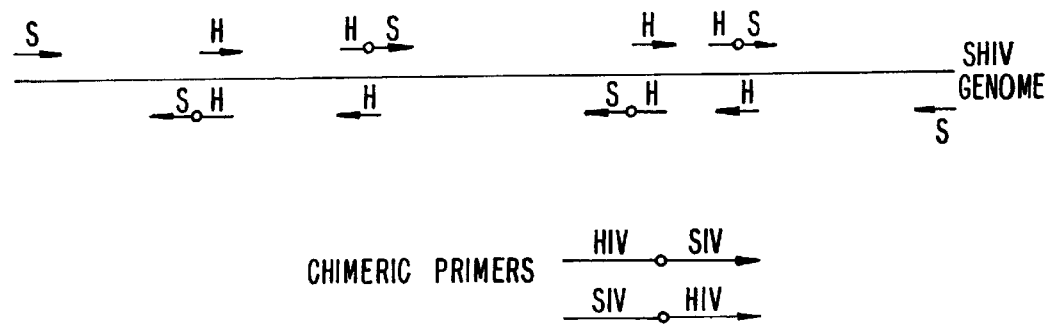
(B)
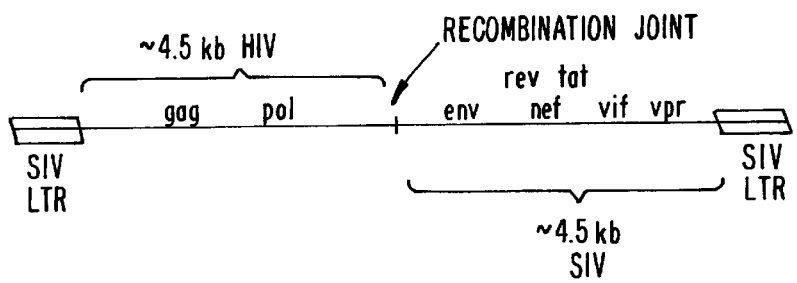
FIG. 4.

MODIFICATION OF VIRUS TROPISM AND HOST RANGE BY VIRAL GENOME SHUFFLING

CROSS-REFERENCES TO RELATED APPLICATIONS

This application is a continuation-in-part of 08/962,236 filed Oct. 31, 1997 now abandoned. The present application claims benefit of the 08/962,236 application, which is incorporated herein by reference in its entirety for all purposes.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to methods and compositions for forced evolution of a virus genome, such as a genome of an HIV-1 virus strain, to produce a variant virus having an altered phenotype that provides a desired property that may be advantageous for development of small animal models of viral diseases, and for the development of novel therapeutic approaches to viral diseases, among others (e.g., evolving a virus to replicate in an advantageous tissue culture system). The invention relates to novel viral genomes and virions which are capable of replication in non-human animals and cells, and further relates to transgenic non-human animals and cell lines capable of supporting replication of such evolved virus variants. The invention also relates to methods for identifying novel antiviral agents.

BACKGROUND OF THE INVENTION

HIV-1 and AIDS

Human immunodeficiency virus type I (HIV-1) is a human retrovirus that is believed to be an etiologic agent of acquired immune deficiency syndrome (AIDS), an infectious disease characterized by a profound loss of immune system function. An aspect of HIV-1 disease is the typically delayed onset of disease symptoms, such as opportunistic infections, Kaposi's sarcoma, dementia, and wasting syndrome. Often it may take 10 to 15 years after initial infection before symptoms are evident; however, in some instances disease onset is quite rapid. Moreover, the specific pathology of HIV-1 disease can be quite variable between individuals and between strains of the HIV-1 virus (for a review, see Field's Virology, Third Edition, Fields et al. Eds., Lippincott-Raven Publishers, Vol. 2, Chapters 60 and 61). At present, HIV-1 appears to be almost always pathogenic in humans, and although certain chemotherapeutic agents (e.g., protease inhibitors, nucleoside analogs) have shown clinical promise in arresting or slowing HIV-1 disease, there is no established cure or preventative for HIV-1 disease at present.

Unfortunately, the HIV-1 virus is also characterized by an extraordinarily high frequency of mutational change, including deletions, base pair substitutions, insertions, and recombinations between HIV-1 genomes. It has been estimated that on the average at least one quarter of the progeny virus from a single cycle of retrovirus replication will have some kind of mutation relative to the parent genome, and recombination will further recombine these variant genomes (Temin H M (1989) Genome 31: 17). This characteristic of HIV-1 (and other lentiviruses, such as retroviruses) makes it difficult to obtain therapeutic solutions which the virus cannot escape due to its inherently high rate of mutation and propensity to generate variants which are resistant to the particular therapeutic solution selected. For this reason, the currently used therapeutic method to treat HIV-1 disease is to combine a cocktail of multiple chemotherapeutic agents (e.g., protease inhibitors and nucleoside analogs) to make it less likely that a resistant variant can arise during therapy. Nonetheless, it is almost certain that resistant HIV-1 variants will arise, particularly in view of imperfect patient compliance with chemotherapeutic regimens, pharmacogenetic differences between individuals in bioavailability of the chemotherapy agents, and use of partially degraded or inaccurately dispensed chemotherapy agents in less-advanced nations.

The globally circulating strains of HIV-1 exhibit extreme genetic diversity (Robertson et al. (1995) Nature 374: 124). To evaluate the extent of global HIV-1 variation, sequences of virus strains originating from numerous countries have been compared. These studies have shown that HIV-1 can be classified into two major groups, designated M and O, which are defined as distinct clusters on phylogenetic trees. Groups M comprises the great majority of HIV-1 isolates and can be further subdivided into at least nine sequence subtypes or clades, designated A to I, with additional variants being added to the classification scheme continually (Gao et al. (1996) J. Virol. 70: 1651). Given this degree of diversity, it is widely believed that a vaccine based on a single strain or subtype of HIV-1 will be unsuccessful against the larger spectrum of globally circulating HIV-1 variants, as well as against new variants which continually arise. Furthermore, the HIV-1 virus appears to undergo sequence variation and functional mutation in patients; isolates from different phases of HIV-1 infection exhibit stage-specific replication characteristics (Asjo et al. (1986) Lancet 2: 660; Cheng-Meyer et al. (1988) Science 240: 80; Fenyo et al. (1988) J. Virol. 62: 4414; Tersmette (1989) J. Virol. 63: 2118).

In view of the propensity of HIV-1 to undergo rapid mutation and generate variants that are resistant to chemotherapeutic agents and candidate "universal" vaccines, it is desirable to have non-human animal models of HV-1 replication and disease in order to speed the identification an d development of new generations of antiviral agents that can be used to treat resistant HIV-1 variants, or to prevent the generation of such variants in vivo. Unfortunately, such non-human models of HIV-1 disease are presently lacking.

Non-human Models of HIV-1 Disease

The absence of a suitable animal model has remained one of the major barriers to the development of an effective therapy for HIV-1 infection. Ideally, a readily available small animal model that could sustain HIV-1 infection and develop clinical symptoms that reflect the disease in humans would prove useful for modeling pathogenesis and developing new antiviral agents. An animal model that could duplicate human immune responses would greatly facilitate the development of vaccines. Unfortunately, no current model fulfills these varied needs (for review see, Klotman et al. (1995) AIDS 9: 313; Chang et al. (1996) Transfus. Sci. 17: 89; and Bonyhadi M L and Kaneshima H (June, 1997) Molec. Med. Today pp. 246–253; Mosier D E (September, 1996) Hosp. Prac. Pp. 41–60).

In general, non-human animals are not susceptible to infection with HIV-1 (Morrow et al. (1987) J. Gen. Virol. 68: 2253). However, several animal models exist in which to study retroviruses related to HIV-1 and their related pathology; these include SIV in macaque monkeys, FIV in cats, and murine acquired immunodeficiency syndrome virus (MAIDS) in mice, among others. HIV-1 replicates weakly in chimpanzees, but causes no detectable disease symptoms, and chimpanzees are quite expensive and not suited for large-scale studies. Lewis A D and Johnson P R (1995) TIBTECH 13: 142 discuss various non-human animal model systems and their limitations.

Several HIV-2 isolates, including three molecular clones of HIV-2 (HIV-2ROD, HIV-2SBL-ISY, and HIV-2UC1), have also been reported to infect macaques (*M. mulatta* and *M. nemestrina*) or baboons (Franchini, et al. (1989) Proc. Natl. Acad. Sci. U.S.A. 86, 2433–2437; Barnett, et al. (1993) Journal of Virology 67, 1006–14; Boeri, et al. (1992) Journal of Virology 66, 4546–50; Castro, et al. (1991) Virology 184, 219–26; Franchini, et al. (1990) Journal of Virology 64, 4462–7; Putkonen, et al. (1990) Aids 4, 783–9; Putkonen, et al. (1991) Nature 352, 436–8).

As alternatives to the above, models of HIV-1 pathogenesis have been experimentally derived in mice that are transgenic for portions of the HIV genome or an entire HIV-1 genome, as well as in SCID mice which have been reconstituted with HIV-infected immune cells (Ramezani et al. (1996) Transfus. Sci. 17: 99; Chang et al. (1996) op.cit). HIV transgenic mice have been developed to model the in vivo regulation and pathological consequences of expression of various HIV open reading frames (ORFs), including known HIV structural genes; although some useful information might have been obtained from expression in various tissues of such animals, HIV gene expression in T cells of HIV transgenic mice has been negligible, indicating a substantial limitation of these mice as HIV disease models. Furthermore, a major hindrance of any mouse system is the inability of HIV to infect mouse cells, even when these are transduced with the gene for human CD4, the major receptor protein for HIV-1 infectivity.

SCID/hu mice have been reported as candidate animal models for studying HIV-1 (Mosier D E (1996) op.cit; Aldrovandi G M and Zack J A (1996) J. Virol. 70: 1505; Bonyhadi M L and Kaneshima H (1997) op.cit). SCID mice lack mature mouse T and B cells, and have been successfully engrafted with human hematolymphoid organs (e.g., the SCID/hu mouse having engrafted human thymus and liver tissue, peripheral blood leukocytes (PBLs), or hematopoietic precursor cells (Kamel-Reid et al. (1988) Science 242: 1706; McCune et al. (1988) Science 241: 1632; Mosier et al. Nature 335: 256). Such xenochimeric SCID/hu or SCID/hu-PBL mice have been used to study HIV pathogenesis in vivo and to evaluate anti-HIV drugs (Mosier et al. (1991) Science 251: 791; Mosier et al. (1995) Science 260: 689; McCune et al. (1990) Science 247; 564; Ruprecht et al. (1992) AIDS Res. Hum. Retroviruses 8: 997). However, these SCID mice models produced certain results which were anomalous, such as when infected with non-cytopathic macrophage-tropic (in humans) HIV isolates the mice underwent a rapid depletion of CD4+ cells, but when infected with cytopathic, T cell-tropic HIV isolates the CD4+ cells were not depleted, the exact opposite of what occurs in the human.

Thus, the art continues to search for improved models of HIV disease using small animal models and different (i.e., non-HIV) viruses. The absence of a suitable animal model has remained one of the major barriers to the development of an effective therapy for HIV-1 infection. It is apparent from the foregoing that a need exists in the art for an improved model of HIV-1 infection to further the development of anti-HIV therapies and prophylactic agents.

Significant improvements to and new opportunities for anti-HIV therapies and antiviral screening methods could be realized if better models of HIV-1 replication and pathogenesis were available. The present invention meets these and other needs and provides such improvements and opportunities.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference, whether specifically noted as such or not.

SUMMARY OF THE INVENTION

The present invention relates to methods for generating viral genotypes encoding at least one modified viral tropic phenotype, such as infectivity, virulence, and pathogenesis in a cell type, tissue, or host animal species (commonly host range; defined herein as a subset of viral tropism). The tropic phenotype modification can either permit or restrict viral infection, replication, and/or cytopathic effect in a predetermined cell type and/or host species (e.g., a non-human mammal). A basic format of the method, termed viral genome shuffling, in broad application, consists of: (1) contacting a cell strain, cell line, or non-human animal (or explanted organ therefrom), which does not naturally support substantial replication of an predetermined virus, with at least one initial infectious virion or replicable genome of said predetermined virus under replication conditions, (2) recovering a plurality of replicated genome copies of said predetermined virus, either as virions or as viral genomes in polynucleotide form, wherein some or all of the replicated genome copies comprise a mutation relative to the initial infectious virion or replicable genome, (3) recombining a plurality of said replicated genome copies, so as to shuffle the mutations, thereby generating a collection of recombined replicated genome copies, and (4) selecting or screening said collection of recombined replicated genome copies to obtain one or more replicable viral genome encoding at least one modified viral tropic phenotype. It is often desirable to perform at least one additional iterative cycle whereby the collection of recombined replicated genome copies is contacted with the cell strain, cell line, or non-human animal (or explanted organ therefrom) under replication conditions to produce second (or subsequent) round replicated copies having additional mutations, and to recover and shuffle, by recombination, said second (or subsequent) round replicated genome copies prior to the step of selecting or screening for genomes encoding a modified viral tropic phenotype. Typically, the recombination in step (3) is performed in vitro or by an in vivo recombination method which substantially does not occur naturally during replication of said viral genome. In certain variations, naturally occurring in vivo recombination mechanisms can be used in conjunction with a collection of preselected virus variants having a desired phenotypic property to be optimized further; in this way, a natural viral recombination mechanism can be combined with intelligent selection of variants in an iterative manner to produce optimized variants by "forced evolution", wherein the forced evolved virus variants are not expected to, nor are observed to, occur in nature, nor are predicted to occur at an appreciable frequency. The practitioner may further elect to supplement and/or the mutational drift by introducing mutated viral genomes, or portions thereof, into the pool of initial infectious virions (or replicable genomes) and/or into the plurality of replicated genome copies which are recombined. Mutational drift may also be supplemented by the use of mutagens (e.g., chemical mutagens or mutagenic irradiation), or by employing replication conditions which enhance the mutation rate of the virus.

The invention also provides for the viral genomes and infectious virions produced by the method of viral genome shuffling; the exact structures of said produced viral genomes and infectious virions are definable a priori only by reference to the method by which they are generated. Thus, the invention includes a viral genome, or plurality thereof, produced by the methods described herein. The shuffled viral genome(s) produced thereby are easily distinguishable from naturally occurring viral genomes by virtue of their atypical modified viral tropic phenotype(s) which is/are normally not present in the population of naturally occurring viral genomes.

In a variation of the basic method, one or more portions of the viral genome are separately optimized or improved for function in the predetermined cell type and/or host species as distinct genetic elements isolated from the remainder of the viral genome. The optimized or improved portions of the viral genome are then either introduced into the initial viral genome(s) for use in the method, or are shuffled in by recombination with the replicated genome copies recovered after a round of replication in the host cell or host animal. In a variation, the optimized or improved portions of the viral genome can be used in conjunction with one or more heterologous polynucleotide sequence(s), such as non-viral genes or replicons to confer a desired functional or structural property, such as transcriptional regulation or translational regulation, to the heterologous sequence(s). Optimized or improved portions of a virus genome often can be marketed as a commercial product, either alone or in combination with one or more heterologous sequences.

The invention also encompasses compositions of such shuffled viral genomes encoding at least one modified viral tropic phenotype. The compositions can include a plurality of species of shuffled viral genomes, or can represent a single purified viral genome species. Certain shuffled viral genomes encode variant viruses which possess detectable phenotypes that are not naturally occurring and which can be selected for; selected phenotypes often are characterized by desirable properties, such as modified host range as compared to wildtype virus, modified cell tropism as compared to wildtype virus, and modified immunogenicity, among other desirable properties.

The invention also encompasses screening assays and kits comprising a composition of such shuffled viral genome(s) and a cell type, tissue, or host animal species for which said shuffled viral genome(s) encode a modified viral tropism or drug resistance phenotype. In an aspect, the screening assay or kit further comprises a test agent, which is typically a small organic molecule such as a nucleoside analog or protease inhibitor with a molecular weight of less than 3,000 Daltons. In an aspect, the cell type or host animal is transgenic and expresses at least one human protein which confers, either alone or in conjunction with one or more additional human protein species, susceptibility of a cell to infection by and/or replication of said predetermined virus.

The invention provides screening assay methods for identifying and quantitating pharmacological properties of antiviral compounds. An exemplary screening assay format to identify agents that modify replication of a virus, said method comprises the steps of: (1) contacting, under suitable conditions, a test agent with a screening composition comprising: (i) one or more variants of said virus evolved by viral genome shuffling so as to replicate in cells or in a non-human animal, which cells or non-human animal does not naturally support replication of said virus, and (ii) said cells or non-human animal, and (2) determining whether said test agent modifies replication of said variant(s) in said cells or non-human animal. In an embodiment, the test agent inhibits virus replication, although it should be possible to screen for test agents which modify other aspects of viral replication, such as replication potentiators, immune modulators (for use with non-human animal systems), and agents which modify the virus genetic expression program (e.g, late gene inhibitors, latency modifiers, and the like).

Although the methods of the invention are believed to be suitable for use with substantially any virus type, including plant viruses, bacterial viruses, and animal viruses, it is described with particular reference to HIV-1 for illustrative purposes. It is believed that, with regard to animal viruses, the method will find particular use in developing shuffled virus genomes of pathogenic or oncogenic viruses for which present-day non-human animal models are insufficient or lacking entirely. HIV-1 and the related HIV disease is only one example of such suitable viruses and their pathologies.

With reference to HIV-1, the invention provides a method for producing, by viral genome shuffling, at least one HIV-1 variant which is capable of substantial replication in a non-human cell type. In an embodiment, the invention provides a method for generating one or more HIV-1 genome(s) which encode(s) the phenotype of permissive replication in mouse cells that express at least one human protein which confers, either alone or in conjunction with one or more additional human protein species, susceptibility of a mouse cell to infection by and/or replication of HIV-1. Examples of such human susceptibility proteins for HIV-1 infection include, but are not limited to hCD4, hCCR5. hCXCR4, and other accessory proteins identified in the art. Often, non-human primate homologs of these proteins can be substituted. In an aspect, the method employs a transgenic non-human cell or animal containing at least one expression cassette which encodes and expresses at least one human HIV-1 susceptibility protein. The viral genome shuffling method using these transgenic cells and/or animals as replication media produces shuffled HIV variants which have improved tropism for infection and/or replication of the transgenic non-human cells or animals. The shuffled HIV variants may be backcrossed (e.g., by recombination) to one or more HIV isolate(s), with concomitant selection for retention of the property of improved tropism for the transgenic cells or animals, thereby retaining the minimal mutations necessary for the desired tropic phenotype while "nativizing" the remainder of the viral genome to conform with the chosen HIV isolate(s). By the use of backcrossing, it is believed possible to generate, by use of the method of the invention, HIV variants substantially corresponding to essentially any HIV clinical isolate or sequence-related category thereof (e.g., group, clade, etc.), wherein the variants possess a desired phenotypic property not naturally associated with HIV; an example of such a phenotypic property can be the capacity for substantial replication in non-human cells and non-human organisms, such as for example mouse cells and transgenic mice.

In an aspect, the methods of the invention can be used to modify the immunogenic properties of a virus (i.e., the phenotype being selected for is an immunological property). For example, a virus (or collection of virus species) can be evolved to evade a host organism immune system, such as a human or mouse immune system. Also for example, a virus (or collection of virus species) can be evolved so as to mimic one or more immunologic stages of virus evolution in vivo; e.g., the viral dynamics of HIV-1 infection of a human patient is characterized by a continual natural evolution of certain immunodominant viral epitopes so as to naturally evade the human immune system—the present invention can be used to generate HIV-1 variants which mimic one or more later immunological stages of HIV infection; such variants may serve as candidate HIV-1 vaccines, among other uses.

In an aspect, the methods of the invention can be used to modify the metabolic properties of a virus (i.e., the phenotype being selected for is a resistance to one or more chemotherapeutic agent). For example, a virus (or collection of virus species) can be evolved to rapidly model the natural development of drug resistance to anti-HIV drugs. The present invention can be used to generate HIV-1 variants which are drug resistant; such variants can be used in screening assays to identify alternative chemotherapeutic agents to which the HIV variants are not cross-resistant, among other uses.

The disclosed method for altering a viral phenotype by iterative genome shuffling and phenotype selection is a pioneering method which enables a broad range of novel and advantageous viral and non-viral compositions, therapeutic and prophylactic methods and compositions, and apparatus which will be apparent to those skilled in the art in view of the present disclosure.

Other features and advantages of the invention will be apparent from the following description of the drawings, preferred embodiments of the invention, the examples, and the claims.

BRIEF DESCRIPTION OF THE FIGURES

FIG. 3. Schematic portrayal of virus evolution by viral genome shuffling to produce variants capable of substantial replication in a non-human animal, such as a mouse.

FIG. 4. (A) Schematic portrayal of how chimeric oligonucleotide primers can be used to generate a SHIV genome by PCR-based shuffling of a mixture of an HIV genome and a SIV genome using the chimeric primers. An "H" indicates a portion complementary to an HIV sequence and a "S" indicates a portion complementary to a SIV sequence. (B) Structural diagram of SIV/HIV chimeric genome for shuffling and propagation in monkey cells.

DEFINITIONS

Figure 1:
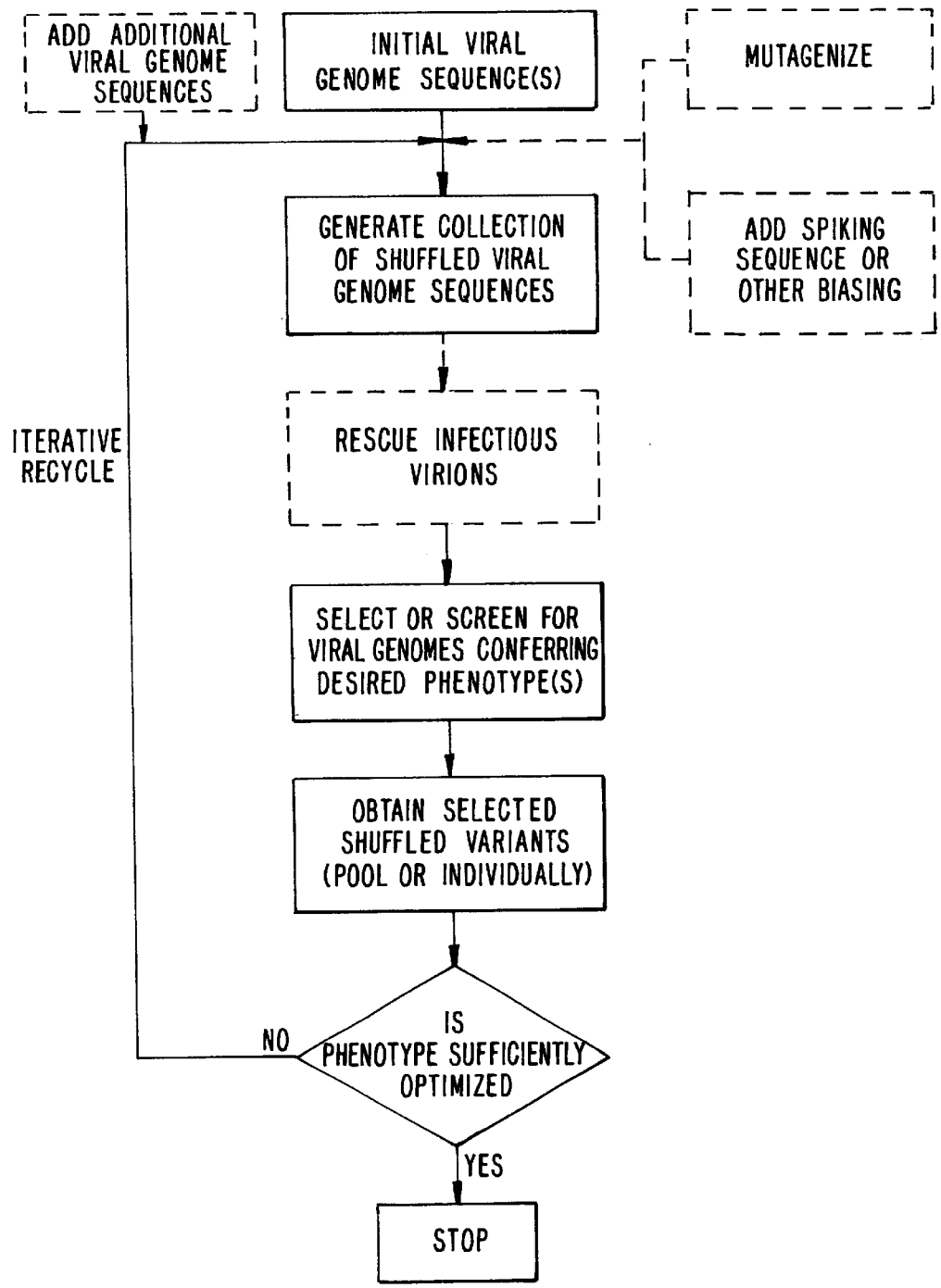
FIG. 1. Block diagram of an embodiment of the basic method for viral genome shuffling and selection for a desired phenotype. Solid boxes and arrows indicate principal steps, outlined boxes and dotted arrows indicate alternative or optional steps or iterations.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "reassembly" is used when recombination occurs between identical polynucleotide sequences.

By contrast, the term "shuffling" is used herein to indicate recombination between substantially homologous but non-identical polynucleotide sequences, in some embodiments DNA shuffling may involve crossover via nonhomologous recombination, such as via cre/lox and/or flp/frt systems and the like, such that recombination need not require substantially homologous polynucleotide sequences. Homologous and non-homologous recombination formats can be used, and, in some embodiments, can generate molecular chimeras and/or molecular hybrids of substantially dissimilar sequences. Viral recombination systems, such as template-switching and the like can also be used to generate molecular chimeras and recombined viral genomes, or portions thereof.

The term "related polynucleotides" means that regions or areas of the polynucleotides are identical and regions or areas of the polynucleotides are heterologous.

The term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

The term "cleaving" means digesting the polynucleotide with enzymes or breaking the polynucleotide (e.g., by chemical or physical means), or generating partial length copies of a parent sequence(s) via partial PCR extension, PCR stuttering, differential fragment amplification, or other means of producing partial length copies of one or more parental sequences.

The term "population" as used herein means a collection of components such as polynucleotides, nucleic acid fragments or proteins. A "mixed population" means a collection of components which belong to the same family of nucleic acids or proteins (i.e. are related) but which differ in their sequence (i.e. are not identical) and hence in their biological activity.

The term "mutations" means changes in the sequence of a parent nucleic acid sequence (e.g., a gene or a viral genome) or changes in the sequence of a parent polypeptide. Such mutations may be point mutations such as transitions or transversions. The mutations may be deletions, insertions or duplications.

The term "recursive sequence recombination" as used herein refers to a method whereby a population of polynucleotide sequences are recombined with each other by any suitable recombination means (e.g., sexual PCR, homologous recombination, site-specific recombination, etc.) to generate a library of sequence-recombined species which is then screened or subjected to selection to obtain those sequence-recombined species having a desired property; the selected species are then subjected to at least one additional cycle of recombination with themselves and/or with other polynucleotide species and at subsequent selection or screening for the desired property.

The term "amplification" means that the number of copies of a nucleic acid fragment is increased.

The term "naturally-occurring" as used herein as applied to an object refers to the fact that an object can be found in nature. For example, a polypeptide or polynucleotide sequence that is present in an organism (including viruses) that can be isolated from a source in nature (e.g., including from human patients) and which has not been intentionally modified by man in the laboratory is naturally-occurring. As used herein, laboratory strains of rodents which may have been selectively bred according to classical genetics are considered naturally-occurring animals. As used herein, naturally-occurring viruses are those viruses, including natural variants thereof, which can be found in a source in nature, including virally infected individuals.

As used herein "predetermined" means that the cell type, non-human animal, or virus may be selected at the discretion of the practitioner on the basis of a known phenotype.

As used herein, "linked" means in polynucleotide linkage (i.e., phosphodiester linkage). "Unlinked" means not linked to another polynucleotide sequence; hence, two sequences are unlinked if each sequence has a free 5' terminus and a free 3' terminus.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. A structural gene (e.g., a HSV tk gene) which is operably linked to a polynucleotide sequence corresponding to a transcriptional regulatory sequence of an endogenous gene is generally expressed in substantially the same temporal and cell type-specific pattern as is the naturally-occurring gene.

As used herein, the terms "expression cassette" refers to a polynucleotide comprising a promoter sequence and, optionally, an enhancer and/or silencer element(s), operably linked to a structural sequence, such as a cDNA sequence or genomic DNA sequence. In some embodiments, an expression cassette may also include polyadenylation site sequences to ensure polyadenylation of transcripts. When an expression cassette is transferred into a suitable host cell, the structural sequence is transcribed from the expression cassette promoter, and a translatable message is generated, either directly or following appropriate RNA splicing. Typically, an expression cassette comprises: (1) a promoter, such as an SV40 early region promoter, HSV tk promoter or phosphoglycerate kinase (pgk) promoter, or other suitable promoter known in the art, (2) a cloned polynucleotide sequence, such as a cDNA or genomic fragment ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, pCD and γNMT (Okayama H and Berg P (1983) Mol. Cell. Biol. 3: 280; Okayama H and Berg P (1985) Mol. Cell. Biol. 5: 1136, incorporated herein by reference).

The term "transcriptional modulation" is used herein to refer to the capacity to either enhance transcription or inhibit transcription of a structural sequence linked in cis; such enhancement or inhibition may be contingent on the occurrence of a specific event, such as stimulation with an inducer and/or may only be manifest in certain cell types. The altered ability to modulate transcriptional enhancement or inhibition may affect the inducible transcription of a gene or may effect the basal level transcription of a gene, or both. Numerous other specific examples of transcription regulatory elements, such as specific enhancers and silencers, are known to those of skill in the art and may be selected for use in the methods and polynucleotide constructs of the invention on the basis of the practitioner's desired application. Literature sources and published patent documents, as well as GenBank and other sequence information data sources can be consulted by those of skill in the art in selecting suitable transcription regulatory elements for use in the invention. Where necessary, a transcription regulatory element may be constructed by synthesis (and ligation, if necessary) of oligonucleotides made on the basis of available sequence information (e.g., GenBank sequences for a CD4 enhancer or a SV40 early promoter).

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, MRNA stability controlling sequences).

As used herein, the term "transcription regulatory region" refers to a DNA sequence comprising a functional promoter and any associated transcription elements (e.g., enhancer, CCAAT box, TATA box, SP1 site, etc.) that are essential for transcription of a polynucleotide sequence that is operably linked to the transcription regulatory region.

As used herein, the term "xenogeneic" is defined in relation to a recipient viral genome, mammalian host cell, or nonhuman animal and means that an amino acid sequence or polynucleotide sequence is not encoded by or present in, respectively, the naturally-occurring genome of the recipient viral genome, mammalian host cell, or nonhuman animal. Xenogenic DNA sequences are foreign DNA sequences; for example, human APP genes or immunoglobulin genes are xenogenic with respect to murine ES cells; also, for illustration, an HSV tk gene is xenogenic with respect to an HIV-1 genome. Further, a nucleic acid sequence that has been substantially mutated (e.g., by site directed mutagenesis) is xenogenic with respect to the genome from which the sequence was originally derived, if the mutated sequence does not naturally occur in the genome.

As used herein, the term "minigene" or "minilocus" refers to a heterologous gene construct wherein one or more nonessential segments of a gene are deleted with respect to the naturally-occurring gene. Typically, deleted segments are intronic sequences of at least about 100 basepairs to several kilobases, and may span up to several tens of kilobases or more. Isolation and manipulation of large (i.e., greater than about 50 kilobases) targeting constructs is frequently difficult and may reduce the efficiency of transferring the targeting construct into a host cell. Thus, it is frequently desirable to reduce the size of a targeting construct by deleting one or more nonessential portions of the gene. Typically, intronic sequences that do not encompass essential regulatory elements may be deleted. Frequently, if convenient restriction sites bound a nonessential intronic sequence of a cloned gene sequence, a deletion of the intronic sequence may be produced by: (1) digesting the cloned DNA with the appropriate restriction enzymes, (2) separating the restriction fragments (e.g., by electrophoresis), (3) isolating the restriction fragments encompassing the essential exons and regulatory elements, and (4) ligating the isolated restriction fragments to form a minigene wherein the exons are in the same linear order as is present in the germline copy of the naturally-occurring gene. Alternate methods for producing a minigene will be apparent to those of skill in the art (e.g., ligation of partial genomic clones which encompass essential exons but which lack portions of intronic sequence). Most typically, the gene segments comprising a minigene will be arranged in the same linear order as is present in the germline gene, however, this will not always be the case. Some desired regulatory elements (e.g., enhancers, silencers) may be relatively position-insensitive, so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some genes may have exons which are alternatively spliced at the RNA level, and thus a minigene may have fewer exons and/or exons in a different linear order than the corresponding germline gene and still encode a functional gene product. A cDNA encoding a gene product may also be used to construct a minigene. However, since it is generally desirable that the heterologous minigene be expressed similarly to the cognate naturally-occurring nonhuman gene, transcription of a cDNA minigene typically is driven by a linked gene promoter and enhancer from the naturally-occurring gene.

As used herein, the terms "endogenous DNA sequence" and "endogenous target sequence" refer to polynucleotide sequences contained in a eukaryotic cell. Such sequences include, for example, chromosomal sequences (e.g., structural genes, promoters, enhancers, recombinatorial hotspots, repeat sequences, integrated proviral sequences), episomal sequences (e.g., replicable plasmids or viral replication intermediates), chloroplast and mitochondrial DNA sequences. An exogenous polynucleotide is a polynucleotide which is transferred into a eukaryotic cell but which has not been replicated in that host cell; for example, a virus genome polynucleotide that enters a cell by fusion of a virion to the cell is an exogenous polynucleotide, however, replicated copies of the viral polynucleotide subsequently made in the infected cell are endogenous sequences (and may, for example, become integrated into a cell chromosome). Similarly, transgenes which are transfected into a cell are exogenous polynucleotides, however integrated and replicated copies of the transgene(s) are endogenous sequences.

The term "corresponds to" is used herein to mean that a polynucleotide sequence is homologous (i.e., identical) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "5'-TATAC" corresponds to a reference sequence "5'-TATAC" and is complementary to a reference sequence "5'-GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length viral gene or virus genome. Generally, a reference sequence is at least 20 nucleotides in length, frequently at least 25 nucleotides in length, and often at least 50 nucleotides in length. Since two polynucleotides may each comprise (1) a sequence (i.e., a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which for comparative purposes in this manner does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence over a comparison window of at least 20 nucleotide positions, optionally over a window of at least 30–50 nucleotides, wherein the percentage of sequence identity is calculated by comparing the reference sequence to the polynucleotide sequence that may include deletions or additions which total 20 percent or less of the reference sequence over the window of comparison. The reference sequence may be a subset of a larger sequence, for example, as a segment of the full-length viral gene or virus genome.

Specific hybridization is defined herein as the formation, by hydrogen bonding or nucleotide (or nucleobase) bases, of hybrids between a probe polynucleotide (e.g., a polynucleotide of the invention and a specific target polynucleotide (e.g., a viral gene or virus genome), wherein the probe preferentially hybridizes to the specific target such that, for example, a single band corresponding to, e.g., one or more of the RNA species of the gene (or specifically cleaved or processed RNA species) can be identified on a Northern blot of RNA prepared from a suitable source (e.g., a virus-infected somatic cell expressing the viral gene). Such hybrids may be completely or only partially base-paired. Polynucleotides of the invention which specifically hybridize to viral genome sequences may be prepared on the basis of the sequence data provided herein and available in the patent applications incorporated herein and scientific and patent publications noted above, and according to methods and thermodynamic principles known in the art and described in Sambrook et al. et al., Molecular Cloning: A Laboratory Manual, 2nd Ed., (1989), Cold Spring Harbor, N.Y.; Berger and Kimmel, Methods in Enzymology, Volume 152, Guide to Molecular Cloning Techniques (1987), Academic Press, Inc., San Diego, Calif.; Goodspeed et al. (1989) Gene 76: 1; Dunn et al. (1989) J. Biol. Chem. 264: 13057, and Dunn et al. (1988) J. Biol. Chem. 263: 10878, which are each incorporated herein by reference.

As used herein the term "replication conditions" refer to aqueous conditions wherein a virus or virus genome is capable of undergoing at least one principal step of viral replication, wherein the principal step can include: attachment of virion to host cell, entry of viral genome into host cell, uncoating of virus, polynucleotide replication (RNA transcription (plus or minus strand), reverse transcription, DNA-templated DNA polymerization, viral gene expression, encapsidation, budding, and the like. In general, conditions which result in a replication phenotype (see, infra) are replication conditions. Often, suitable replication conditions can be physiological conditions. "Physiological conditions" as used herein refers to temperature, pH, ionic strength, viscosity, and like biochemical parameters that are compatible with a viable organism, and/or that typically exist intracellularly in a viable cultured mammalian cell, particularly conditions existing in the nucleus of said mammalian cell. For example, the intranuclear or cytoplasmic conditions in a mammalian cell grown under typical laboratory culture conditions are physiological conditions. Suitable in vitro reaction conditions for in vitro transcription cocktails are generally physiological conditions, and may be exemplified by a variety of art-known nuclear extracts. In general, in vitro physiological conditions can comprise 50–200 mM NaCl or KCl, pH 6.5–8.5, 20–45° C. and 0.001–10 mM divalent cation (e.g., Mg++, Ca++); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s), metal chelators, nonionic detergents, membrane fractions, antifoam agents, and/or scintillants.

As used herein, the term "replication phenotype" refers to one or more of the following phenotypic characteristics of cells infected with a virus: (1) substantial expression of late gene products, such as capsid proteins (e.g., adenoviral penton base polypeptide) or RNA transcripts initiated from viral late gene promoter(s), (2) replication of viral genomes or formation of replicative intermediates, (3) assembly of viral capsids or packaged virion particles, (4) appearance of cytopathic effect (CPE) in the infected cell, (5) completion of a viral lytic cycle, and (6) other phenotypic alterations which are typically contingent upon substantial replication of a virus in cells infected with a wild-type replication competent virus encoding functional viral protein(s). A replication phenotype comprises at least one of the listed phenotypic characteristics, preferably more than one of the phenotypic characteristics.

As used herein, the term "replication deficient virus" refers to a virus that supports expression of a virus replication phenotype, and which is substantially unable to independently complete the replication cycle to produce infectious virions in the absence of helper virus or helper functions acting in trans. Typically, a replication deficient virus exhibits a substantial decrease in plaquing efficiency on cells conventionally used to plaque titer a parent virus.

As used herein, the terms "label" or "labeled" refer to incorporation of a detectable marker, e.g., a radiolabeled amino acid or a recoverable label (e.g. biotinyl moieties that can be recovered by avidin or streptavidin). Recoverable labels can include covalently linked polynucleobase sequences that can be recovered by hybridization to a complementary sequence polynucleotide. Various methods of labeling polypeptides, PNAs, and polynucleotides are known in the art and may be used. Examples of labels include, but are not limited to, the following: radioisotopes (e.g., $^3H$, $^{14}C$, $^{35}S$, $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). In some embodiments, labels are attached by spacer arms of various lengths, e.g., to reduce potential steric hindrance.

As used herein, the term "statistically significant" means a result (i.e., an assay readout) that generally is at least two standard deviations above or below the mean of at least three separate determinations of a control assay readout and/or that is statistically significant as determined by Student's t-test or other art-accepted measure of statistical significance.

The term "transcriptional modulation" is used herein to refer to the capacity to either enhance transcription or inhibit transcription of a structural sequence linked in cis; such enhancement or inhibition may be contingent on the occurrence of a specific event, such as stimulation with an inducer and/or may only be manifest in certain cell types.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antiviral agents by inclusion in screening assays described herein below.

The term "candidate agent" is used herein to refer to an agent which is identified by one or more screening method(s) of the invention as a putative antiviral agent. Some candidate antiviral agents may have therapeutic potential as drugs for human use.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, the term "optimized" is used to mean substantially improved in a desired structure or function relative to an initial starting condition, not necessarily the optimal structure or function which could be obtained if all possible combinatorial variants could be made and evaluated, a condition which is typically impractical due to the number of possible combinations and permutations in polynucleotide sequences of significant length (e.g., a complete viral gene or genome).

DETAILED DISCUSSION OF THE INVENTION

The invention relates in part to a generally applicable method for generating novel variant viruses having genotypes and phenotypes which do not naturally occur or would be anticipated to occur at a substantial frequency. A broad aspect of the method employs recursive nucleotide sequence recombination, termed "sequence shuffling", which enables the rapid generation of a collection of broadly diverse viral phenotypes that can be selectively bred for a broader range of novel phenotypes or more extreme phenotypes than would otherwise occur by natural evolution in the same time period. A basic variation of the method is a recursive process comprising: (1) sequence shuffling of a plurality of viral genomes, (2) selection of the resultant shuffled viral genomes to isolate or enrich a plurality of shuffled viral genomes having a desired phenotype(s), and (3) repeating steps (1) and (2) on the plurality of shuffled viral genomes having the desired phenotype(s) until one or more variant viral genomes having a sufficiently optimized desired phenotype is obtained. In this general manner, the method facilitates the "forced evolution" of a viral genome to encode a desired phenotype which natural selection and evolution has heretofore not generated. FIG. 1 shows a block diagram of a basic method for viral genome shuffling and selection for a desired phenotype; the recursion option is generally selected each cycle until one or more viral genomes having a satisfactory optimization for the desired phenotype(s) are obtained.

Typically, a plurality of viral genomes of the same taxonomic classification are shuffled and selected by the present method. It is believed that a common use of the method will be to shuffle mutant variants of a clinical isolate(s) or of a laboratory strain of a virus to obtain a variant of the clinical isolate or laboratory strain that possesses a novel desired phenotype. However, the method can be used with a plurality of strains (or clades) of a virus, or even with a plurality or related viruses (e.g., lentiviruses, herpesviruses, adenoviruses, etc.), and in some instances with unrelated viruses or portions thereof which have recombinogenic portions (either naturally or generated via genetic engineering). As long as two sequences have a region of sequence similarity, they can generally be combined.

Figure 2:
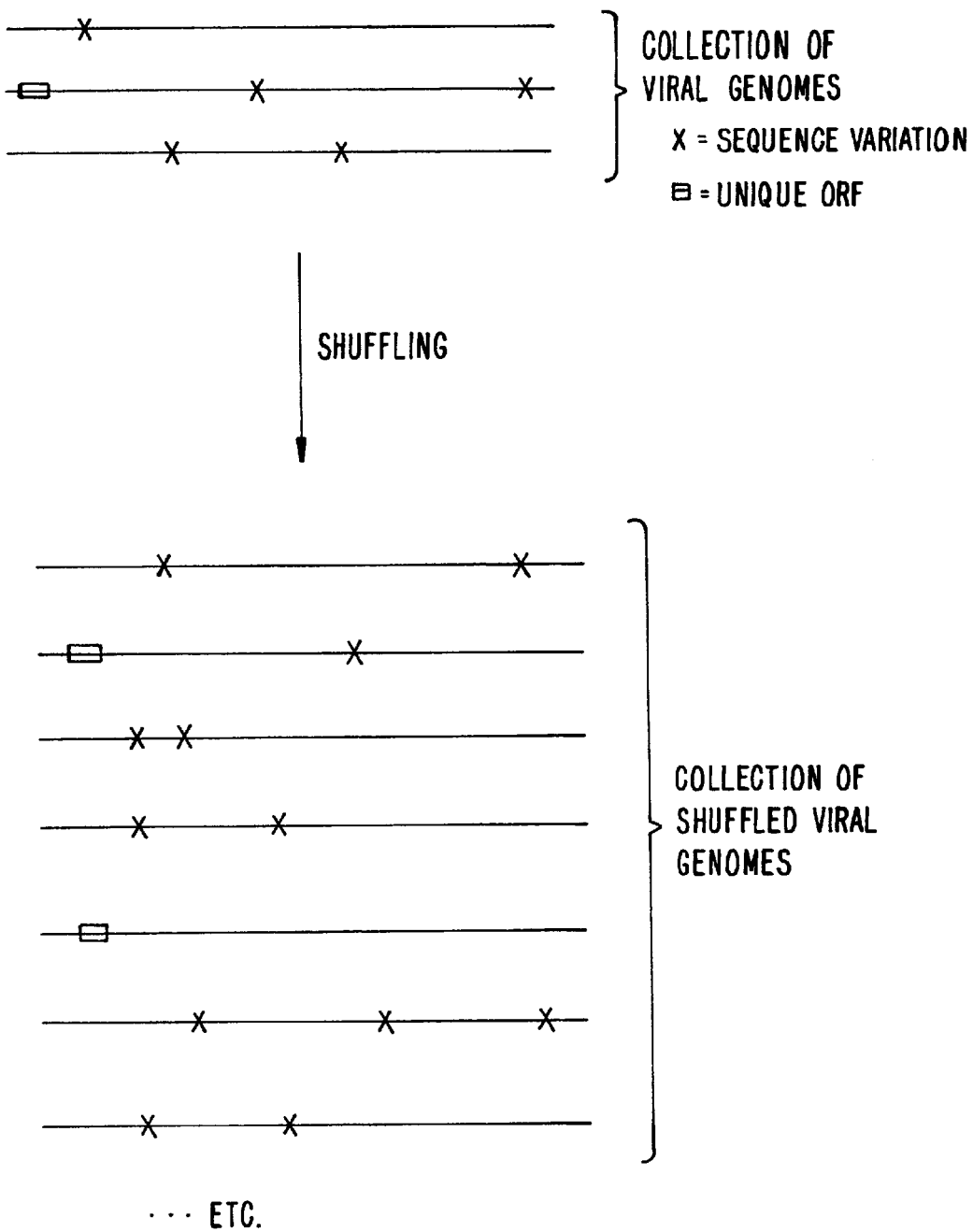
FIG. 2. Exemplary schematic of recombinatorial shuffling of a collection of viral genomes having a variety of mutations or distinct genome portions. Sequence variations are indicated with an (X) and a novel open reading frame (ORF) present in one viral isolate but absent in the others is identified as a box.

The method can be used to shuffle xenogeneic viral sequences into a viral genome (e.g., incorporating and evolving a gene of a first virus in the genome of a second virus so as to confer a desired phenotype to the evolved genome of the second virus). Furthermore, the method can be used to evolve a heterologous sequence (e.g., a non-naturally occurring mutant viral gene) to optimize its phenotypic expression (e.g., function) in a viral genome, and/or in a particular host cell or expression system (e.g., an expression cassette or expression replicon). FIG. 2 shows an example schematic representation of recombinatorial shuffling of a collection of viral genomes having a variety of mutations or distinct genome portions; positions of mutations are indicated by an (X), and distinct genome segments (e.g., obtained from the genomes of different virus isolates) are indicated by a open box.

In an aspect of the invention, the phenotype(s) which are selected for are the tropism and/or host range of the virus. Tropism is often defined as the cell type which can be productively infected by a virus (e.g., CD4+ T cells for HIV-1, nasopharyngeal epithelium for rhinovirus, etc.), and host range is commonly defined as the species of organism in which the virus can replicate (e.g., humans, simians, mice, rats, etc.). Both tropism and host range are believed to be restricted by the specific type(s) of proteins expressed by a cell; a cell lacking expression of a necessary protein that acts as a viral receptor may fail to support infection by the virus, similarly a virus may have evolved to use a host cell protein (e.g., polymerase) in one species (e.g., human) but not in another species (e.g., mouse). The present method can be used to create variant viruses which exhibit altered tropism or host range by employing the rapid forced evolution of shuffling to generate variant viruses that are adapted to the desired tropism or host range. As an example of this, HIV-1, which does not naturally replicate in mouse cells, can be evolved to do so by the present method. Similarly, it is believed that HIV-1, which normally does not infect human fibroblasts, can be evolved to do so by the present method. The method is general and can be employed to modify tropism and/or host range of substantially any virus suitable for recursive sequence shuffling (e.g., viruses that can be rescued as infectious virions following sequence shuffling). FIG. 3 shows a schematic portrayal of virus tropism/host range evolution by viral genome shuffling to produce recombinant variants capable of substantial replication in a non-human animal or cell line, such as a mouse.

The present method can also be employed to force evolution of host cells and transgenic animals to support infection and/or replication of a virus which normally does not infect or replicate in said cells or transgenic animal. For example, a transgenic mouse (or mouse cell line) expressing a transgene encoding a human chemokine receptor protein (e.g., CCR5, CXCR4) and/or a human CD4 protein can be improved for supporting infection by HIV-1 by selecting those transgenic mice (or transgenic mouse cells) which exhibit at least one, preferably more, positive phenotypic characteristics of HIV-1 infection (e.g., attachment of HIV-1, viral entry, replication, expression of a reporter gene encoded by HIV-1, production of infectious HIV-1 virions, etc.), and shuffling the transgenes (or portions thereof) from the selected mice (or cells) which encode the chemokine receptor protein(s) and/or human CD4. By recursive shuffling and selection, it is believed possible to force the evolution of transgene-encoded proteins which permit infection by HIV-1. HIV-1 variant viruses may be allowed to co-evolve with the transgenic mice (or transgenic mouse cells), or the transgenic mice (or cells) can be optimized to support naturally-occurring HIV-1 isolates.

Although described with specificity with respect to HIV-1, the present method can be used with substantially any type of virus having a genome suitable for in vitro or in vivo sequence shuffling, including but not limited to hepatitis C virus (HCV), adenovirus, adeno-associated virus (AAV), lentivirus, hepatitis B virus, HIV-2, murine leukemia virus (MLV) among others. Preferably, the viruses used in the method of the invention are suitable for cloning of an intact genome (or a substantial portion thereof), such that the genomic sequences can be shuffled by a recombination method of the invention, and the recombined viral genome (s) can be rescued as infectious virus, such as through the use of a helper cell line, helper virus, or in vitro reconstitution of replication intermediates (see, for example, U.S. Pat. No. 5,166,057 and WO97/12032). Such genome recovery and rescue systems are known in the art for many types of viruses, and can be applied by the practitioner to the virus type of interest. Thus, both viruses having either an RNA genome or DNA genome are suitable for use in the method. Intact genomes (or portions thereof) can be recovered from virions, as replicative intermediates from host cells, as cDNA copies, or as integrated provirus from a host cell genome (e.g., as a cosmid clone or lambda clone). The recovered viral genome sequences can be shuffled with other viral genome sequences and/or with one or more spiked polynucleotide specie(s) (e.g., mutation-bearing gene sequences or mutation-bearing intergenic viral genome sequences), which may include optimized components of a viral genome that have been separately optimized by shuffling (e.g., a Tat gene sequence or a tar sequence of HIV-1 which has been optimized for function in mouse cells). Optimized components typically can include expression cassettes encoding viral genes, viral transcriptional regulatory sequences, origins or replication, non-coding sequences important for replication (e.g., panhandle sequences of influenza virus genome segments), LTRs, repeat sequences, and the like. For viruses with segmented genomes, individual segments may be optimized separately by recursive sequence shuffling and selection, or a combination or all of the segments may be optimized collectively for a desired phenotype; it is also possible to combine one or more cycle(s) of individual component/segment evolution with one or more cycle(s) of collective component/segment evolution, in any order.

In an aspect of the invention, a plurality of replication defective viral genomes are shuffled and the resultant shuffled genomes are selected for the capacity to replicate in a desired cell type or host organism.

In an aspect of the invention, complementing genome portions of or complete genomes of two or more distinct virus types (e.g., HIV-1 and SIV) are shuffled and phenotype selected to generate and isolate one or more shuffled variant virus genomes that have a desired phenotype (e.g., the capacity to replicate in simian cells but retain a substantial portion of the HIV-1 genome). The resultant shufflants comprising a portion of an HIV-1 (or HIV-2) genome and a portion of an SIV genome, and having functional sequences sufficient to support replication in a host cell are termed "SHIV recombinants". Kuwata et al. (1996) AIDS 10: 1331 report chimeric viruses between SIV and various HIV-1 isolates that have biological properties similar to those of parental HIV-1. Unlike the present invention, the chimeras made by Kuwata et al. are simple recombinants of discrete genome portions of SIV and HIV-1, and are not the product of recursive sequence shuffling and selection for a desired phenotype.

Recombination Methods

The present invention provides methods, reagents, genetically modified animals and cells, and pharmaceutical compositions relating to the forced evolution of viral genomes, or portions thereof, having a desired phenotypic alteration generated by polynucleotide sequence shuffling of a plurality of viral genomes, typically of the same virus type (e.g., HIV-1, HCV, adenovirus, etc.).

Generally, the nomenclature used hereafter and the laboratory procedures in cell culture, molecular genetics, virology, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references.

For example, the practice of this invention involves the construction of recombinant nucleic acids, the expression of genes in transfected host cells and molecular library construction. Molecular cloning techniques to achieve these ends are known in the art. A wide variety of cloning and in vitro amplification methods suitable for the construction of recombinant nucleic acids such as expression vectors are well-known to persons of skill. General texts which describe molecular biological techniques useful herein, including mutagenesis, include Berger and Kimmel, *Guide to Molecular Cloning Techniques*, Methods in Enzymology volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1998) ("Ausubel")).

Examples of techniques sufficient to direct persons of skill through in vitro amplification methods, including the polymerase chain reaction (PCR) the ligase chain reaction (LCR), Q-replicase amplification and other RNA polymerase mediated techniques (e.g., NASBA) are found in Berger, Sambrook, and Ausubel, as well as Mullis et al.; (1987) U.S. Pat. No. 4,683,202; *Technology: Principles and Applications for DNA Amplification* ed. H A Erlich, Freeman Press, New York, N.Y. (1992); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference). *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) Science 241, 1077–1080; Van Brunt (1990) Biotechnology 8, 291–294; Wu and Wallace, (1989) Gene 4, 560; Barringer et al. (1990) Gene 89, 117, and Sooknanan and Malek (1995) Biotechnology 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as probes, e.g., in in vitro amplification methods, for use as gene probes, or as shuffling targets (e.g., synthetic genes or gene segments) are typically synthesized chemically according to the solid phase phosphoramidite triester method described by Beaucage and Caruthers (1981), Tetrahedron Letts., 22(20):1859–1862, e.g., using an automated synthesizer, as described in Needham-VanDevanter et al. (1984) Nucleic Acids Res., 12:6159–6168. Oligonucleotides can also be custom made and ordered from a variety of commercial sources known to persons of skill.

Indeed, essentially any nucleic acid with a known sequence can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technoloigies Inc. (Alameda, Calif.) and many others. Similarly, peptides and antibodies can be custom ordered from any of a variety of sources, such as PeptidoGenic (pkim@ccnet.com), HTI Bioproducts, inc. (http://www.htibio.com), BMA Biomedicals Ltd (U.K.), Bio.Synthesis, Inc., and many others.

Chimeric targeted mice are derived according to Hogan, et al., Manipulating the Mouse Embryo: A Laboratory Manual, Cold Spring Harbor Laboratory (1988) and Teratocarcinomas and Embryonic Stem Cells: A Practical Approach, E. J. Robertson, ed., IRL Press, Washington, D.C., (1987) which are incorporated herein by reference.

Embryonic stem cells are manipulated according to published procedures (Teratocarcinomas and Embryonic Stem Cells: A Practical Approach, E. J. Robertson, ed., IRL Press, Washington, D.C. (1987); Zjilstra et al., Nature 342:435–438 (1989); and Schwartzberg et al., Science 246:799–803 (1989), each of which is incorporated herein by reference).

All sequences referred to herein by GenBank database file designation (e.g., GenBank: Humatct4a) or a commonly used reference name which is indexed in GenBank are incorporated herein by reference and are publicly available.

DNA Shuffling

Exemplary formats and examples for sequence recombination, referred to, e.g., as "DNA shuffling," "fast forced evolution," or "molecular breeding," have been described by the present inventors and co-workers in the following patents and patent applications: U.S. Pat. No. 5,605,793; PCT Application WO 95/22625 (Ser. No. PCT/US95/02126), filed Feb. 17, 1995; U.S. Ser. No. 08/425,684, filed Apr. 18, 1995; U.S. Ser. No. 08/621,430, filed Mar. 25, 1996; PCT Application WO 97/20078 (Ser. No. PCT/US96/05480), filed Apr. 18, 1996; PCT Application WO 97/35966, filed Mar. 20, 1997; U.S. Ser. No. 08/675,502, filed Jul. 3, 1996; U.S. Ser. No. 08/721,824, filed Sep. 27, 1996; PCT Application WO 98/13487, filed Sep. 26, 1997; "Evolution of Whole Cells and Organisms by Recursive Sequence Recombination" Attorney Docket No. 018097-020720US filed Jul. 15, 1998 by del Cardayre et al. (U.S. Ser. No. 09/116,188); Stemmer, Science 270:1510 (1995); Stemmer et al., Gene 164:49–53 (1995); Stemmer, Bio/Technology 13:549–553 (1995); Stemmer, Proc. Natl. Acad. Sci. U.S.A. 91:10747–10751 (1994); Stemmer, Nature 370:389–391 (1994); Crameri et al., Nature Medicine 2(1):1–3 (1996); Stemmer, U.S. Pat. No. 5,811,238, and Crameri et al., Nature Biotechnology 14:315–319 (1996), each of which is incorporated by reference in its entirety for all purposes.

Nucleic acid sequence shuffling is a method for recursive in vitro or in vivo homologous or nonhomologous recombination of pools of nucleic acid fragments or polynucleotides (e.g., viral genomes or portions thereof). Mixtures of related nucleic acid sequences or polynucleotides are randomly or pseudorandomly fragmented, and reassembled to yield a library or mixed population of recombinant nucleic acid molecules or polynucleotides.

The present invention is directed to a method for generating a selected polynucleotide sequence (e.g., a viral genome or viral gene) or population of selected polynucleotide sequences, typically in the form of amplified and/or cloned polynucleotides, whereby the selected polynucleotide sequence(s) possess a desired phenotypic characteristic (e.g., encode a polypeptide, promote transcription of linked polynucleotides, bind a protein, and the like) which can be selected for, and whereby the selected polynucleotide sequences are viral genomes or genes having a desired functionality and/or conferring a desired phenotypic property to a viral genome. One method of identifying novel viral genome sequences that possess a desired structure or functional property, such as having an altered tropism or host range (e.g., a human virus capable of substantial infection and replication of a non-human host), involves the screening of a large library of recombinant viral sequences (which can be a component of a viral genome—e.g., part of a viral gene, non-coding transcriptional regulatory sequence, origin of replication,—or a complete viral genome) for individual library members which possess the desired structure or functional property conferred by the novel viral genome sequence.

In a general aspect, the invention provides a method, termed "sequence shuffling," for generating libraries of recombinant polynucleotides having a desired characteristic which can be selected or screened for. Libraries of recombinant polynucleotides are generated from a population of related-sequence polynucleotides which comprise sequence regions which have substantial sequence identity and can be homologously recombined in vitro or in vivo. In the method, at least two species of the related-sequence polynucleotides are combined in a recombination system suitable for generating sequence-recombined polynucleotides, wherein said sequence-recombined polynucleotides comprise a portion of at least one first species of a related-sequence polynucleotide with at least one adjacent portion of at least one second species of a related-sequence polynucleotide.

Recombination systems suitable for generating sequence-recombined polynucleotides can be either: (1) in vitro systems for homologous recombination or sequence shuffling via amplification or other formats described herein, (2) in vivo systems for homologous recombination or site-specific recombination as described herein, or template-switching of a retroviral genome replication event or (3) whole genome approaches in which entire genomes are shuffled. The population of sequence-recombined polynucleotides comprises a subpopulation of polynucleotides which possess desired or advantageous characteristics and which can be selected by a suitable selection or screening method. The selected sequence-recombined polynucleotides, which are typically related-sequence polynucleotides, can then be subjected to at least one recursive cycle wherein at least one selected sequence-recombined polynucleotide is combined with at least one distinct species of related-sequence polynucleotide (which may itself be a selected sequence-recombined polynucleotide) in a recombination system suitable for generating sequence-recombined polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined polynucleotides possessing desired characteristics. Such characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property.

Screening/selection produces a subpopulation of viruses (or cells) expressing recombinant forms of gene(s) or virus genomes that have evolved toward acquisition of a desired property. These recombinant forms can then be subjected to further rounds of recombination and screening/selection in any order. For example, a second round of screening/selection can be performed analogous to the first resulting in greater enrichment for genes having evolved toward acquisition of the desired property (e.g., tropism of a virus in a selected cell type). Optionally, the stringency of selection can be increased between rounds (e.g., if selecting for drug resistance, the concentration of drug in the media can be increased). Further rounds of recombination can also be performed by an analogous strategy to the first round generating further recombinant forms of the gene(s) or genome(s). Alternatively, further rounds of recombination can be performed by any of the other molecular breeding formats discussed. Eventually, a recombinant form of the gene(s) or genome(s)is generated that has fully acquired the desired property.

The method of shuffling can generate libraries of polynucleotides (viral genomes, transgene polynucleotides) encoding selectable properties, including altered tropism and/or host range, which can compose all or a part of a viral genome or host cell transgene, wherein the library is suitable for function optimization of a gene or regulatory sequence or phenotypic screening. The method comprises, e.g., (1) obtaining a first plurality of library members comprising a viral genome, viral gene, viral regulatory or replication sequence, or host cell transgene (or encoding sequence or expression cassette thereof), and obtaining from said library a polynucleotide, or copy thereof, complete or partial, of at least one selected library member having a detectable desired phenotype, optionally introducing mutations into said polynucleotide or copy(ies), and (2) pooling and fragmenting, by nuclease digestion, partial extension PCR amplification, PCR stuttering, or other suitable fragmenting means, typically producing random fragments or fragment equivalents, said selected polynucleotide(s) or copies to form fragments thereof under conditions suitable for PCR amplification, performing PCR amplification and optionally mutagenesis, and thereby homologously recombining said fragments to form a shuffled pool of recombined polynucleotides, whereby a substantial fraction (e.g., greater than 10 percent) of the recombined polynucleotides of said shuffled pool are not present in the first plurality of selected library members, said shuffled pool composing a library of shuffled selected variant viral genome sequences or transgene sequences suitable for functional screening or phenotype screening. Optionally, the method comprises the additional step of screening the library members of the shuffled pool to identify individual shuffled library members having the desired functional ability or phenotype. The novel shuffled viral genomes, viral genome sequences, and transgene sequences that are identified from such libraries can be used for model non-human systems of viral replication, infection, antiviral agent screening, candidate attenuated live virus vaccines and therapeutics, and the like; and/or can be subjected to one or more additional cycles of shuffling and/or functional optimization or phenotype selection for further optimization. The method can be modified such that the step of selecting is for a phenotypic characteristic other than viral infectivity, replication, host range, tropism, gene function, transcriptional regulatory sequence function, or the like.

In an embodiment, the first plurality of selected library members is fragmented and homologously recombined by PCR in vitro. Fragment generation is by nuclease digestion, partial extension PCR amplification, PCR stuttering, or other suitable fragmenting means, such as described herein and in WO95/22625 published Aug. 24, 1995, and in commonly owned U.S. Ser. No. 08/621,859 filed Mar. 25, 1996, PCT/US96/05480 filed Apr. 18, 1996, which are incorporated herein by reference). Stuttering is fragmentation by incomplete polymerase extension of templates. A recombination format based on very short PCR extension times can be employed to create partial PCR products, which continue to extend off a different template in the next (and subsequent) cycle(s), and effect de facto fragmentation. Template-switching and other formats which accomplish sequence shuffling between a plurality of sequence-related polynucleotides can be used. Such alternative formats will be apparent to those skilled in the art.

In an embodiment, the first plurality of selected library members is fragmented in vitro, the resultant fragments transferred into a host cell or organism and homologously recombined to form shuffled library members in vivo.

In an embodiment, the first plurality of selected library members is cloned or amplified on episomally replicable vectors, a multiplicity of said vectors is transferred into a cell and homologously recombined to form shuffled library members in vivo.

In an embodiment, the first plurality of selected library members is not fragmented, but is cloned or amplified on an episomally replicable vector as a direct repeat or indirect (or inverted) repeat, which each repeat comprising a distinct species of selected library member sequence, said vector is transferred into a cell and homologously recombined by intra-vector or inter-vector recombination to form shuffled library members in vivo.

In an embodiment, first plurality of selected library members is replicated under conditions wherein retroviral template switching between at least two xenogeneic viral genomes occurs, typically involving retroviral genomes or non-retroviral genes cloned into a retroviral replication system.

In an embodiment, combinations of in vitro and in vivo shuffling are provided to enhance combinatorial diversity. The recombination cycles (in vitro or in vivo) can be performed in any order desired by the practitioner.

The present invention provides a method for generating libraries of viral genomes or viral genetic sequences suitable for phenotype screening, such as to generate enhanced function in a cell type and/or animal species, modify viral tropism or host range, or other desired property. The method comprises (1) obtaining a first plurality of library members comprising a viral genome polynucleotide or portion thereof, (2) pooling and fragmenting said polynucleotides or copies to form fragments thereof under conditions suitable for PCR amplification and thereby homologously recombining said fragments to form a shuffled pool of recombinant polynucleotides comprising novel combinations of viral sequences, whereby a substantial fraction (e.g., greater than 10 percent) of the recombined polynucleotides of said shuffled pool comprise viral genome sequence combinations which are not present in the first plurality of library members, said shuffled pool composing a library of viral genome sequences comprising sequence combinations suitable for phenotype screening. Optionally, the plurality of selected shuffled library members can be shuffled and screened iteratively, from 1 to about 1000 cycles or as desired until library members having a desired binding affinity are obtained. Often, from 2 to 25 cycles of recursion are performed before a sufficiently optimized shufflant (i.e., selected shuffled library member) is obtained. The degree of optimization for any particular application will vary based on the specific intended use and other considerations (e.g., time, minimization of mutational drift, etc.) that are selected by the practitioner.

The invention also provides the use of polynucleotide shuffling to shuffle a population of viral genes (e.g., capsid proteins, spike glycoproteins, polymerases, proteases, etc.) or viral genomes (e.g., adenoviruses, AAV, MoMuLV, HCV, lentiviruses, retroviruses or any other known classification) to develop enhanced viral genomes having a desired phenotypic property. In an embodiment, the invention provides a method for shuffling sequences encoding all or portions of immunogenic viral proteins to generate novel combinations of epitopes as well as novel epitopes created by recombination to provide gene therapy vectors which elicit (or avoid) strong immune responses in a host. In an embodiment, the invention provides viral vectors which have enhanced capacity to infect a desired target cell population and/or an enhanced cell type specificity to reduce infection of non-target cells. In one aspect, such improved viral vectors can serve as platforms for delivery of gene therapy sequences or vector-encoded immunogenic vaccine epitopes to a host.

For viral genome sequence shuffling (or transgene shuffling) by homologous recombination (including by PCR-based homology overlaps) at least two species of the related-sequence polynucleotides are combined in a recombination system suitable for generating sequence-recombined polynucleotides, wherein said sequence-recombined polynucleotides comprise a portion of at least one first species of a related-sequence polynucleotide with at least one adjacent portion of at least one second species of a related-sequence polynucleotide. Recombination systems suitable for generating sequence-recombined polynucleotides can be either: (1) in vitro systems for homologous recombination or sequence shuffling via amplification or other formats described herein, or (2) in vivo systems for homologous recombination or site-specific recombination as described herein. The population of sequence-recombined polynucleotides comprises a subpopulation of polynucleotides which possess desired or advantageous characteristics and which can be selected by a suitable selection or screening method. The selected sequence-recombined polynucleotides, which are typically related-sequence polynucleotides, can then be subjected to at least one recursive cycle wherein at least one selected sequence-recombined polynucleotide is combined with at least one distinct species of related-sequence polynucleotide (which may itself be a selected sequence-recombined polynucleotide) in a recombination system suitable for generating sequence-recombined polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined polynucleotides possessing desired characteristics. Such characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. A particular advantageous property is an altered tropism or host range which allows a human-tropic virus to infect and replicate in a non-human host animal or non-human cell type, or an altered tropism which allows a virus to replicate in a cell line which has desirable features (e.g., a cell line that has been approved by regulatory authorities, or is conveniently cultured, or the like) or altered cell tropism in a host (e.g., adenovirus that selectively infects melanoma cells and specialized Ag-presenting cells, and the like).

Forced Evolution of Models of Viral Disease

The invention provides a means to evolve virus variants and/or host cells (or organisms) that are convenient non-human model systems for studying virus-induced pathology, virulence factors, attenuated live-viral vaccine candidates, and other aspects of viral infections, as well as providing a model system for evaluating a library of agents to identify candidate antiviral agents that could find use as prophylactic and/or therapeutic drugs for human and veterinary applications.

The methods of the invention can be used to force the evolution of a virus which has a host range or tropism that limits its infectivity and/or replication to hosts which are inconvenient to use as a model system (e.g., humans or other primates, large mammals, etc.). For example, a virus which has a host range restricted to humans can be modified by recursive sequence shuffling and selection for growth in a non-human host (organism or cell culture) to produce shuffled variants that have significantly improved capacity to infect and/or replicate and produce infectious virions in the non-human host. In instances where there is no detectable infection or replication in a non-human host, shuffling of the virus of interest with a virus of a similar taxonomic type which is known to infect and/or replicate in the non-human host may generate a population of shuffled viral genomes which population contains one or more shuffled virus genomes that can replicate, at least weakly, in the non-human host. By obtaining at least one variant shuffled genome having some level of infection and replication in the non-human host (termed a "sparkplug variant"), the population of replicated virions can be collected from the non-human host system and subjected to subsequent rounds of genome shuffling with: (1) each other, (2) one or more parental viral genomes, (3) mutated genomes (or portions thereof) of the collected, replicated virion genomes (i.e., intentionally mutated genome sequences of the sparkplug variants—such as by spiking with mutagenic oligonucleotides, error-prone PCR, or other suitable mutational methodology), (4) optimized viral genome components (e.g., viral genes or non-coding regions which have been separately optimized for function in the non-human host), or (5) combinations of the above, in any order, among others.

In some instances, it may be difficult or impractical to generate the initial sparkplug variants by shuffling entire viral genomes; in such cases, it is generally preferred that one or more individual components of the viral genome (e.g., genes, non-coding regulatory sequences, replication origins, essential structural sequences) from a parental virus are optimized for functionality in the non-human host. A parental virus (or collection thereof) can then be shuffled with one or more optimized individual component(s), including, if desired, multiple species of an optimized component, to generate a population of shuffled variant viral genomes which incorporate viral genome portions that have been optimized for function in the non-human host. This general approach to the shuffling method can be referred to as a "bottom-up" approach, in contradistinction to the variation where genomes of existing viral isolates are shuffled to create at least one "sparkplug variant" that replicates in the non-human host (i.e., a "top-down" approach).

In some instances, it may be desirable or necessary to also evolve (or co-evolve with the virus), by recursive sequence shuffling and selection, a non-human host or genetic components thereof.

For example and not to limit the invention, HIV-1 has been reported to require certain human proteins (e.g., CD4, CCR5, CXCR4, and the like) for infectivity of cells (see, WO97/28258; Moore and Trkola (1997) *AIDS Research and Human Retroviruses* 13: 733; and Bour et al. (1995) *Microbiological Reviews* 59: 63), and possibly certain human genes for efficient replication in non-human cells (Hart et al. (1989) *Science* 246: 488). For example, a mouse (or mouse cell) harboring a transgene which expresses one or more species of human protein involved in HIV-1 infection and/or replication (e.g., CD4, CCR5, CXCR4, or a tat transgene that has been evolved to efficiently promoter transcription of HIV-1 in mouse cells) benefits from optimization for function in the non-human host; recursive sequence shuffling and selection can be used to generate optimized variants of such transgene(s). Host organisms or host cells harboring transgenes which exhibit some level of functionality (e.g., ability to be infected with and/or replicate virus) can be selected for, the transgene sequence (or portion(s) thereof) recovered, and the recovered transgene sequence then shuffled with other such recovered transgene sequences and/or intentionally mutated transgene sequences to generate a population of shuffled transgene sequences that can be used to reconstitute transgenes that can be transferred into a subsequent generation of non-human host organisms or cells for one or more further rounds of selection for virus replication and shuffling, and so on. In certain embodiments, the directed evolution of the viral variants and the directed evolution of the transgene sequences of the non-human host can be done in parallel, if desired, so as to co-evolve a virus variant/host variant combination with optimized function to support virus infectivity and/or replication (or other desired feature).

Granularity of Shuffling

The "granularity" of a shuffling event refers to the relative average density of recombination joints per unit length (e.g., per kilobase) or per recombined polynucleotide molecule (e.g., per functional viral genome). For illustration, a coarse granularity could be an average of one or less recombination joint per polynucleotide resulting from a shuffling (i.e., sequence recombination event); a coarse granularity of shuffling generates a "low crossover library" (as shown diagrammatically in FIG. 5). It is often desirable to alter the granularity of shuffling in different recursion cycles, although this is not necessary in many cases. The granularity desired can frequently be selected by the practitioner and is typically accomplished by controlling the degree of recombination in the recombination format selected (e.g., for a fragmentation/reassembly format, a high degree of fragmentation will generate a small average fragment size and hence a finer granularity; increasing the number of polynucleotide species shuffled can also be used to obtain finer granularity, among other ways apparent to those skilled in the art). The average size of segment from the parental sequence(s) represented in the library of sequence-recombined polynucleotides is denoted as the "average segment length", and may be expressed by unit length (e.g., per kilobase) or as a fraction of the parental sequence (e.g., one-quarter genome of HIV-1).

If a mutational strategy is employed, it is frequently desirable to select a granularity which results in an average segment length wherein, on average, one mutation (or slightly less) per segment is present.

Figure 5:
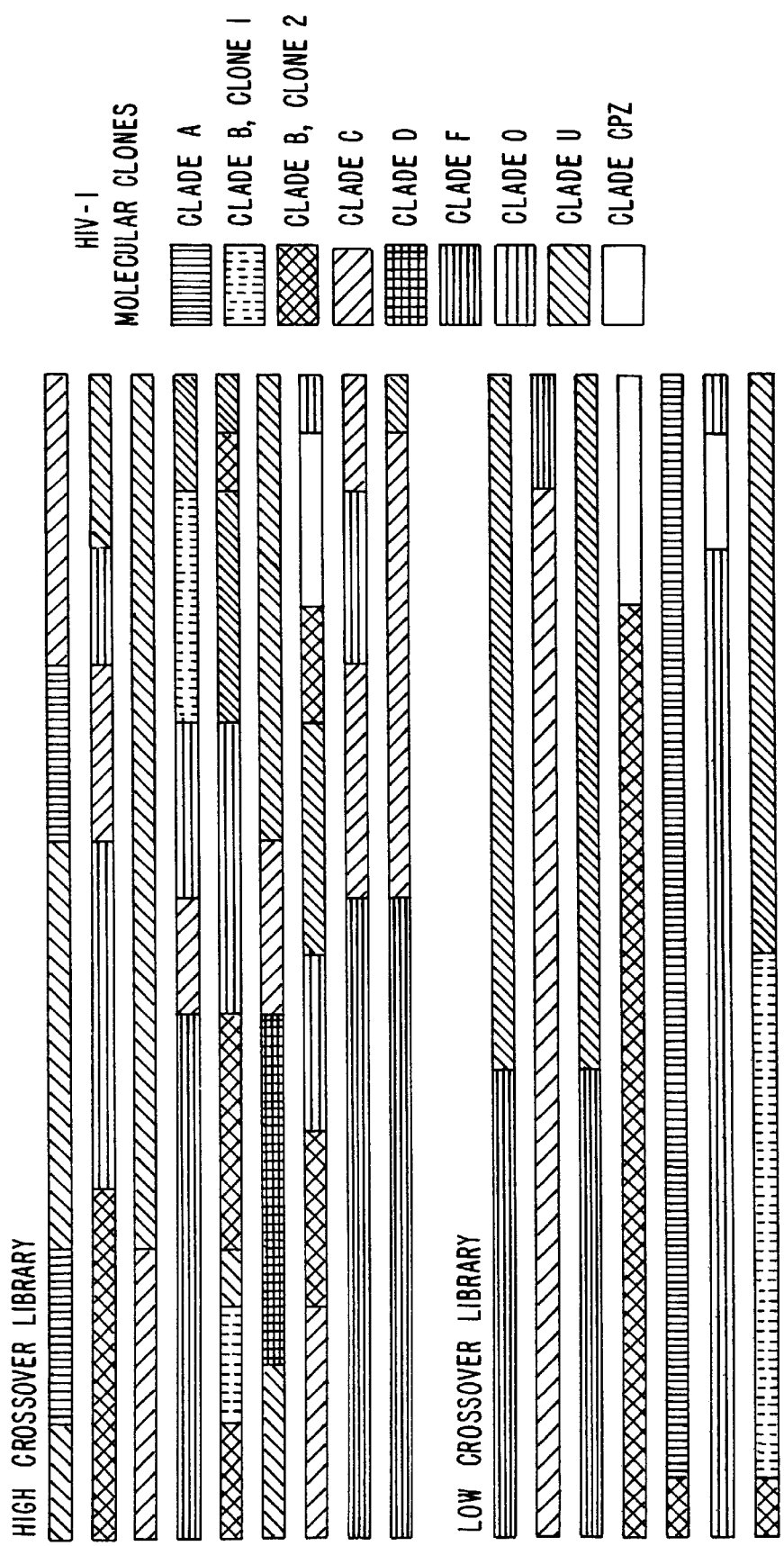
FIG. 5. Diagram showing an example of a low crossover library of sequence-recombined polynucleotides resulting from coarse granularity shuffling, as compared to a high crossover library resulting from a fine granularity shuffling. Each unique color (shade) represents nucleotide sequence from a distinct sequence variant (e.g., from a mutated parental sequence, from a plurality of viral isolates or clades, etc.).

The present method permits the construction of a library of shuffled viral genomes (or genome portions) wherein the library contains a population of shuffled genomes of any granularity desired by the practitioner. Libraries prepared from a plurality of parental viral genomes can be made to have substantially any granularity; for example a viral genome library having, on average, at least two recombination joints (e.g., three distinct segments) per sequence-recombined genome can be generated, as can viral genomes having three, four, five, six, seven, eight, nine, ten, or more recombination joints (e.g., a viral genomic polynucleotide composed of 4,5,6,7,8,9,10, or 11 or more distinct sequence segments). FIG. 5 shows a schematic representation of high crossover (fine granularity) and low crossover (coarse granularity) libraries.

Spiking

Figure 6:
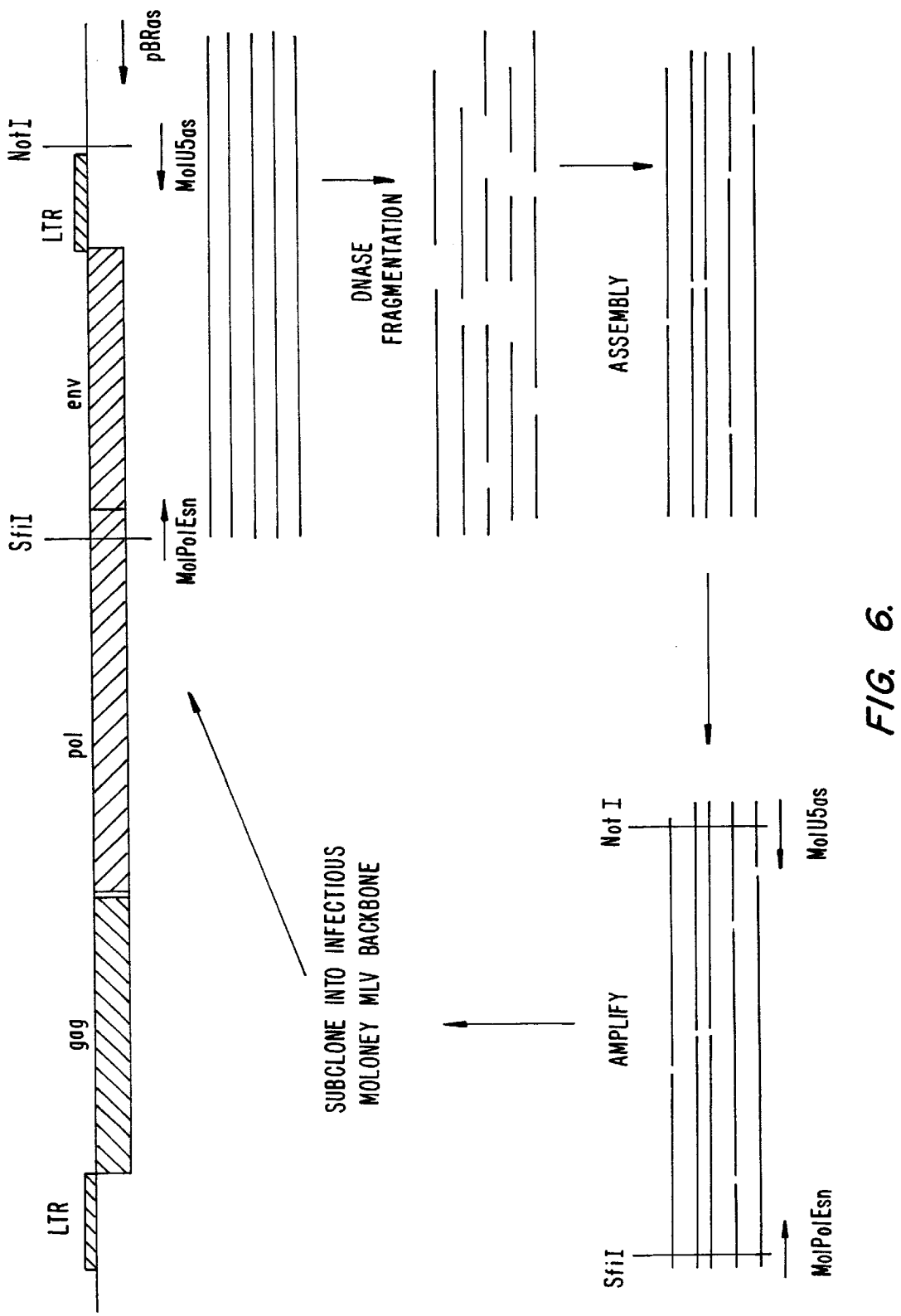
FIG. 6. Schematic Diagram for Construction of shuffled library.

The basic sequence shuffling methodology can be used to shuffle a collection of related sequences, wherein most or all of the related sequences substantially span a certain physical portion of a gene or genome (e.g., a structural gene, a transcriptional regulatory sequence, a replication origin, or an entire viral genome). For example, the collection of related polynucleotides could represent, e.g., alleles of a gene locus, variant viral genes, or genomes of distinct virus isolates). However, in some embodiments it is desirable to focus evolutionary pressure principally on one or more discrete segments of a genomic polynucleotide (e.g., a specific viral gene) or of a particular gene (e.g., on a specific functional domain or conserved sequence of a gene). One methodological modification to focus sequence diversity on a particular segment of a genome is to "spike" a recombination reaction with additional polynucleotides which represent only a subset of the locus being shuffled. These "spiking polynucleotides" can enhance the potential sequence diversity at the locus subset (e.g., randomly or pseudorandomly increase mutation density at the locus subset), or can over-represent (or under-represent) certain predetermined sequences in order to steer the sequence diversity in a predetermined direction (e.g., to over-represent mutations which tend to produce a beneficial result based on prior results). FIG. 6 shows a schematic portrayal of a spiking embodiment. A spiking variation of the basic method of shuffling can be exemplified by a recombination reaction in which several HIV-1 clinical isolate genomes are shuffled, and a spiking mixture composed of subgenomic sequences (e.g., mutated Tat gene sequences) are included to produce a resultant shuffled library of HIV-1 genomes having enhanced sequence diversity at the Tat locus. In some embodiments, the spiking polynucleotides are viral genome components which have been optimized separately for a desired phenotype (e.g., functionality in mouse cells) and are being shuffled into a collection of viral genomes to introduce said desired phenotype into the viral genomes.

Backcrossing

After a desired phenotype is acquired to a satisfactory extent by a selected shuffled viral genome or portion thereof, it is often desirable to remove mutations which are not essential or substantially important to retention of the desired phenotype ("superfluous mutations"). Superfluous mutations can be removed by backcrossing, which is shuffling the selected shuffled viral genome(s) with one or more parental viral genome and/or naturally-occurring viral genome(s) (or portions thereof) and selecting the resultant collection of shufflants for those species that retain the desired phenotype. By employing this method, typically in two or more recursive cycles of shuffling against parental or naturally-occurring viral genome(s) (or portions thereof) and selection for retention of the desired phenotype, it is possible to generate and isolate selected shufflants which incorporate substantially only those mutations necessary to confer the desired phenotype, whilst having the remainder of the genome (or portion thereof) consist of sequence which is substantially identical to the parental (or wild-type) sequence(s). As one example of backcrossing, an HIV-1 genome can be shuffled and selected for the capacity to substantially infect and replicate in mouse cells; the resultant selected shufflants can be backcrossed with one or more genomes of clinical isolates of HIV-1 and selected for the capacity to retain the capacity to infect and replicate in mouse cells. After several cycles of such backcrossing, the backcrossing will yield HIV-1 genome(s) which contain the mutations necessary for replication and infection of mouse cells, and will otherwise have a genomic sequence substantially identical to the genome(s) of the clinical isolate(s) of HIV-1.

Isolated components (e.g., genes, regulatory sequences, packaging sequences, replication origins, and the like) can be optimized and then backcrossed with parental sequences so as to obtain optimized components which are substantially free of superfluous mutations.

Transgenic Hosts

For some embodiments of viral genome shuffling wherein a desired product is a non-human model system for a viral disease, it is sometimes necessary to introduce one or more transgenes (or replacement genes—if by homologous recombination to replace an endogenous non-human gene with a human gene) that encode a human protein important for substantial infection, replication, and/or production of infectious virions, of the subject virus. For example, mice or mouse cells transgenic for expression of human CD4 and human CCR5 (optionally also human CXCR4) can be used as hosts for shuffled HIV-1 genomes. Other primate (including human) cytokine receptor proteins which facilitate HIV infection (e.g., attachment and/or entry into a host cell) can be expressed from a transgene or expression vector in a host cell or organism, typically in combination with human CD4 and/or human CCR5 and/or human CXCR4.

In one aspect of the invention, transgenic nonhuman animals, such as mice, bearing a transgene encoding a human cytokine receptor polypeptide and/or a human CD4 polypeptide are provided. Such transgenes may be homologously recombined into the host chromosome or may be non-homologously integrated. Additionally, a human cytokine receptor (and/or human CD4) cDNA or genomic gene copy may be used to construct transgenes for expressing cytokine receptor (or CD4) polypeptides at high levels and/or under the transcriptional control of transcription control sequences which do not naturally occur adjacent to the cytokine receptor (or CD4) gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a encoding polynucleotide sequence to form a transgene (typically in combination with a selectable marker such as a neo gene expression cassette). Such transgenes, which can include minigenes, can be introduced into cells (e.g., ES cells, hematopoietic stem cells) and transgenic cells and transgenic nonhuman animals may be obtained according to conventional methods. Transgenic cells and/or transgenic nonhuman animals may be used: (1) to screen for desired HIV-1 variants capable of infection and/or replication in non-human (e.g., mouse) cells, (2) in conjunction with a mouse-adapted HIV-1 variant, to identify antiviral compounds in an agent library, wherein said antiviral compound inhibits replication of a nonhuman-adapted HIV-1 in said transgenic non-human animal (e.g., mouse) or transgenic non-human cells, and (3) other uses apparent to those in the art in view of this disclosure. In some embodiments, a nonhuman-adapted HIV-1 can be used in a non-transgenic, non-human host, especially when the HIV-1 genome is introduced into the host by a non-infective mechanism (e.g., electroporation, lipofection, co-transfection, etc.) and the endpoint being studied is a replication phenotype.

Transgenes and expression vectors can be constructed by any suitable method known in the art. It is often desirable to generate coding sequences for CD4, CCR5, CXCR4, and other human accessory proteins that aid viral infectivity by either PCR or RT-PCR amplification from a suitable human cell type (e.g., a T lymphocyte population) or by ligating or amplifying a set of overlapping synthetic oligonucleotides; publicly available sequence databases and the literature can be used to select the polynucleotide sequence(s) to encode the specific protein desired, including any mutations, consensus sequence, or mutation kernel desired by the practitioner. The coding sequence(s) are operably linked to a transcriptional regulatory sequence (e.g., T cell lineage-specific promoter/enhancer) and, if desired, an origin of replication (e.g., EBV ori) for episomal replication, or one or more flanking sequences having substantial sequence identity to a host chromosomal sequence to provide for homologous recombination and targeted integration of the transgene. In an embodiment, a transgene comprises a human CD4 minigene or a substantially complete human CD4 gene. Similar transgenes comprise a CCR5 and/or CXCR4 minigene or substantially complete gene. The transgenes can use the native gene transciptional regulatory sequences, or can employ an operably linked heterologous transcriptional regulatory sequence (e.g., a mouse CD4 promoter/enhancer, a CMV promoter/enhancer, a human T cell receptor gene promoter/enhancer, and the like). Often the transgene(s) and expression vector(s) will further comprise a reporter gene or a selectable marker gene (e.g., tk, neo) in a selection cassette to facilitate identification and enrichment of cells having the construct in functional form.

A wide variety of alternative transgene constructs suitable for expressing a human CD4, CCR5, and/or CXCR4 protein in non-human cells or animals will be apparent to the skilled artisan.

The transgene(s) and/or expression vectors are transferred into host cells, pluripotent embryonic stem cells, or embryonic pronuclei by a suitable method, such as for example lipofection, electroporation, microinjection, biolistics, viral transduction, calcium phosphate precipitation, or other method. Stable transfectant host cells can be prepared by art-known methods, as can transgenic non-human animals. Typically, germline transmission of the transgene(s) in the transgenic non-human animal is obtained and the resultant "founder mice" are bred by conventional breeding to generate the desired progeny (e.g., a huCD4 transgenic male can be bred with a huCCR5 transgenic female an offspring which are doubly transgenic –CD4/CCR5– are identified by Southern blot analysis of tail DNA). By obtaining the necessary collection of founder mice and interbreeding with screening for desired multiple transgenic genotypes, it is possible to generate a huCD4/huCCR5/huCXCR4 triple transgenic animal or any other desired combination of viral coreceptor proteins. Alternatively, a multiple transgenic can be obtained by a single transfection with multiple transgene species (linked or unlinked), or by sequential rounds of transfection and selection in ES cells to produce a pluripotent ES cell having the desired collection of transgene species.

Transgenic mice harboring germline copies of transgenes that encode and express human CD4, human CCR5, and human CXCR4 on lymphocytes or other cells (e.g., macrophages) are produced by these methods. These human viral coreceptor-bearing mice can be used to evolve an HIV-1 or HIV-2 viral genome to replicate efficiently in mouse cells and to produce infectious virions. Similar transgenic mice can be generated for other virus types; the mice bear a transgene that expresses one or more cell surface protein(s) that serve as a receptor for the virus of interest in a suitable cell type (e.g., lymphocyte, lung epithelial cells, nasopharyngeal cells, squamous epithelium, etc.). These transgenic mice have at least one cell type which is competent for infection by the virus of interest.

In a variation, a transgene can be used to alter the cell type(s) competent for infection by a virus. For example, a virus that is tropic for lymphocytes bearing a particular receptor protein (e.g., CD4) may infect non-lymphocytic cells (e.g., hepatocytes) that express CD4 under transcriptional modulation of a cell type-specific transcriptional regulatory sequence (e.g., an albumin promoter/enhancer region). In this manner, a transgenic non-human animal can be generated which has a "chimeric cell-type" having differentiated characteristics of multiple cell types (e.g., a CD4+ cell that is predominantly a hepatocyte). A wide variety of chimeric cell-types can be generated by the skilled artisan, both as transgenic non-human animals and as cultured cell strains or cell lines.

Transgenic host cells and/or transgenic non-human animals can support infectivity by and/or replication of a virus which does not naturally infect or replicate in the non-human animal and/or cell-type. In a broad aspect, a transgenic non-human host cell or organism is generated so as to express a xenogeneic protein, or plurality of protein species, that function(s) as a receptor for attachment or entry of a virus which has a natural host range that does not include the non-human host animal. Similarly, the transgenic non-human host cell or animal can comprise a transgene which directs expression of a receptor protein to cell types or developmental stages which do not normally express said receptor protein, thereby permitting the virus of interest to infect cell types outside the natural cell tropism of the virus.

Transgenic mice, rabbits, rats, and hamster cells with sequences from human chromosome 11 and/or 12 are especially preferred for propagation of HIV-1 and SHIV chimeric virus variants. Often, such transgenic non-human animals harbor a transgene, or multiple transgenes, encoding the expression of human CD4, human CCR5, and/or human CXCR4 in T lymphocytes or other cells. Transgenes encoding the expression of other human proteins can be similarly constructed and transgenic animals produced therefrom.

Bridge Cells and Bridge Organisms

In some cases, the desired non-human host cell or organism may be incapable of supporting replication of the virus in part because the desired host (e.g., mouse) is too distant phylogenetically from the natural host (e.g., human). The desired host may lack certain proteins necessary for replication of the virus, or may have equivalent host cell proteins which are too divergent from the natural host protein(s) in order to function effectively with the virus that has naturally evolved to function in its natural host. In such instances, it may be impossible to generate sparkplug variants by directly transferring shufflants of primary viral isolates into the divergent non-human host cells or organisms, and alternative strategies to adapt the virus to grow in the desired non-human host will need to be used.

One such strategy is to employ bridging host cells. Bridging host cells and organisms are sufficiently close phylogenetically to the natural host so as to support some detectable level of replication and/or infectivity of the virus or mutated and/or shuffled variants thereof. The bridging host often is intermediate in terms of phylogenetic distance between the natural host and the desired non-human host cell or organism. The capability of a bridging host to support virus replication can afford the practitioner with a suitable non-human host to support one or more rounds of shuffling and selection that can be used to evolve the pool of variant viruses away from rigid requirements for certain unique structural features of important host factors in the natural host. For example, an HIV-1 virus which does not replicate substantially in mouse cells even when the mouse cell is modified so as to support infection by the virus can be adapted by passaging in a suitable bridge host (such as non-human primate cells competent to support HIV-1 replication), typically in combination with recursive sequence shuffling and selection for the phenotype of enhanced replication in the bridging host, or in a plurality of bridging hosts (to select for broadened host range, rather than just changed host range). In many cases, the bridging host cell or organism is preferably transgenic for a transgene encoding a protein of the natural host which is important for substantial infectivity and/or replication of the virus (e.g., with respect to HIV-1 this can be a transgene expressing human CD4, CCR5, and/or CXCR4), particularly if the bridging host cell naturally lacks a cognate (or functional equivalent) of the protein. After one or more cycles of passaging and/or sequence shuffling and phenotype selection for virus variants that have evolved to grow in the bridging host, a non-transgenic bridging host cell or organism can often be used since the virus may become sufficiently adapted to the bridging host that the transgene-encoded protein is no longer needed for substantial infection and replication.

Chimeric Viruses

In order to employ bridge hosts, it can frequently be advantageous to modify the subject viral genome by incorporating one or more portions of a genome of a virus which is known to replicate in the bridge host and which of similar type to the subject viral genome (e.g., similar viral taxonomic classification), which can be called a "bridge virus". By incorporating a portion of a subject viral genome with a complementing portion of a bridge viral genome, a chimeric viral genome which is capable of replication in the bridge host is created.

Most frequently, it is useful to incorporate those portions of the bridge virus genome which are believed to encode functions that are substantially distinct between the subject viral genome and the bridge viral genome. These regions can be identified by highly divergent sequences between the two viral genomes, or can be regions containing genes known or believed to be important in controlling host range (e.g., surface glycoproteins such as the env gene of a retrovirus such as HIV-1). Often such critical genes are (1) viral glycoproteins, (2) polymerases or other transcription factors which must interact with host proteins or polynucleotides, or (3) viral non-coding sequences or secondary structures which must interact with host proteins (e.g., HIV-1 TAR hairpin sequences).

For example, if the subject virus is HIV-1 and the desired bridge host is a non-human primate, it is often advantageous to incorporate portions of a simian immunodeficiency virus (SIV) viral genome to create a chimeric HIV/SIV viral genome, termed a "SHIV" viral genome. Kuwata et al. (1996) AIDS 10: 1331 describe chimeric SHIV viruses composed of gag, pol, vif, vpx, nef, and LTR from SIV mac and vpr, tat, rev, vpu, and env of various HIV isolates. Chimeric viral genomes can be created by mixing predetermined portions of each genome on the basis of intelligent prediction of their functionality in the bridge host (as per Kuwata et al.), or the chimeric viral genomes can be created by shuffling all or portions of each viral genome with the other viral genome and selecting shufflants which possess the desired phenotype, which is typically enhanced replication in the bridge host. A variation employs chimeric oligonucleotides as PCR primers, wherein the chimeric primer has a first portion complementary to a HIV sequence and a second portion complementary to a SIV sequence to generate by PCR shuffled SHIV variants wherein the recombination junctions are principally the boundaries between the HIV sequence and the SIV sequence in the chimeric primers (see, FIG. 4). In this way, recombination joint location can be biased according to the practitioner's choice, which may be random, pseudorandom, or intelligent. The present invention thus provides for a collection of shuffled chimeric viral genomes which can then be subjected to selection for a desired phenotype.

Once a chimeric viral genome that replicates in the bridge host is established, forced evolution of the chimeric viral genome by the disclosed shuffling and selection method is employed. In order to yield an evolved virus which is most similar to the subject virus that is started with and incorporates the minimal sequence variation necessary to replicate in the bridge host, it is often desirable to backcross the selected chimeric viral genomes with the parent subject viral genome. The backcrossing is typically performed by shuffling with the parent subject viral genome and selection for retention of replication in the bridge host; frequently several iterative cycles of backcrossing are conducted. Alternatively, or in combination with the above, backcrossing to the parent subject viral genome can be done after the chimeric virus variants have been further adapted for growth in the final (i.e., non-bridge) host cell or organism.

With regard to adapting HIV-1 for growth in rodent cells, a chimeric SHIV genome or collection of SHIV genomes can be made by recombining one or more HIV-1genomes or portions thereof with a SIV mac genome or complementing portions thereof. The resultant SHIV genomes can be propagated and/or selected for growth in primate cells, such as macaque monkey cells (e.g., lymphocytes). Chimeric virus variants which replicate in the bridge cells are then selected (e.g., by harvesting virions or by recovering proviral DNA from cells in which a reporter system indicates a replication phenotype) and shuffled with each other and/or with the parental subject viral genome (e.g., HIV-1), and optionally mutagenized, and the shufflants are subjected to one or more subsequent rounds of phenotypic selection or screening.

For illustration and not limitation, a SHIV chimeric viral genome is generated and rescued as infectious virions. The SHIV virions are used to infect a monkey cell line that is susceptible to SIV infection, and which optionally may express a transgene encoding a human CD4, CCR5, and/or CXCR4 protein. The infected cells are incubated for a period of time suitable to permit replication, packaging, and egress of replication competent SHIV virus (e.g., an incubation period suitable for production of SIV virions following SIV infection). Replication competent SHIV genomes are obtained either as virions or, if a replication phenotype reporter is present, as proviral DNA from monkey cells which exhibit a replication phenotype. The recovered SHIV genomes are then shuffled with each other, and optionally with other HIV and/or SIV sequences, by a recursive sequence recombination method (e.g., fragmentation/reassembly format, template-switching, and the like) to produce shufflant SHIV genomes. Optionally, a mutagenic process (e.g., error-prone PCR, chemical mutagenesis, spiking with mutagenic oligonucleotides having random or pseudorandom sequence variation) is performed on the recovered SHIV genome sequences, either before, during, or after the shuffling step. The shufflants are rescued as infectious virions and a subsequent cycle of infection of the monkey cells is commenced. The cycle of (1) recovering virions or proviral DNA from cells in having a replication phenotype, (2) shuffling and optionally mutagenizing the sequences, and (3) rescuing infectious virions from shufflant genomes, is repeated until a desired level of replication in the host cells is obtained or until replication competence of the shufflants plateaus. After SHIV shufflants having the desired phenotype (e.g., improved replication in monkey cells) are obtained, they are used to infect mouse cells (e.g., mouse lymphocytes from a transgenic mouse expressing human CD4+ on peripheral T lymphocytes), and replicated virions or proviral DNA from cells having a replication phenotype are recovered so as to select for SHIV shufflants that are competent to replicate in mouse cells. The recovered SHIV genomes may then be subjected to additional round(s) of shuffling (optionally including mutagenesis) and selection to optimize replication in the mouse cells. When a desired level of replication is obtained in the mouse cells, the SHIV shufflants are backcrossed to (i.e., shuffled with) the parent HIV-1 viral genome or a collection of HIV-1 genomes, optionally including a mutagenesis process, and the resultant shufflants are rescued as infectious virions and used to infect mouse cells, and a recursive process of backcrossing to parent HIV-1 genome(s) and selection for replication in mouse cells will produce a chimeric HIV-1 viral genome that is predominantly derived from the parent HIV-1 genome and which contains a minimal degree of SIV sequences and/or mutations necessary to provide the desired level of replication in mouse cells.

Evolution of Component Sequences by Shuffling

The present method of shuffling can be used to optimize subgenomic components, such as structural genes, transcriptional regulatory regions, packaging sequences, replication sequences, subgenic functional domains, gene clusters, complete genomes, and the like), for a particular phenotype (e.g., functionality in a novel host species or cell type). The optimized components can then be shuffled into a replicable viral genome so as to transfer the phenotypic characteristic to the shuffled viral genome(s). This approach ("bottom-up") is particularly beneficial when it is unusually difficult to obtain a sparkplug variant for a desired phenotype simply from shuffling a collection of parental viral genomes which lack the phenotype.

Typically, a component sequence (or collection of related-sequence component sequences) is operably linked to a reporter polynucleotide so as to form a reporter construct whereby the reporter construct, when transferred into a suitable host cell or organism, will report whether or not the component sequence exhibits the desired phenotype. For example and not to limit the invention, a component sequence of HIV-1may be a transcriptional regulatory sequence (e.g., TAR, LTR, RRE, INS, CRS), a viral regulatory protein (e.g., tat, rev), a viral accessory protein (e.g., vif, vpr, vpu, vpx, nef), a viral glycoprotein (e.g., env), a viral polymerase (po1), viral capsid protein (e.g., gag), or the like.

In general, the component sequence to be optimized is most commonly a structural gene (i.e., a polynucleotide sequence that encodes a polypeptide gene product) or a transcriptional regulatory sequence (e.g., a viral promoter, a viral enhancer, a transcription terminator sequence, a secondary structure-forming sequence important for viral transcription and/or replication, and the like). The type of readout produced by a reporter construct is usually dependent upon the nature of the component to be optimized. Berkhout et al. (1997) Nucleic Acids Res. 25: 940 report a non-shuffling method for forced evolution of the TAR and polyA hairpins of the HIV-1 genome to stabilize or destabilize the capacity of HIV to replicate under different temperatures in the human T lymphocyte cell line SupT1; similar assay formats can be used to improve HIV-1transcriptional regulatory sequences by the present shuffling methods. In particular, it is desirable to optimize HIV-1 LTR, TAR, and RRE sequences for function in human cells, and these regulatory elements can be co-evolved with each other and/or co-evolved with Tat and/or Rev, respectively.

When the component to be optimized is a structural gene (e.g., tat, rev, env, pol) the readout is typically the improved function of the polypeptide encoded by the gene in the particular host cell or organism selected by the practitioner. However, other readouts for optimizing structural genes can also be used; for example and not limitation, the readout can be the level of expression of functional structural gene (e.g., to optimize codon usage in a host cell, to optimize translational efficiency or RNA processing efficiency, and the like). Improved function of a structural gene product is determined by a suitable assay system and selection of such assay system is dependent upon the nature of the specific gene product and can be selected by those skilled in the art. For example and not limitation, an assay to measure function of a viral gene product (e.g., pol) necessary for replication of a virus can comprise measuring the replication of a virus genome lacking said viral gene (e.g., pol) in a cell or organism in which the viral gene is encoded by and expressed from an expression cassette that is separate from the viral genome (e.g., an expression vector encoding pol); this variation can be termed "complementation in trans". A library of such expression cassettes encoding the component can be screened for functionality, and functional species selected (e.g., enriched for), and shuffled to produce a selected, shuffled library of shuffled component sequences that can be subjected to one or more additional rounds of functional selection and/or shuffling, so as to obtain one or more sequences encoding optimized component species (termed "optimized component sequences", or with specific reference to structural genes—"optimized structural gene component sequences").

When the component to be optimized is a transcriptional regulatory sequence, the readout is typically the improved transcription of a reporter polynucleotide (or the polypeptide encoded thereby) in the particular host cell or organism selected by the practitioner. The transcription of the reporter polynucleotide sequence can be detected by a method to detect transcription (e.g., PCR, LCR, hybridization with a labeled complementary sequence polynucleotide probe, inactivation of a conditionally lethal or screenable gene product by antisense hybridization, and the like), or by a method to detect an encoded gene product of the reporter polynucleotide (e.g., luciferase, β-galactosidase, HRP, GFP, and other suitable detectable reporter proteins). However, other readouts for optimizing transcriptional regulatory sequences can also be used; for example and not limitation, the readout can be the level of expression of a viral structural gene operably linked and transcriptionally modulated by the transcriptional regulatory sequence. Improved function of a transcriptional regulatory sequence is determined by a suitable assay system and selection of such assay system is dependent upon the nature of the specific gene product and can be selected by those skilled in the art. For example and not limitation, an assay to measure function of a viral transcriptional regulatory sequence (e.g., HIV LTR) necessary for viral gene expression and/or replication of a virus can comprise measuring the transcription rate of a reporter polynucleotide sequence operably linked to the transcriptional regulatory sequence in a cell or organism in which the viral transcriptional regulatory sequence is to be optimized. The reporter sequence is typically encoded by and expressed from an expression cassette that is separate from the viral genome (e.g., an expression vector in which the HIV LTR is positioned to drive transcription of a reporter sequence, such as a GFP-encoding sequence). A library of such expression cassettes encoding the transcriptional component can be screened for functionality, and functional species selected (e.g., enriched for), and shuffled to produce a selected, shuffled library of shuffled transcriptional component sequences that can be subjected to one or more additional rounds of functional selection and/or shuffling, so as to obtain one or more sequences encoding optimized transcriptional component species (which are a subgenus of optimized component sequences).

In variations, viral component sequences (whether structural genes or regulatory sequences) can be shuffled with other similar type components from related viruses (e.g., shuffling an LTR, or portion thereof, from HIV-1 with an LTR from simian immunodeficiency virus, SIV) or sequences from animal genomes having similar structure (e.g., greater than 50 percent sequence identity) and/or a known similar function (e.g., binding RNA pol II). In this manner, chimeric component sequences can be generated and those having a desired phenotypic property (e.g., modulating transcription of an operably linked sequence in a viral genome) can be selected for after one or more iterative rounds of sequence shuffling and selection.

With particular reference to HIV-1, components which naturally occur in overlapping reading frames in the retroviral genome can be optimized for function either separately (i.e., unconstrained by overlapping reading frames) or in native configuration. It will in some cases be possible to optimize multiple overlapping reading frames concomitantly, whereas in other cases it can be preferable to optimize a component separately and then incorporate the optimized sequence (or consensus sequence, if a collection of optimized sequences is obtained) into an overlapping reading frame configuration if that is desired or necessary for obtaining function or replication of the viral genome. However, in some instances optimized components will be used separately and need not be suitable for use in a replicable viral genome.

Exemplary Components

A component can be any subgenomic sequence comprising more than 10 consecutive nucleotides of a viral genome, typically comprising all or a substantial portion of a viral structural gene, transcriptional regulatory sequence, or replication control sequence. A component can also be any nonviral sequence of more than 10 consecutive nucleotides of a structural gene or transcriptional regulatory sequence from an animal cell genome (or mRNA pool), wherein said sequence encodes a protein involved in viral entry, viral transcription, viral replication, or viral egress, or wherein said sequence regulates transcription of a viral sequence (whether as in integrated provirus or as an episomally replicating viral genome).

To illustrate the invention and not to limit it, the following non-exhaustive list of viral components can be obtained from an HIV-1 genome: gag MA (P7), gag CA (p24), gag NC (p7,p6), protease (p15), reverse transcriptase/RNase H (p66,p51), integrase, Env (gp120/gp41), Tat (p16/p14), Rev (p19), Vif (p23), Vpr (10–15), Vpu (p16), Nef (p27/p25), Vpx (p12–16), Tev (p28),U3 sequence, U5 sequence, primer binding site sequence (PBS), polypurine tract (PPT), repeat region (R), long terminal repeat (LTR), minimal HIV promoter (NF-κB site, Sp1 sites, TATA box, transcription initiation site, Tat-responsive element (Tar), Rev-responsive element (RRE), splicing signals, and other open reading frames or transcriptional regulatory regions of the HIV genome. Similar components from SIV can often be used, and may supplement or replace the cognate components (or portions thereof) of the HIV-1 component.

To illustrate the invention and not to limit it, the following non-exhaustive list of nonviral (host cell) components can be obtained from a genome or mRNA pool of an animal cell and are believed important in HIV-1 entry, replication, or egress: cellular factors that bind to Tar or to Tat, factors encoded on human chromosome 12 that contribute to the transcriptional activity of Tat, CD4, CXCR4, CCR5, p561ck, NF-κB, Sp1, other coreceptors for HIV-1 attachment or entry, other host factors necessary for HIV-1 replication, and the like.

Although the examples provided reference HIV-1, those skilled in the art will be capable of selecting components from the particular virus type they desire to work with.

Reporter Constructs

A reporter construct comprises a component sequence in a form suitable to be transcribed or otherwise acted upon (e.g., bound by replication proteins) in a host cell. When the component sequence is derived from a structural gene, the component sequence is generally operably linked to a transcriptional regulatory sequence that promotes transcription of linked sequences in the host cell; the operably linked structural component and transcription sequence compose an expression cassette, which may be present on an episome (e.g., a plasmid, a viral genome, or an artificial chromosome), or may be integrated into a host chromosomal locus, or may be non-replicable and non-integrated. When the component sequence is a viral transcriptional regulatory sequence, the reporter construct is composed of a reporter gene generally operably linked to the viral transcriptional regulatory sequence; the operably linked reporter gene and viral transcription sequence compose an expression cassette, which may be present on an episome (e.g., a plasmid, a viral genome, or an artificial chromosome), or may be integrated into a host chromosomal locus, or may be non-replicable and non-integrated.

Koken et al. (1994) *Gene* 243, describe a promoter assay based on the transcriptional activator Tat of HIV-1; this type of assay can be used in modified format to screen for shuffled and/or mutated Tat sequences that can activate an HIV LTR-CAT reporter plasmid in a non-human cell (e.g., a mouse cell). White et al. (1995) *J. Cell Science* 108: 441 disclose a reporter system for real time analysis of transcriptional regulation of HIV promoters in mammalian cells using a reporter system comprising an HIV promoter operably linked to a luciferase reporter gene and transient transfection with an expression vector encoding HIV-1 Tat; such a system and variations thereof can be used to screen for shuffled Tat variants that are functional for HIV-1 promoter activation in non-human host cells.

Neuveut and Jeang (1996) *J. Virol.* 70: 5572 describe reporter assays for identifying trans activation of reporter plasmids by Tat. Suitably modified variations of the assays described, and similar trans-activation assays for other viral functions (e.g., Rev and RRE function) can be employed to evaluate transcription functionality of such components in non-human host cells.

Other variations of suitable reporter constructs will be apparent to those skilled in the art.

Shuffling and Selection

A plurality of species of a component are obtained, either by mutating a starting component specie to create a pool of mutated component species or by beginning with a plurality of component species (e.g., component "alleles" obtained from a plurality of virus isolates or even different virus types, such as HIV-1 and SIV), or other methods. The pool of component species can be either be incorporated into reporter constructs, introduced into host cells, and selected for a desired phenotype prior to the first round of shuffling, or may be initially shuffled before any selection is performed.

The plurality of component species is shuffled by a suitable sequence recombination method (e.g., by DNase fragmentation and PCR-based reconstitution of overlapped joints, or by any of the variety of suitable sequence shuffling methods described herein and elsewhere, and as is known in the art) to generate a library of sequence-recombined ("shuffled") component polynucleotides. The library of shuffled component sequences, typically in the form of reporter constructs, are introduced into host cells by a suitable method (e.g., transfection, electroporation, viral infection, lipofection, and the like) and the resultant pool of introduced shuffled reporter constructs are selected or screened for the desired functionality of the shuffled component sequences. Those library members (or progeny thereof) which comprise shuffled component sequences having a desired phenotype are recovered and the resultant pool of selected shuffled component sequences can be put through one or more additional cycles of recursive sequence shuffling to further optimize for the desired phenotype(s), or for additional phenotype(s). Mutagenesis and/or spiking can be used in conjunction with shuffling to further enhance the sequence diversity in one or more rounds of shuffling. Suitable mutagenesis methods are selected at the discretion of the practitioner, but for illustration and not limitation can include: site-directed mutagenesis by mutagenic oligonucleotide, error-prone PCR, chemical mutagenesis, mutagenic irradiation, propagation of polynucleotides in error-prone hosts, and the like.

Recovery of Selected Polynucleotide Sequences

A variety of selection and screening methods will be apparent to those skilled in the art, and will depend upon the particular phenotypic properties that are desired. The selected shuffled viral genome sequences can be recovered for further shuffling or for direct use by any applicable method, including but not limited to: recovery of virions from cells or extracellular medium (e.g., ascites, serum, spent cell culture medium), recovery of infectious particles (as pfu) from cells or extracellular medium, recovery of nucleic acids (or PCR-amplified copies thereof) from cells or medium, recovery of proviral sequences from host chromosomal DNA or PCR-amplified copies thereof, recovery of episome (e.g., expression vector) such as a plasmid, cosmid, viral vector, artificial chromosome, and the like, or other suitable recovery method known in the art.

Selected component sequences are typically recovered from the selected host cells having the desired phenotypic property (e.g., GFP expression) and can be obtained by harvesting the reporter construct itself (e.g., as an episome or an integrated chromosomal sequence), in which case it is frequently desirable to have unique restriction sites flanking the component sequence (or variable portions thereof) to be recovered and shuffled. Alternatively, any suitable art-known method, including RT-PCR or PCR, can be used to obtain the selected component sequence(s) for subsequent manipulation and shuffling.

Reconstitution of Shuffled Component Sequences

Although selected shuffled component sequences can be used for non-viral applications (e.g., using an optimized viral promoter in a non-viral gene therapy vector, and the like), a major use of such selected component sequences is the incorporation of the optimized component sequence into a replicable viral genome. An optimized component sequence can simply be cloned into the appropriate position on an existing viral genome, typically in place of the naturally-occurring component (e.g., an optimized Tat is used to replace the native Tat gene in HIV). Alternatively, an optimized component (or collection thereof) can be shuffled with a viral genome to produce viral genomes wherein the naturally-occurring component sequence is substantially replaced by one or more optimized component sequences. Another method is to simply recreate a viral genome de novo by splicing together optimized component sequences, and, if desired, native viral genomic sequences, to produce a synthetic viral genome from a plurality of optimized sequences. Such reconstituted viral genomes can be subjected to one or more rounds of selection and/or shuffling. Since components which are optimized in non-viral reporter systems may not be necessarily be concomitantly optimized for function in a viral genome, it can often be necessary to optimize the selected component(s) in a replicable viral genome (e.g., a wild-type viral genome) so that the component is optimized for function in the context of a replicable viral genome (i.e., a context-optimized component).

Rescue of Infectious Virus from Cloned Viral Sequences

One objective of the general method of shuffling viral genome sequences to produce shuffled sequences encoding a desired phenotype ultimately is the generation of virus variants that exhibit altered host range and/or cell tropism. In order to accomplish this expeditiously, it is sometimes preferable to employ a system to rescue infectious virus from cloned viral sequences. This may often be as simple as transfecting a viral genomic polynucleotide into a suitable host cell in which the viral genome can express necessary replicative functions, replicate the genomic polynucleotide, encapsidate the genomic polynucleotide and egress the cell (if appropriate). Sometimes it is necessary to utilize a helper cell line or helper virus to obtain replication and packaging. The helper cell line or helper virus typically provides a function in trans (e.g., viral polymerase) that facilitates an important step in viral replication and/or packaging. In the case of some viruses (e.g., negative strand RNA viruses), it can be necessary to form appropriate ribonucleoprotein complexes in order to support efficient replication of the viral genome in a cell (WO97/12032 and U.S. Pat. No. 5,166,057, for example). The skilled practitioner will select the rescue system appropriate for the particular virus that is to be shuffled.

With regard to HIV, there are a variety of suitable methods to recover infectious molecular clones, such as integrated or circularly permuted, non-integrated proviral forms, or subgenomic proviral sequences that can be reconstituted into full-length provirus (Gibbs et al. (1994) AIDS Res Hum Retroviruses 10: 607; Ghosh et al. (1993) Virology 194: 858; Li et al. (1991) J. Virol. 65: 3973; Fredriksson et al. (1991) Virology 181: 55). PCR can be used to construct infectious molecular clones of HIV-1 from full-length provirus. Infectious molecular clones of HIV can be obtained from the NIAID AIDS Research and Reference Reagent Program (Bethesda, Md.) or other publicly available source, or can be generated by the practitioner. Salminen et al. (1995) Virology 213: 80 disclose a method for recovering full-length HIV-1 provirus DNA from primary virus cultures by using PCR; this methodology can be used to recover HIV provirus from starting materials (e.g., HIV primary isolates) for subsequent shuffling, and to recover proviral DNA from selected HIV shufflants. Landau and Littman (1992) J. Virol. 66: 5110 describe a method for producing helper-free retrovirus (MLV) without using packaging cell lines; the system was used to alter cell tropism of a retrovirus by incorporating envelope glycoproteins from other viruses and mutant envelope glycoproteins.

Forced Evolution of HIV-1

HIV-1 replication, as defined by the production of infectious virions, requires the completion of a series of steps, each of which results from highly sophisticated interactions between viral and cellular factors. Early events culminate in the irreversible integration of the viral genome into the host cell chromosome, and late events exploit the host cellular transcriptional and translational machinery for the production of new viral particles.

Unfortunately, HIV-1 does not infect or replicate to any significant degree in convenient non-human model systems, such as mice. Patience et al. (1997) *Nature Medicine* 3: 282 reports pig endogenous retrovirus (PERV) can replicate in human cells. It would be desirable to generate HIV-1 variants which can replicate in mice or mouse cells.

The receptors which HIV-1 uses to get into cells are normally involved in the signaling that takes place between cells of the immune system. The molecules that bind to these receptors are called chemokines, and the receptors, in turn, are called chemokine receptors. The two main families of chemokines are the CCs and the CXCs, and likewise there are two parallel families of chemokine receptors, the CCRs and the CXCRs. In addition to using CD4 as a viral receptor, HIV-1 uses a receptor belonging to the first family, called CCR5, to gain entry to macrophages during the initial infection and during the many years of asymptomatic phase of the disease. Later, the virus mutates naturally in the infected human host, allowing it to gain entry into T cells through a member of the second receptor family, called CXCR4.

It is desirable to have a cost-effective non-human model of HIV disease and HIV viral replication. One approach to develop such as model is to make a transgenic mouse expressing a human CD4, human CCR5, and/or human CXCR4 on T lymphocytes and other cell types. However, even if they can infect such transgenic mouse cells, most or all HIV-1 isolates may not replicate efficiently in mouse cells. Thus it is desirable to make a "murine replicable HIV" by exploiting recursive sequence recombination of HIV-1 sequences and selection for mutant, shuffled, and/or chimeric HIV-1 sequences that have enhanced function and replicability in mouse cells. There are many alternative approaches to making such murine replicable HIV viral genomes by shuffling; these alternative variations will be apparent to the practitioner, and some specific variations are described herein for illustration and not limitation.

Generation of HIV Competent to Replicate in Mouse Cells

Viral genomes from HIV isolates can be shuffled with each other, with mutated HIV genomes, and/or with SIV or murine-tropic retroviral (MLV) genomes. The shufflants can be introduced into mouse cells expressing human CD4, human CCR5, and CXCR4 and selected for capability to replicate in the mouse cells and produce infectious virus that is capable if infecting such transgenic mouse cells. Once a desired level of replication of the evolved HIV shufflants is achieved, additional properties may be selected for, such as independence from human CD4 by performing additional cycles of recursive shuffling and selection on mouse cells expressing CCR5 and/or CXCR4 and lacking human CD4. In a variation, HIV-1 genome sequences are shuffled with a HIV-2 env gene, which is independent from CD4 for viral entry, to produce shufflants that encode an env protein that does not obligatorily require human CD4 for virus entry. Such env genes may be chimeras between a HIV-1 env and a HIV-2 env, or may be predominantly or exclusively HIV-2 env sequence, and possibly include additional mutations introduced as part of the recursive shuffling process.

Backcrossing to Specific Clades or Parent HIV Isolates

HIV-1 isolates can be grouped according to phylogenetic sequence similarities into categories referred to in the art as clades (Gao et al. (1994) *AIDS Research and Human Retroviruses* 10: 1359). Once a murine-replicable HIV-1 shufflant having a satisfactory capacity to replicate in mouse cells is obtained, recursive sequence recombination can be used to backcross the replicable HIV variant to one or more naturally-occurring HIV sequences, such as the wild-type parental backbone(s) from which the HIV variant was derived or to other HIV isolates. By performing multiple cycles of shuffling (backcrossing to a naturally-occurring HIV sequence and/or to a consensus sequence representing one or more clades), and selection for retention of the phenotype of replication in mouse cells, it will be possible to make murine-replicable variants of essentially any HIV isolate or clade representative sequence. In order to expedite the backcrossing process and reduce the number of cycles required, it is often preferred to employ a fine-grained shuffling process and to control the ratio of wild-type sequences to murine-replicable variant sequences to assure obtaining replicable shufflants having the maximum wild-type genetic content.

In these ways and variations thereof, it is possible to make murine-replicable shuffled HIV variants of any given virus isolate or clade, or even to make a representative pool of murine-replicable variants representing a plurality of clades. Sequencing of resultant murine-replicable variants and computer-assisted sequence comparison to starting viral genomes and backcrossed viral genomes will permit identification of particular mutations or mutation clusters that are responsible for replicability in mouse cells.

Multiclade Mixing

Recursive sequence shuffling can be used to generate collections of recombinant HIV variants that represent sequence diversity from a multiplicity of HIV clades. Frequently in drug development screening assays it may be necessary to screen each drug candidate against each individual clade to assure efficacy for all clades or to identify the molecular basis for resistance among resistant clades or isolates. The collection of shuffled variants representing multiple clades (or multiple drug resistant variants) can be used as a single benchmark to assay for drug resistance and rapidly identify the specific sequences responsible for the drug resistance. The pool of shuffled variants are used to infect a suitable cell line or non-human host animal and the drug is administered. Drug-resistant HIV variants will replicate and sensitive variants will not. By selecting for resistant variants and performing one or more recursive rounds of shuffling and selection, the variant HIV genomes obtained will represent drug-resistant genotypes which can be sequenced and/or backcrossed to parental sequences to identify which mutations are conserved through backcrossing and replication selection in the presence of the drug; such mutations are likely important for the drug-resistance phenotype.

Bridging in Primate Cells

As described supra, non-human primate cells (e.g., macaque monkey cells, spider monkey cells) and/or non-lymphocytic cells (e.g., NIH3T3 cells) can be used to bridge HIV virus evolution from a human T-lymphotropic virus to variant viruses having other host ranges and/or cell tropisms. Many non-human primate species can be used as a source of cells, which may be propagated in primary cell culture or immortalized by a variety of art-known methods. Alternatively, or in combination, with passaging the HIV virus (or mutagenized and/or shuffled variants thereof; including SHIV chimeras) in non-human primate cell cultures, it is also possible to passage these viruses in intact non-human primates, and recover the evolved virus variants from tissues or fluids of the primates and subject the recovered variants to recursive sequence shuffling and selection for replication in the non-human primate.

Virus Evolution in a Transgenic Mouse

HIV-1 shufflants can be introduced directly into transgenic mice harboring a transgene that encodes and expresses a human receptor for HIV (e.g., CD4, CCR5, CXCR4, etc.), and infective and replicable variants can be recovered from tissues (e.g., lymphoid tissues, peripheral blood lymphocytes) or fluids (e.g., serum, ascites) of the mouse. The mouse may also have a reservoir of human lymphoid tissue, such as a SCID/hu mouse with a human thymus/liver sandwich implanted under the kidney capsule. The reservoir of human lymphoid tissue can serve as a reservoir of human cells competent to replicate shuffled HIV variants such as may replicate poorly in mouse cells at early cycles of a forced evolution to modify host range to include mice. The human cell reservoir can amplify, by replication, the number of variant HIV viruses that can replicate in the mouse cells, as well as increase the background of HIV variants which are replicating solely in the human reservoir cells. However, since subsequent selections can be done with virus recovered from the animal and replicated in the absence of human cells, the increased background of human-specific HIV is not problematic.

Mixed Particle Infection (High MOI)

Superinfecting host cells at a high multiplicity of infection (MOI) can be used to advantage to increase the recombination between viral genomes. Preferably an MOI of 5 to 50 or greater is used to enhance recombination during the viral replication cycle in the cell.

Identification of Novel Human HIV Cofactors

Mouse cells non-permissive for HIV-1 infection can be used for expression screening of human cDNA libraries to identify cDNA sequences that encode proteins which confer permissivity to HIV-1 infection and/or replication. In an embodiment, a mouse lymphocytic cell line expressing a human CD4, a human CCR5, and a human CXCR4 protein is non-permissive for HIV-1 infection and substantial replication. The cell line contains a reporter system to report the presence of a replication phenotype (e.g., GFP operably linked to a Tat-dependent promoter). The cell line is transfected with an expression library encoding a plurality of human cDNAs which are operably linked to a constitutive transcriptional regulatory sequence (e.g., CMV promoter) and cells which express the reporter indicating infection and a replication phenotype are selected and the cDNA expression vector species contained therein are evaluated for the ability to reproducibly confer enhanced infection and replication of HIV in the transgenic mouse cells. Selected cDNA species are identified as HIV cofactors and constitute targets for development of novel antiviral drugs. The selected cDNA sequences can also be incorporated into a transgene to generate mouse cells (or transgenic mice) having enhanced permissivity for HIV infection and replication.

Site-Specific Recombination and Amplification

In order to bias recombination to specific regions of the viral genome sequence, it is possible to engineer into the viral genome sequence one or more site-specific recombination sites (e.g., loxP, frt). By employing a complementing site-specific recombinase (e.g, CRE or FLP recombinase), it is possible to create recombination hotspots to bias the shuffling process. The site-specific recombination can be done in vitro, or, by employing a transgenic cell or animal expressing the recombinase, can be done in vivo. Furthermore, a tandemly repeated array of viral genomes or subgenomic sequences containing site-specific recombination sequences (e.g., such as a transgene containing tandem repeats of a provirus) can be used to obtain intra-array recombination to enhance diversity.

Often, it is desirable to amplify the viral genome sequence (s) to increase the amount of recombinogenic viral genome sequence present. In an embodiment, a transgene containing tandemly repeated arrays of a proviral genome is operably linked to an expression cassette encoding a selectable marker that can be amplified (e.g., DHFR). Selection for amplification (e.g., increasing concentrations of MTX) is applied to the transgenic cells to expand the number of proviral genomic sequences present. After (or concomitant with) amplification, a site-specific recombinase is activated, either transcriptionally or allosterically (e.g., by ligand-induced activation of an expressed chimeric protein comprising the ligand-binding domain of a steroid receptor and the site-specific recombinase), so as to produce site-specific recombination among the proviral genome sequences and thereby effect shuffling and the production of shuffled viral genome variants.

Combinations

Combinations of the shuffling and selection strategies disclosed herein can be used.

Defective HIV Variants Having Enhanced Safety

Once shuffled, HIV variants that are capable of substantial replication in mice are established, one or more viral genomic sequence(s) necessary for the altered host range and/or tropism and that function in trans can be deleted from the shuffled and adapted viral genome and provided in trans in the host cell or animal (e.g., as a transgene expression cassette), so that the host provides the helper function that complements the replication of the virus, but the resultant virus that is produced is non-infective for organisms that lack the helper function. In this way, a model system of a transgenic animal providing an internal helper function can be used in conjunction with a replication-deficient HIV virus to develop antiviral drugs and study HIV disease without fear that infectious, replication-competent virus will be produced and infect lab workers or escape into human or animal populations.

Attenuation Phenotypes

Shuffling can be used to generate virus variants having attenuated phenotypes, such as reduced pathogenicity and/or virulence. One general type of such attenuated variants are the temperature-sensitive and/or cold-adapted mutants. In this aspect, selection of shuffled variants would select for shuffled viral genomes that replicate efficiently at reduced (or elevated) temperature. Other attenuation types can also be selected for.

Other Phenotypes

The present method can be used to generate variant viruses having a wide variety of altered phenotypes. Illustrative examples not intended to limit the scope of the invention are: (1) capability to replicate in a non-permissive cell, (2) host range and/or cell tropism distinct from naturally-occurring wild-type virus, (3) improved virus titer (e.g., virulence), (4) decreased pathogenicity and capacity to produce disease, (5) modified infectivity, (6) improved packaging capacity, (7) improved physical/chemical stability of viral particles, (8) improved intracellular stability, (9) improved expression of one or more viral genes, (10) modified chromosomal integration, (11) altered tissue specificity and capability to infect preferentially specific organs which the natural virus does not substantially infect, (12) reduced immunogenicity or virus or viral protein in a host (e.g., a human), (13) improved immunogenicity of virus or viral protein in a host (e.g., human), (14) improved function as a biological adjuvant (e.g., to co-express a viral-encoded human cytokine), (15) improved function as a therapeutic (e.g., capacity to induce a general antiviral host response—such as interferon production), and others phenotypes apparent to the practitioner.

Adapted Virus:Host System

One use of the present technology is to generate a non-human animal (e.g., a transgenic mouse) that can support replication of a shuffled viral genome that has been adapted for infection and/or replication in the animal (or isolated cells therefrom); such a transgenic mouse-adapted virus system has many commercial uses, including screening for agents that inhibit viral replication, entry, egress, or other aspects of a viral life cycle. Furthermore, these systems can be marketed to research institutions and pharmaceutical organizations as commercial research tools (e.g., like restriction enzymes or oncogenically susceptible mice like p53 knockouts).

Whole Genome Shuffling

In one embodiment, the selection methods herein are utilized in a "whole genome shuffling" format. An extensive guide to the many forms of whole genome shuffling is found in the pioneering application to the inventors and their co-workers entitled "Evolution of Whole Cells and Organisms by Recursive Sequence Recombination, " filed Jul. 15, 1998 by del Cardayre et al. (U.S. Ser. No. 09/116,188).

In brief, whole genome shuffling makes no presuppositions at all regarding what nucleic acids may confer a desired property. Instead, entire genomes (e.g., from a genomic library, or isolated from an organism) are shuffled in cells and selection protocols applied to the cells. As applied to the present invention, entire viral (or host cellular) genomes are optionally shuffled to produce viruses with a desired tropism, or cells which will support growth of selected viruses.

Codon Modification Shuffling

Procedures for codon modification shuffling procedures are described in detail in SHUFFLING OF CODON ALTERED GENES, Phillip A. Patten and Willem P. C. Stemmer, Ser. No. 60/102,362, filed Sep. 29, 1998. In brief, by synthesizing nucleic acids in which the codons which encode polypeptides are altered, it is possible to access a completely different mutational cloud upon subsequent mutation of the nucleic acid. This increases the sequence diversity of the starting nucleic acids for shuffling protocols, which alters the rate and results of forced evolution procedures. Codon modification procedures can be used to modify any viral nucleic acid herein, e.g., prior to performing DNA shuffling. This can have the benefit of allowing the virus to adapt to a host cell's codon selection, e.g., prior to shuffling.

Use of RecA

The frequency of homologous recombination between nucleic acids can be increased by coating the nucleic acids with a recombinogenic protein, e.g., before or after introduction into cells. See Pati et al., *Molecular Biology of Cancer* 1, 1 (1996); Sena & Zarling, *Nature Genetics* 3, 365 (1996); Revet et al., *J Mol. Biol.* 232, 779–791 (1993); Kowalczkowski & Zarling in *Gene Targeting* (CRC 1995), Ch. 7. The recombinogenic protein promotes homologous pairing and/or strand exchange. The best characterized recA protein is from *E. coli* and is available from Pharmacia (Piscataway, N.J.). In addition to the wild-type protein, a number of mutant recA-like proteins have been identified (e.g., recA803). Further, many organisms have recA-like recombinases with strand-transfer activities (e.g., Ogawa et al., *Cold Spring Harbor Symposium on Quantitative Biology* 18, 567–576 (1993); Johnson & Symington, *Mol. Cell. Biol.* 15, 4843–4850 (1995); Fugisawa et al., *Nuc. Acids Res.* 13, 7473 (1985); Hsieh et al., *Cell* 44, 885 (1986); Hsieh et al., *J. Biol. Chem.* 264, 5089 (1989); Fishel et al., *Proc. Natl. Acad. Sci. USA* 85, 3683 (1988); Cassuto et al., *Mol. Gen. Genet.* 208, 10 (1987); Ganea et al., *Mol. Cell Biol.* 7, 3124 (1987); Moore et al., *J. Biol. Chem.* 19, 11108 (1990); Keene et al., *Nucl. Acids Res.* 12, 3057 (1984); Kimiec, *Cold Spring Harbor Symp.* 48, 675 (1984); Kimiec, *Cell* 44, 545 (1986); Kolodner et al., *Proc. Natl. Acad. Sci. USA* 84, 5560 (1987); Sugino et al., *Proc. Natl. Acad. Sci. USA* 85, 3683 (1985); Halbrook et al., *J. Biol. Chem.* 264, 21403 (1989); Eisen et al., *Proc. Natl. Acad. Sci. USA* 85, 7481 (1988); McCarthy et al., *Proc. Natl. Acad. Sci. USA* 85, 5854 (1988); Lowenhaupt et al., *J. Biol. Chem.* 264, 20568 (1989). Examples of such recombinase proteins include recA, recA803, uvsX, (Roca, A. I., *Crit. Rev. Biochem. Molec. Biol.* 25, 415 (1990)), sep1 (Kolodner et al., *Proc. Natl. Acad. Sci. (U.S.A.)* 84, 5560 (1987); Tishkoff et al., *Molec. Cell. Biol.* 11, 2593), RuvC (Dunderdale et al., *Nature* 354, 506 (1991)), DST2, KEM1, XRN1 (Dykstra et al., *Molec. Cell. Biol.* 11, 2583 (1991)), STP/DST1 (Clark et al., *Molec. Cell. Biol.* 11, 2576 (1991)), HPP-1 (Moore et al., *Proc. Natl. Acad. Sci. (U.S.A.)* 88, 9067 (1991)), other eukaryotic recombinases (Bishop et al., *Cell* 69, 439 (1992); Shinohara et al., *Cell* 69, 457. recA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA to be shuffled and can form complexes with both single-stranded and double-stranded DNA in prokaryotic and eukaryotic cells. recA mediated techniques are also found in WO/93122443.

Before contacting with recA or other recombinase, fragments are optionally denatured, e.g., by heat-treatment. recA protein is then added at a concentration of about 1–10 $\mu$M. After incubation, the recA-coated single-stranded DNA is introduced into recipient cells by conventional methods, such as chemical transformation or electroporation. In whole cell shuffling techniques, the fragments undergo homologous recombination with cognate endogenous genes. Because of the increased frequency of recombination due to recombinase coating, the fragments need not be introduced as components of vectors.

Fragments are sometimes coated with other nucleic acid binding proteins that promote recombination, protect nucleic acids from degradation, or target nucleic acids to the nucleus. Examples of such proteins includes Agrobacterium virE2 (Durrenberger et al., *Proc. Natl. Acad. Sci. USA* 86, 9154–9158 (1989)). Alternatively, recipient strains can be deficient in recD activity. Single stranded ends can also be generated by 3'–5' exonuclease activity or restriction enzymes producing 5' overhangs.

The broad scope of this invention is best understood with reference to the following examples, which are not intended to limit the invention in any manner. The following examples are offered by way of illustration, not by way of limitation.

EXPERIMENTAL EXAMPLES

The following examples are illustrative and not limiting. One of skill will realize a variety of parameters which can be changed to achieve essentially the same results.

Example 1

Evolution of Novel Phenotypes in HIV by Intra- and Interclade Shuffling

The diversity of HIV sequences in natural and laboratory isolates is utilized to generate a library of recombinant HIV sequences from which strains with desired characteristics are selected. These include novel tropisms on cells from species normally refractory to HIV infection, the use of alternate receptors to enter cells and improved replication kinetics.

Method

Sources of HIV Sequences

Subgenomic sequences of various regions of the HIV genome are obtained from: 1) available molecular clones of different HIV strains; 2) PCR using consensus or degenerate primers from genomic DNA of chronically infected tissue culture cells; 3) RT-PCR of HIV particles from supernatants of chronically infected cells or patient fluids.

A wide collection of such sequences are collected from multiple clades of HIV. These subgenomic HIV sequences are cloned into bacterial plasmids that will be used as templates.

DNA Shuffling

Shuffling is performed either by: 1) Directly performing circular shuffling of plasmids carrying analogous regions of the HIV genome from different isolates; or 2) Pooling PCR fragments amplified from plasmids carrying analogous regions of the HIV from different isolates genome and performing linear shuffling.

Shuffled material is amplified using primers incorporating specific restriction sites. These restriction sites enable the shuffled amplified fragments to be functionally cloned into the backbone of an infectious HIV clone (pNL4.3) containing the remainder of the HIV genome as in the case of MLV full length reconstruction where the Moloney MLV clone provided the backbone (see infra). This reconstitutes a full length HIV clone. A library of recombinant shuffled HIV clones are thus constructed. The library is propagated and amplified in *E. coli* to obtain DNA for transfection.

Tissue Culture

The library is initially transfected into cells permissive for HIV growth such as CEM. Supernatants from this transfection are then used to infect target cells (mouse, CD4–etc). The target cells are passaged for some time (2–3 weeks) to allow the spread of any viable clones. Also, a mixture of a minority of permissive cells can be cocultured with a large excess of target cells to allow a basal level of replication of HIV strains. This allows any defective, but viable, strain of evolved HIV to slowly spread and also to allow further recombination of HIV to take place at a basal level.

Monitoring of Virus Spread

This is achieved with assaying for reverse transcriptase activity in the supernatant, release of HIV antigens by ELISA and Westerns and the use of reporter cell lines containing integrated reporter genes (GFP, β-gal) under the control of the HIV LTR. PCR of genomic DNA from infected target cells is also performed. Recovery of Subgenomic Sequences When virus spread is detected in a culture of target cells after several passages, PCR of genomic DNA from these cells is performed to recover the HIV subgenomic sequences.

Sequences from independent cultures are pooled and subjected to further rounds of shuffling and selection.

Example 2

Shuffling of Retrovial Genomes of Murine Leukemia Viruses

Multiple natural strains of MLVs are shuffled to evolve new strains that have novel phenotypes not possessed by any of the parental strains. Subgenomic fragments of the different parental MLV genomes are shuffled and subcloned into an infectious backbone based on the Moloney MLV genome. Libraries of potentially infectious clones are created and screened for novel phenotypes. The initial phenotype screened for is the ability of shuffled clones to infect and grow on several hamster and murine embryonal carcinoma (EC) cell lines that are refractory to infection by any of the parental lines.

This example demonstrates the effectiveness of DNA shuffling of viral genomes to evolve retroviruses to have desired characteristics useful in gene delivery applications. These characteristics will include the ability to infect: a) specific cell types efficiently e.g., hematopoietic cells; b) non-replicating cells; c) more stable retroviral particles; d) higher titers; and e) site specific integration of delivered genes.

It also demonstrates the feasibility of building a general library from which different novel phenotypes affecting different parts of the viral life cycle can be selected.

MLV Strains

Without being exhaustive, all or subsets of MLV strains listed below are used for family shuffling.

| Strain/isolate | Class |
|---|---|
| 1) Friend | Eco |
| 2) Rauscher | Eco |
| 3) 292ECl. 15 | Eco |
| 4) 292A | Ampho |
| 5) Mo- Ampho | Ampho |
| 6) Moloney | Eco |
| 7) AKR | Xeno?MCF |
| 8) Gross | Eco |
| 9) Balb V2/BC 169 | Endo/Xeno |
| 10) Balb V1/BC 194 | Endo/Xeno |
| 11) Balb V2/BC 177 | Endo/Xeno |
| 12) AT 124 | Xeno |
| 13) NZB cl 15. | Xeno |
| 14) AKR 13 | MCF |
| 15) AKR 247 | MCFSource |

Proviral DNA

The Moloney MLV was obtained as an infectious proviral clone. All the other strains were obtained as biological clones or preparations and used to infect Mus Dunni cells. Genomic DNA from infected Mus Dunni cells was used as template to PCR subgenomic fragments of the various MLV strains. These subgenomic fragments are thus cloned into bacterial Bluescript plasmids.

Shuffling

A 3 kb region encompassing the 3' 500 bp of pol, the entire env and 3' LTR constitute the subgenomic fragment to be shuffled. The DNA used for shuffling is derived from in vitro PCR using plasmid clones as templates. Mixtures of PCR amplified fragments from all or subsets of the 15 strains are used in the shuffling process. The fragments are DNAse digested into 400–1.5 kb size range. These are reassembled by 30–45 cycles of annealing and extension without primers. The assembled mixture is then amplified with PCR. These shuffled fragments are then subcloned into the Moloney backbone and transformed into *E. coli* libraries. Other subgenomic regions, e.g., the gag region may also be shuffled for the selection of specific phenotypes (e.g., infection of non-replicating cells). The whole genome, ~9 kb, may also be shuffled either in one large segment or as smaller segments separately which are later linked back together into the full length genome.

Screening

The plasmid libraries are transfected into cells permissive for retroviral replication (at present 293 human embryonic kidney cell line) for the initial production of viral particles. Supernatants from these transfections are transferred to the target cells for selection for the ability to infect and replicate. Serial passages of these exposed target cells will be performed to allow the infection to spread. Marker rescue, reverse transcriptase, and genomic PCR assays are used to monitor whether a productive infection has taken place.

Assays

Marker Rescue

Supernatants are passaged through cells containing an integrated β-gal/Neomycin resistance vector. These will then be used to infect target cells which will then be assayed for the expression of the marker(s).

Reverse Transcriptase

Supernatants are treated to precipitate and lyse retroviral particles. The extract is then subjected to an ELISA based assay for reverse transcriptase activity. The lysis treatment (detergent) is expected to inactivate any infectious particles.

Genomic DNA PCR Cells putatively infected with retrovirus are harvested. A detergent lysis, salt precipitation and alcohol precipitation procedure is used to extract genomic DNA and inactivate any infectious material. This DNA is then used as template for the PCR of subgenomic fragments of proviral DNA. The presence of a spreading infection on the target cells is indicated by the above assays. Genomic sequences of the optimized virus is recovered either by PCR amplifying the cellular genomic DNA of the infected cells or by RT-PCR of retroviral particles recovered from the supernatant of the infected cells.

Secondary Shuffling

Subsequent rounds of shuffling are performed on recovered subgenomic fragments similarly to the first round.

Characterization of Desired MLV Clones

Recovered infectious MLV clones with the desired phenotypes are characterized by traditional techniques such as titers, Westerns for viral antigens, reverse transcriptase activity, tropism, mapping and sequencing.

Cell Lines Used

| Name | Description |
| --- | --- |
| 3T3 | Murine embryo |
| SC-1 | Feral Mice |
| Mus Dunni IIIc | Feral mice tail fibroblast |
| P19 | Mouse embryonal carcinoma |
| F9 | Mouse embryonal carcinoma |
| Mv-1 Lu | Mink Lung |
| 293 | Human kidney embryonic |
| CHO-K1 | Chinese Hamster Ovary |
| BHK-21 | Baby Hamster kidney (Syrian) |
| Don CHL | Hamster |
| PA317 | Retroviral packaging; amphotropic/3T3 |

Example 3

Creation of Adenovirus Host Range Mutants by DNA Shuffling

Tissue tropism is a problem that exists in most of the viral vectors. For example, retroviruses do not target specific cells and only integrate into dividing cells. Ad2 and Ad5 infect most human cells but do not infect or propagate in lymphocytes, keratinocytes, and hematological malignant cells. The host range determinants of Ad infection include viral and host factors. Cells must have Ad receptors (still unknown) and integrins in order to be permissive for Ad infection, and the Ad viruses must have appropriate fibers, penton base, and early genes in order to infect and propagate in the cells. It has been previously shown that by infecting nonpermissive cells (Vero) with a high MOI of Ad12 and continuously passaging the infected cells for many weeks, an adapted Ad12 mutant with altered host range (grows well in Vero) can be isolated. By shuffling the viral DNA, this adaptation process is facilitated, and new host range mutants are isolated. Human adenovirus group C propagate poorly in human lymphoma and myeloma cell lines, therefore, these cell lines can be used as host targets in the isolation of host range mutants. Ad viruses which can propagate efficiently in hematological malignant cells are evolved by recursive sequence shuffling.

Method

Shuffling Group C Ad Viruses (Serotypes 1, 2, 5, and 6).

Group C adenoviruses were chosen because that they are not oncogenic in animal models. The genomes of these viruses also share more than 90% identity, allowing more efficient DNA shuffling (recombination) in vitro. The entire genomic sequence of Ad5 is shuffled using error prone PCR. Ad1, Ad2, and Ad6 sequence fragments are spiked in to increase diversity.

Testing of Wild Type Ad Infectivity in Leukemia, Lymphoma, and Myeloma Cell Lines Marginal permissive cell lines are chosen as the host targets. Complete nonpermissiveness may indicate lack of the cellular receptor or integrins, and may thus cause difficulties in creating a mutant adenovirus that can compensate these shortcomings.

Infect Cell Lines with Ad Mutants Created by Shuffling, Screen for Mutants which give Higher Titers.

Infectivity of Ad mutants in target cell lines is evaluated by isolating the viruses at different time points after infection and determining their titer by plaque assay on a permissive cell line. Mutants with increased infectivity are pooled and subjected to recursive cycles of shuffling and screening to obtain mutants with greatly enhanced infectivity.

Characterizations of the Isolated Host Range Mutants

Molecular characterizations, such as mapping, sequencing, analyses of viral DNA replication, transcription, and protein synthesis, is performed. Ad viral genomes encoding altered host range and cell tropism are obtained.

Example 4

Evolution of Hepatitis B Viral Genome for Human Hepatocyte Tropism

DNA shuffling and selection for replication is used to evolve HBV viral genomes for encoding the phenotype of infection and propagation in human hepatic tissue culture cells and in woodchucks. These systems will be especially useful for rapid screening and testing of new drugs.

Hepatitis B virus (HBV) infection is the major risk factor in the development of chronic hepatitis and hepatocellular carcinoma (HCC). As much as 15% of the population is chronically infected in areas where this virus is highly prevalent such as in eastern Asia and sub-Saharan Africa. A large scale epidemiology study has shown that approximately 40% of the male HBV carriers will eventually die of HCC.

None of the established cell lines is susceptible to infection of HBV derived from serum, or produced by HBV-producing cell lines. HBV can only infect primary human hepatocytes and the hepatocytes of chimpanzee. Thus, chimpanzee, an endangered species which is expensive and allows only limited experimentation, represents the only available animal model. There is a woodchuck hepatitis virus (WHV) which is homologous to HBV and causes chronic hepatitis and HCC in the woodchucks. However, the pathology of WHV infection in woodchucks is somewhat different from that of HBV in human or chimpanzee. Thus, the availability of permissive cell lines and small animal models, in which HBV can infect and propagate, would be valuable for the testing of therapeutic vaccines and drugs.

The HBV replication cycle involves multiple steps, including virus attachment and entry, formation of covalently closed circular DNA, transcription, RNA packaging and reverse transcription, (+) strand synthesis, and viral assembly and release. Many of these steps involve interactions between HBV genome/gene products and those of the host cell. Therefore, the inability of HBV to infect and replicate in culturable human cells and in woodchuck may be caused by multiple blocks, and the number of mutations required to generate a mutant capable of replication in nonpermissive cells can be large. This possibility is also suggested by the fact that, despite intensive research in this field, so far no such a host range HBV mutant has been isolated. DNA shuffling is uniquely suited to obtaining novel mutants with complex genetic compositions which require multiple combinations of mutations or existing alleles. Therefore, DNA shuffling may be a promising approach to solving the problem of evolving HBV to grow in human hepatic cell lines and in woodchucks.

Method

HBV has a genome size of 3.2 kb, which is easily and effectively shuffled using an in vitro shuffling format. In addition, numerous natural variants of HBV and WHV, whose genomes are highly homologous, are obtained and shuffled to achieve a library of increased diversity. This library is transfected into target cells. Viral infection and propagation are monitored by reverse transcriptase assay, quantitative PCR of the viral genome, and the accumulation of viral surface or core antigens. For in vivo selection in woodchucks, the shuffled HBV library is delivered to liver cells by adenovirus, AAV, or nonviral vectors. The propagation of mutant HBV in liver cells is monitored by the presence of HBV DNA and/or surface or core antigens in the serum, and by viral antigens and pathogenesis in the liver. Genomic DNA of positive viral clones is obtained by PCR from the medium supernatant of the tissue culture cells, or from serum of the woodchucks. Selected pools of mutant HBV DNA is used for recursive shuffling/selection cycles to obtain mutants with improved phenotypes. The evolved mutant virus is backcrossed with wild type HBV to eliminate unnecessary and silent mutations and to retain the replication and pathogenic properties of HBV.

Example 5

Directed Evolution of a New Tropism in Retrovirus (MLV) by DNA Suffling

DNA shuffling was used to evolve a new tropism in ecotropic murine leukemia virus (MLV). A library of shuffled ecotropic envelopes cloned into full-length proviral genomes was selected for the ability to infect CHO KI cells. A dominant clone rapidly emerged during selection containing an envelope that was a clear recombinant between three of the parental sequences. This recombinant envelope conferred infectivity for CHO K1 cells through a novel mechanism. Our data show that this recombinant envelope was formed as a direct result of the DNA shuffling process.

Current gene transfer vectors suffer from limitations that restrict their clinical efficacy. Efforts to improve viral vectors have focused on rationally designed modifications of viral components. Such approaches demand detailed knowledge and understanding of the limiting mechanisms. This knowledge is often incomplete and as a result, these approaches have achieved only limited successes. For example, attempts to develop targetable retroviral vectors by incorporating ligand binding domains into the envelope result in vectors that can bind specifically but are inefficient at entry (Kasahara, N., Dozy, A. M. & Kan, Y. W. Science 266, 1373–1375 (1994)). On the other hand, viruses and particularly retroviruses are notorious for their ability to evolve their way around biological blocks. This process has been utilized in many studies to evolve viruses with new phenotypes such as expanded tropism (Vahlenkamp, T. W. et al. Journal of Virology 71, 7132–7135 (1997) Taplitz, R. A. & Coffin, J. M. Journal of Virology 71, 7814–7819 (1997), drug resistance (Balzarini, J. et al. Journal of Virology 67, 5353–5359 (1993) Dianzani, F. et al. Antiviral Chem. Chemother. 4, 329–333 (1993) and promoter activity (Barklis, e., Richard, M. & Jaenisch, R. Cell 47, 391–399 (1986)). Components of evolved viral variants, for example LTR elements have been incorporated into improved viral vectors (Robbins, P. B. et al. Journal of Virology 71, 9466–9474 (1997)).

Adaptation of viruses to new host cells typically requires prolonged passaging and selection. This is due to the necessity for the continuous generation and selection of variants before an effective solution is found. Usually this involves only a few mutations. Biological adaptations that require constellations of mutations or novel combinations of functional domains may not be achieved without long periods of replication and frequent extinctions. In this example, we demonstrate that DNA shuffling can dramatically accelerate viral evolution towards desired phenotypes by enhancing recombinatorial processes in vitro.

In DNA shuffling (e.g., Stemmer, P. C. Nature 370, 389–391 (1994)), similar input sequences are first randomly fragmented. The fragments are then reassembled through multiple cycles of self-priming polymerase chain reaction. Because of the complementary overlapping ends, a fragment from one parental sequence can prime off a template from another parental sequence. DNA shuffling thus generates a population of recombinant sequences which is then screened or selected for improved phenotypes. The process can be applied recursively to independently selected sequences to recombine useful variations, often with synergistic effects. The diversity of the input parental sequences can be generated by mutagenic processes or, more effectively, by using several natural occurring sequences (Crameri, A., Raillard, S. -A., Bermudez, E. & Stemmer, W. P. C. DNA Nature 391, 288–291 (1998)) (natural diversity). DNA shuffling thus accelerates natural processes of evolution by the rapid and efficient generation of diversity through errors and recombination, followed by selection. Many single and multigene systems have been dramatically improved using this process (Patten, P. A., Howard, R. J. & Stemmer, W., P. C. Current Opinion in Biotechnology 8, 724–733 (1997)). Here we applied the shuffling process for the directed evolution of a new tropism in MLV. Using envelope sequences from parental MLV strains that were non-infectious for CHO K1 (Chinese Hamster Ovary) cells, we were able to rapidly evolve a chimeric envelope that conferred infectivity for these cells. This chimeric sequence represents a novel solution that is different from any known MLV strains that can infect CHO K1. Our results underscore the ability of DNA shuffling in viral systems to find novel solutions where understanding of the biological limitations is incomplete.

Parental MLV Clones

Six ecotropic MLV envelope sequences were used as the parental sequences. These were of Moloney, 292E and four Friend (#2,7,9,21) clones. The Moloney clone was obtained as the infectious proviral clone pNCA. This plasmid was modified to have a unique NotI site just downstream of the 3' LTR. A 3.2 kb fragment encompassing about 0.5 kb of pol, the entire env and 3' LTR was excised and replaced with analogous fragments from the other strains. Friend and 292E sequences were amplified with appropriate primers from infected Mus Dunni genomic DNA to generate the analogous fragments. Thus, infectious MLV clones were reconstituted, consisting of 5' Moloney sequences and 3' sequences from the other strains. Table 1 shows the infectious activities of the six parental clones after transfection into 293 cells containing an integrated G418 resistance vector (293/G1). All six parental viruses did not infect CHO K1 cells and had clearly different 'infectious profiles' on the various cell types. The four Friend clones were isolated from the same Friend biological complex and their different infectivities reflect the presence of multiple species in the original stock. This was borne out by subsequent sequencing of the envelope genes which confirmed that the Friend clones were related but distinct to one another. Friend 2,7 and 9 are more closely related and may have resulted from the sequential accumulation of mutations while Friend 21 is further diverged.

Library Construction and Characterization

Sequences between the SfiI and NotI sites of the parental clones were amplified and shuffled together. Recombinant sequences were then cloned back into the backbone vector to generate a library of approximately $1 \times 10^6$. Several independent clones were picked and analyzed by restriction analysis as described. Eight out of 24 clones exhibited patterns different from any of the parents. This represents a lower limit for recombination frequency as many other nucleotide changes may not be detected. To assess the viability of the library, 5 pools of 4 clones each were transfected into 293/G1 cells. The viral supernatants were tested for the ability to transduce G418 resistance into 3T3 and Mus Dunni cells. Four of the 5 pools were able to strongly transduce G418 resistance into at least one of the cell types. Thus, if each positive pool only had one infectious clone, this would give a frequency of 20% (4/20) which represents a lower limit for the viability of the library.

Passaging of Library/Selection

Figure 7:
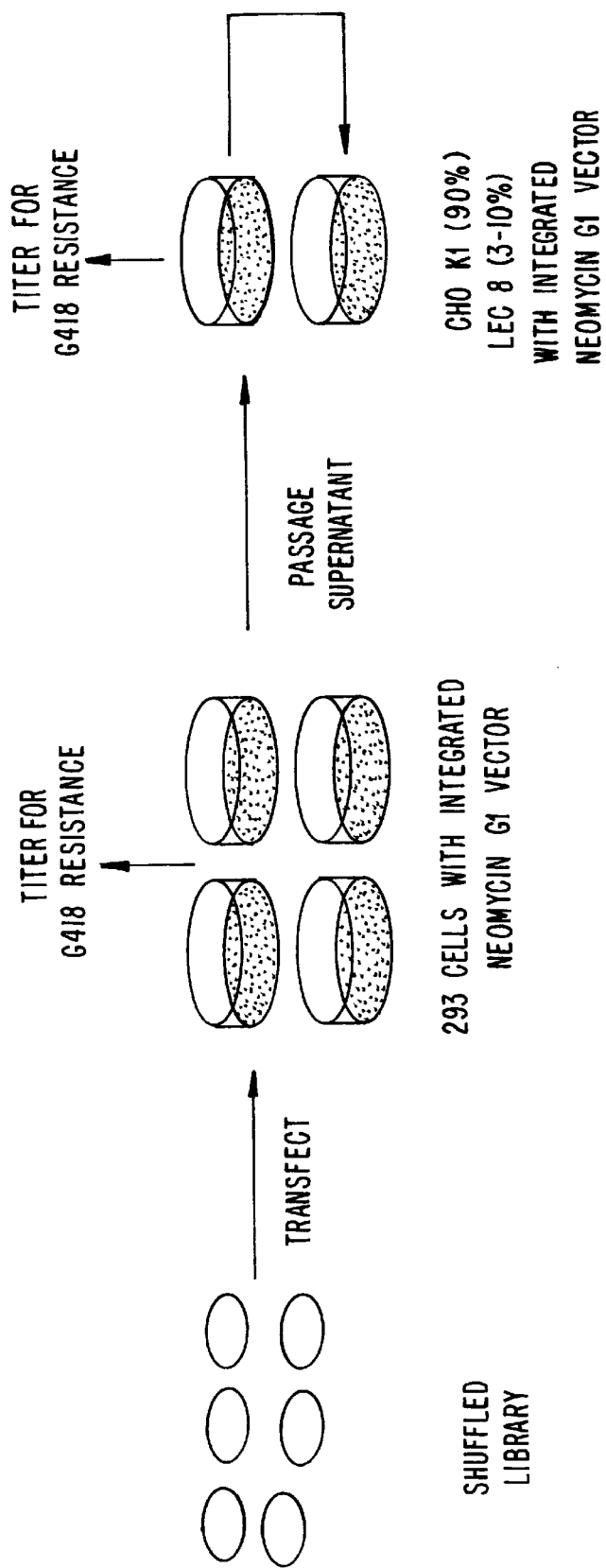
FIG. 7. Schematic diagram of Passaging of a Shuffled Library to select for CHO-Tropic virus.

Selection was performed by passaging the shuffled library supernatant on a mixture of CHO K1 and Lec8 cells as illustrated in FIG. 7 and described supra. A control mixture of the six unshuffled parents were passaged identically. A small proportion of Lec 8 cells was mixed in during passaging to support a low level of replication in a permissive cell type that was as similar to the target CHO K1 cells as possible. Lec 8 cells are CHO K1-derived mutants whose ecotropic receptors are believed to be more accessible because of a defect in their glycosylation pathways. This renders them permissive to infection by some ecotropic MLVs (See also Wilson, C. & Eiden, M. V. E. J. Virol. 65, 5975–5982 (1991); Miller, D. G. & Miller, D. J. Virol. 66, 78–84 (1992). Wang, H. et al. J. Virol. 70, 6884–6891 (1996)). Friend 2, Friend 9 and Moloney MLVs produced from transfected 293/G1 are able to infect Lec 8 cells fairly efficiently (Table 1).

Table 2 shows the progress of the selection for both the control unshuffled parents and the shuffled library. By titering at each stage, the changing 'infection profile' of the viral population was monitored. The initiating transfections into 293/G1 for the shuffled library produced supernatants that gave titers on 3T3, Mus Dunni and Lec8 that were on the order of $10^2$ fold lower than that for the control parental pool.

The infectious activities of both the control parental pool and the shuffled library fell to similar levels after one passage on the coculture cells, even though the shuffled library started out with $10^2$ fold lower titers. This indicates that the shuffled library is actually fitter than the parental pool under the coculture selection conditions. This point is underscored after a second passage of the viral pools. The parental pool essentially becomes extinct after the second passage (extremely low activity can be detected occasionally). The library titers fell to low but detectable levels that remained stable through passage 3. At passage 4, when the level of permissive Lec 8 was raised from 3% to 10%, the titers rose. Low CHO K1 infectious activity became detectable at passage 4 and this increased at passage 5 with the rise in overall titers.

Another particularly informative observation can be made by comparing the 'infectious profiles' of the control parental pool and the library pool at various stages of the selection. The infection efficiencies of the control parental pool after transfection on Mus Dunni and Lec 8 relative to 3T3 are approximately 10-2 and 10-3 respectively. This remains relatively constant through passage 1 before the population 'crashes' at passage 2. For the library pool, efficiencies for Mus Dunni and Lec 8 relative to 3T3 increased roughly 10 fold for each passage. From passage 2 onwards, these ratios approached 1. It fell back to 10-1 again at passage 5B when the overall titers increases. This implies that essentially every viral particle that can infect 3T3 at passages 2–4 can infect Lec 8 equally efficiently whereas in the unselected initial transfection pool, there is only one viral particle that can infect Lec 8 for every 300 particles that can infect 3T3. Thus there is strong selective pressure for the ability to infect and replicate in Lec 8. The parental pool apparently cannot adapt rapidly enough to this selective pressure. The evolved viral population surviving the selection has a low level of infectious activity on CHO K1 cells. Thus infection of CHO K1 cells becomes observable only after the population recovers from the selection during the first few passages to substantial levels.

Recovery and Characterization and Recombinant Clones

Genomic DNA was prepared from the coculture cells from various passages. This was used as template to amplify proviral sequences as described in Methods. Genomic DNA prepared from passage 5 cells which gave significant CHO K1 infectious activity, produced a clear product band of the expected 3.1 kb size. No specific product band was observed for passages 1–3 (passage 4 not performed) and for any of control parental passages. The PCR products amplified from passage 5 cells were pooled and cloned into the Moloney backbone to reconstitute potentially infectious clones. PCR fragments corresponding to the shuffled region were amplified from individual clones and screened by restriction digestion. The restriction patterns of none of the clones correspond to any of the parental patterns. Furthermore there is a dominant pattern (Clones 1–6, 8, 10–12) that represents the 'master sequence'. Clones 7 and 9 are slightly different from the dominant pattern but are also distinct from any of the parents.

Clones 3, 10 and 11, corresponding to the dominant pattern and the variant clone 7 were transfected into 293/G1 cells, and the supernatants were tested for infectious activity (Table 3a). Surprisingly, all of these clones had drastically diminished infectivities for CHO K1 when compared to the passage 5 pools from which they were isolated. Relative to titers on Lec 8 cells, the infectivities of these clones for CHO K1 was on the order of $10^{-5}$ or less, 100–1000 fold lower than that for passage 5 supernatants. This suggested that the 'CHO-tropic' clone in passage 5 was not represented by any of the four clones tested. The infectious efficiency of passage 5 supernatants on CHO K1 relative to the other cell types is about 10-3–10-2 (range from several subsequent titrations). This could be interpreted in two ways: 1) The predominant virus particle in this supernatant can infect CHO K1 at an relative efficiency of $10^{-3}$–$10^{-2}$; 2) there is one viral particle in every 100–1000 infectious particles that can infect CHO K1. If the latter were true, this rare clone would be expected to be selected for under our passaging regime and increase in frequency. However the CHO K1 infectious efficiency apparently has stabilized at $10^{-3}$–$10^{-2}$ suggesting the viral population has achieved some state of 'equilibrium'. This is supported by the clear dominance of one clone as shown by restriction analysis. These observations indicated that the clone that conferred CHO K1 infectivity was not missed, but that this activity was masked in our clones.

TABLE 1

Parental Titers on Various Cells

| Parent | 3T3 | Mus Dunni | CHO Lec8 | CHO K1 |
|---|---|---|---|---|
| Friend 2 | $3.0 \times 10^6$ | $5.1 \times 10^4$ | $6.5 \times 10^4$ | 0 |
| Friend 7 | 0 | $5.0 \pm 10^2$ | $8.0 \times 10^1$ | 0 |
| Friend 9 | $1.0 \times 10^1$ | $3.4 \pm 10^4$ | $1.2 \times 10^5$ | 0 |
| Friend 21 | $4.0 \times 10^5$ | 0 | 1 | 0 |
| 292E | $6.4 \times 10^3$ | $5.0 \times 10^2$ | 0 | 0 |
| Moloney | $1.7 \times 10^6$ | $1.0 \times 10^2$ | $6.0 \times 10^5$ | 0 |

TABLE 2

Titers of parental and shuffled library passage supernatants on coculture cells

| | Titer cells | Trans-fection | Coculture Passage Number | | | | | |
|---|---|---|---|---|---|---|---|---|
| | | | 1 | 2 | 3 | 4 | 5 | 5B<sup>&</sup> |
| Control Parentals | 3T3 | $1.2 \times 10^7$ | $7 \times 10^3$ | 0 | 0 | 0 | 0 | ND |
| | MD | $3 \times 10^{5*}$ | $4 \times 10^2$ | 0 | 0 | 0 | ND | ND |
| | Lec8 | $1.4 \times 10^{4*}$ | 30 | 0 | 0 | 8 | 0 | ND |
| | CHOK1 | 0 | 0 | 0 | 0 | 0 | 0 | ND |
| Shuffled Library | 3T3 | $3 \times 10^5$ | $1 \times 10^3$ | 16 | 7 | $10^2$ | $2 \times 10^4$ | $10^6$ |
| | MD | $10^4$ | $4 \times 10^2$ | 20 | 30 | 45 | ND | $10^5$ |
| | Lec8 | $9 \times 10^{2*}$ | 40 | 19 | 19 | $10^2$ | $>5 \times 10^4$ | $10^5$ |
| | CHOK1 | 0 | 0 | 0 | 0 | 10 | $5 \times 10^2$ | $10^3$ |

MD Mus Dunni
ND not done
*from separate experiment which gave comparable titres on 3T3
<sup>&</sup>supernatants from later cultures split from passage 5

TABLE 3a

Diminished CHO K1 Infectivity after Growth in 293/G1 cells

| | Titer Cells | | | |
|---|---|---|---|---|
| CLONE # | 3T3 | Mus Dunni | Lec8 | CHO KI |
| 3 | $10^4$ | $10^6$ | $10^6$ | 10* |
| 7 | 50 | $10^5$ | $10^4$ | 0 |
| 10 | $10^3$ | $10^5$ | $10^5$ | 0 |
| 11 | $10^4$ | $10^5$ | $10^5$ | 10* |

*estimated from a single G418 resistant colony in the $10^{-1}$ titration well.

TABLE 3b

CHO K1 infectivity is reconstituted after passage through Lec8/G1 cells

| | Titer Cells | | | |
|---|---|---|---|---|
| CLONE # | 3T3 | Mus Dunni | Lec8 | CHO KI |
| 3 | $10^6$ | $10^6$ | $10^6$ | $10^3$ |
| 7 | 10 | $10^3$ | $10^2$ | 0 |
| 10 | $10^5$ | ND | $10^6$ | $10^3$ |
| 11 | $10^5$ | $10^6$ | $10^6$ | $10^3$ |

Lec 8 Passaging Effects

Lec 8 cells were included in the coculture as permissive cells to allow some level of viral replication. They have a known defect in their glycosylation pathway (See e.g., Stanley, P. & Siminovitch, L. Somat. Cell Genet. 3, 391–405 (1977)) that apparently 'unblocks' their ecotropic receptors (Wilson, C. & Eiden, M. V. E. J. Virol. 65, 5975–5982 (1991); Miller, D. G. & Miller, D. J. Virol. 66, 78–84 (1992); Wang, H. et al. J. Virol. 70, 6884–6891(1996)). We wondered if the mechanisms that unblock the Lec8 cellular receptors might also operate on virus that are passaged through these cells. To investigate this, 293/G1 transfection supernatants from the viral clones described above were used to infect Lec8/G1 cells. This was replaced with fresh media which was collected after 48 hours and titered (Table 3b). All clones except #7, had their CHO K1 infectivities reconstituted to levels similar to passage #5 supernatants (CHO K1 infection efficiency ranges between $10^{-3}$–$10^{-2}$ due to experimental variations). This suggested that there was a requirement for Lec8 specific processing of virus before CHO K1 infectivity was manifested. Clone #7, which had a different restriction pattern from the dominant pattern, may represent a 'passenger' virus or may have diverged further from the 'master sequence' and lost the ability to infect CHO K1. Clones 7 and 10 were not analyzed further. The envelope sequences for clones 3 and 11 were sequenced.

From Table 1, it can be seen that the Friend 2, Friend 9, and Moloney MLV parents can infect Lec 8 fairly well. Thus, it was interesting to determine why the control parental pool passaged virtually to extinction so rapidly. To examine this, these parental clones were transfected into 293/G1, the supernatants from these were then passaged either through Lec8/G1 or permissive murine lines (Mus Dunni/G1 or SC1/G1). The supernatants from these various stages were titered (Table 4). Friend 2 and Moloney MLV produced high titer virus on 3T3 after passage through Lec 8. However their infectivities on Lec 8 relative to 3T3 were diminished by 100–1000 fold when compared to the 293/G1 transfection supernatants. Friend 9 either not did replicate well in Lec 8 or produced poorly infectious viruses. Supernatants from Mus Dunni/G1 or SC-1/G1 passages essentially preserved the infectious profiles of the initial 293/G1 transfection supernatants. As expected, none of the parental supernatants could infect CHO K1 regardless of how they were passaged. Thus, the parental viruses lose the ability to reinfect the permissive Lec8 cells with each passage. This would lead to the progressive and rapid dilution of virus production and to the observed rapid decline of the infection during passaging.

Sequences of Recombinant Envelope

Figure 8:
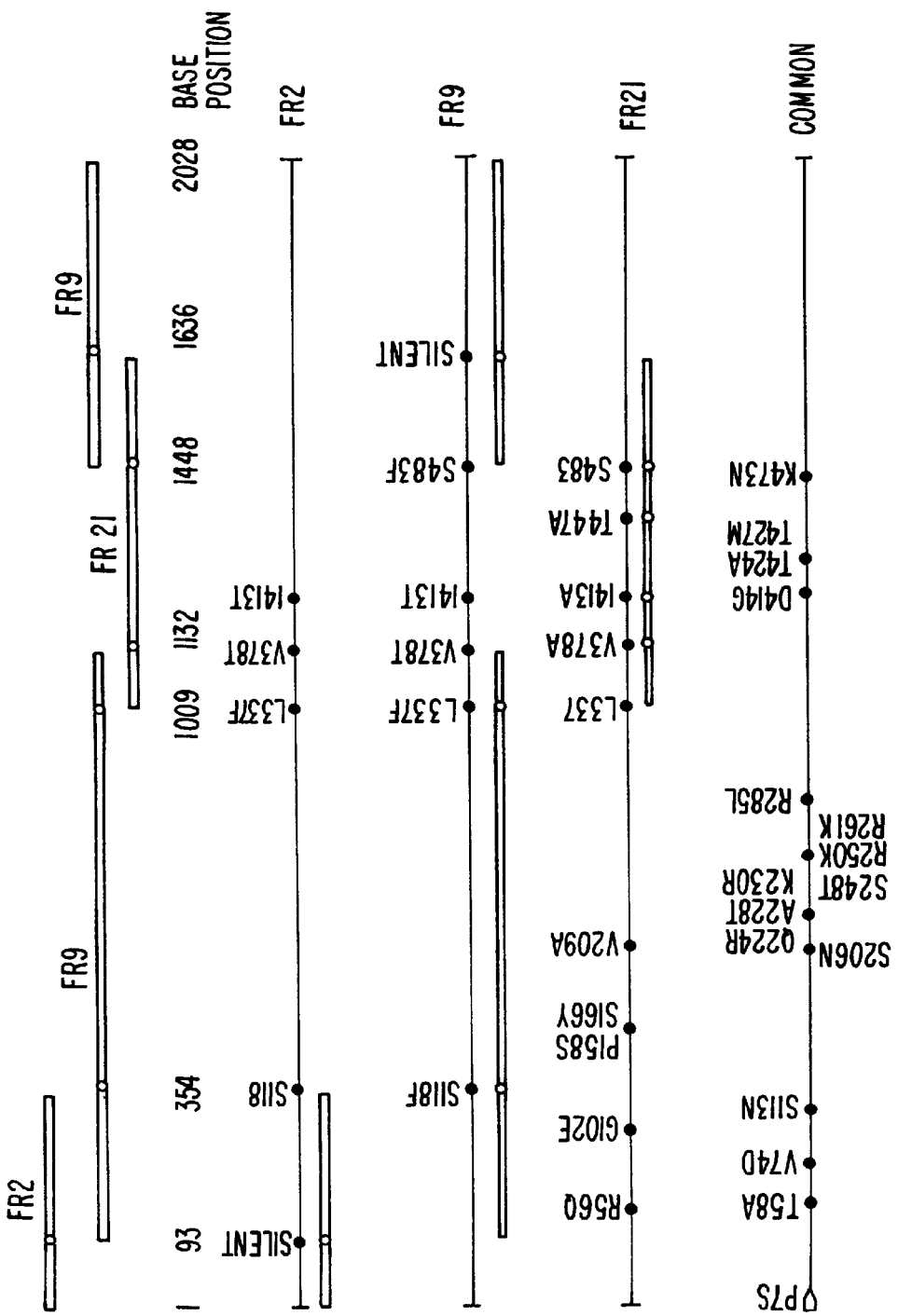
FIG. 8. Structure of recombinant CHO-tropic envelope showing contributions from three parents.

The envelope sequences of Clones #3 and #11 are most consistent, with a four fragment recombination between three of the Friend parents (FIG. 8). The sequence of clone #3 can be explained by recombination alone, while that for clone #11 has an additional silent base change at position 231. Nucleotide differences between the parents allow us to map the regions where crossovers took place. It is not surprising that the Moloney and 292E sequences were not included in the selected clones. Recombination events involving these two parents may be under-represented as they have lower degrees of identities with the Friend sequences. Because of their greater divergence, recombination events may also have a higher probability of generating non-viable clones. Although the 3' LTR and parts of pol were also shuffled, it is unlikely that they play significant roles in the new tropism of the recombinant clones. Pol is highly conserved between ecotropic MLVs and is not known to have a role in entry. Cloning of recombinant envelope sequences which excludes the 3' LTR, using the Sfi I site in pol and a conserved Cla I site towards the end of the envelope is sufficient to confer CHO K1 tropism (data not shown). This indicates that the changes in the LTR were not necessary.

DNA shuffling was used to improve individual genes as well as multigene pathways. In this example, we report an application of shuffling to evolve a desired phenotype in a viral system. The ability to infect CHO K1 cells was evolved by shuffling sequences from a defined set of ecotropic parental MLVs. No a priori assumptions were made of the changes required to overcome the CHO K1 entry block other than that the envelope was involved.

Predominantly, envelope sequences from the six parents were shuffled to generate a library of about $1 \times 10^6$ clones. At least one third of these were recombinant. This shuffled library consistently gave 100 fold lower titers than the parental pool upon initial transfection into 293/G1 cells. This is caused by the generation of many lethal and debilitated sequences by the shuffling process. Thus the fitness of the naïve library is lower than the unshuffled parental pool. This reflects the 'cost' of the shuffling process in generating diversity at the expense of population fitness.

An initial attempt to select directly on CHO K1 cells alone led to rapid extinction of both the library pool and the control parental pool. This indicated that the barrier to CHO K1 infection was high enough that an effective solution was not sufficiently represented in the initial library. There might have been variants that could infect CHO K1 cells, but these were either too rare or were too inefficient that they were easily lost during the stringent direct selection. To enrich for these possible variants, we mixed in a low proportion of permissive Lec8 cells. These cells were chosen as they were CHO K1 derived mutants and thus would serve as a relevant 'bridge' to the target CHO K1 cells themselves. With the coculture selection, the titers of both the parental pool and shuffled library pool fell to similar levels after 1 passage, despite the 100 fold higher initial titers of the parental pool. By the second passage onwards, there was little detectable infectious activity in the parental pool while in the library pool, infectious activity was low but clearly present. Thus there were clones in the library that were surviving the selection as a result of the added diversity generated by shuffling. CHO K1 infectivity was observed from passage 4 onwards as the overall titers increased.

Proviral envelope sequences cloned from passage 5 coculture genomic DNA revealed a dominant recombinant pattern whose parental origins can be deduced (FIG. 8). Three of the Friend parents contributed to this recombinant envelope whose structure is different from any of the published MLV related strains that can infect CHO K1. These include the 10A1 strain the Gibbon Ape Leukemia Virus (Delassus, S., Sonigo, P. & Wain-Hobson, S. Virology 173, 205–213 (1989)), and the neuropathogenic Friend variant PVC 211 (Masuda, M., Masuda, M., Hanson, C., Hoffman, P. M. & Ruscetti, S. K. J. Virol. 70, 8534–8539 (1996)). The two residue changes in PVC211 (E116G and E129K; numbering according to reference) relative to the published Friend 57 clone do not occur in our recombinant clones or in any of the parents. A Mus Dunni Endogenous Virus (Bonham, L., Wolgamott, G. & Miller, A. D. J. Virol. 71, 4663–4670 (1997)) is also highly infectious for CHO K1 but based on its source and properties is not related to our recombinant clone.

An interesting feature is the requirement of our recombinant clones to be passaged through Lec8 cells for it to acquire CHO K1 infectivity. When the clones were replicated in 293/G1 cells, their infectivity for CHO K1 relative to Lee 8 is 10-5 or lower. After passage through Lec 8, this increased 100–1000 fold to 10-3–10-2. As a result of a mutation in the glycosylation pathway of Lec 8 cells, their golgi can only import galactose at 2% of wild type levels, resulting in low efficiency of terminal addition of galactose and sialic acid at N-linked glycosylation sites (Deutschert, S. L. & Hirschberg, C. B. Mechanism of Galactosylation in the Golgi Apparatus. J. Biol. Chem. 261, 96–100 (1996). An altered glycosylation pattern of the envelope when expressed in Lec 8 may be responsible for enhancing CHO K1 infectivity. Glycosylation patterns of retroviral envelopes produced in different CHO glycosylation mutant cell lines are clearly different (Fenouillet, E., Miquelis, R. & Drillien, Virology 218, 224–231 (1996). Friend 21 is more divergent than any of the other Friend parents. In the segment that Friend 21 contributes to the recombinant clones, three amino acid residues (378, 413 and 447; FIG. 8) that are specific for Friend 21 are positioned 1–3 residues away from N-linked glycosylation sites. These may influence the efficiency of sugar addition which may in turn affect the overall conformation of the envelope. Cellular processing and conformation of retroviral envelope glycoproteins are known to be heavily dependent on glycosylation signals. The receptor binding domain (Heard, J. M. & Danos, O. J. Virol. 65, 4026–4032 (1991)) of the recombinant envelope is provided by Friend 2 and Friend 9 parents, both of which can infect Lec 8 cells. It may be that this receptor binding domain in juxtaposition with the altered glycosylation signals from Friend 21 is processed in Lec 8 cells to produce an envelope that is able to reinfect Lec 8 cells and to a lesser degree, to infect CHO K1 cells. The glycosylation mediated block of CHO K1 receptors can be relieved by inhibiting glyosylation in these cells. This may have the effect of making the receptors more accessible to the envelope. The same effect might also be achieved by under-glycosylating the retroviral envelope itself. This modification of retroviral tropisms by altering the glycosylation pattern of envelopes may represent a novel mechanism that has not been reported previously.

The passage of parental viruses produced from 293/G1 through Lec 8 results in poor production of infectious viruses (Friend 9) or in progeny viruses that cannot reinfect Lec 8 efficiently (Friend 2 and Moloney). This may be a direct result of the altered glycosylation pattern of these parental envelopes in Lec 8 cells. Under-glycosylation of the Friend 9 envelope may lead to gross misfolding while for Friend 2 and Moloney, this may lead to conformational changes that result in the inability of the envelope to bind the Lec8 receptor efficiently. The rapid abrogation of the parental infection after two passages on the coculture cells can be explained by the progressive loss of the ability of the parental viruses to reinfect the permissive Lec8 cells. Recombination during shuffling between various parental segments generated clones that circumvented this restriction and were therefore selected for. It is unlikely that in vivo retroviral recombination had a significant role in generating the selected clones. Friend 21, which contributes a substantial segment, cannot infect Lec 8. Thus, outside of the initial transfection into 293/G1, there are extremely limited opportunities for the other Friend parental genomes to be in the same cellular compartment to be copackaged together. This is further exacerbated by the progressive loss of infectivities for Lec8 of the parents with each passage. None of these biological restrictions are applicable to the in vitro shuffling process, which can create multi-fragment recombinants in a single reaction. This situation underscores the direct role of the in vitro recombination process in generating the recombinants. Thus, shuffling allowed novel recombinants to be created which natural mechanisms of retroviral recombination would not be likely to create.

Ishimoto, A. Journal of the National Cancer Institute 74, 905–908 (1985) was able to adapt Friend MLV strains to infect Syrian Hamster cells at improved efficiencies by continuous passaging. The starting virus was obtained initially as in vivo mouse passaged stocks comprising a 'diverse quasispecies' and already had a low level of infectivity for hamster cells. Our starting viral stocks were six defined molecular MLV clones which had no detectable infectivity for CHO K1. From these we generated a diverse library of recombinants in one round of shuffling and obtained a recombinant sequence that could circumvent the CHO K1 entry block. Thus, shuffling allows high diversity to be achieved rapidly from a limited repertoire of starting sequences. The use of diverse but related parental sequences (each of which has evolved separately) in family shuffling enables functional sequence space to be explored efficiently and novel solutions to be rapidly found. Further rounds of shuffling and selection yield greater improvements. DNA shuffling thus is a useful tool to solve some of the current limitations in viral vectors where there are multiple variables and where detailed knowledge of the limiting mechanisms is incomplete.

Methods

Cell Lines

Cell lines were obtained from American Type Culture Collection. A retroviral vector expressing the G418 resistance marker (from Gene Therapy Laboratories, University of Southern California) was introduced into these cells which were then subjected to G418 selection at 0.8–1 mg/ml. About 20–100 resistant colonies for each cell type were pooled. These G418 resistant lines are denoted with a '/G1' suffix.

Viruses

Friend MLV (ATCC VR 245) was obtained as a spleen extract containing a mixture of three viruses. An ecotropic 292E strain (ATCC VR 1326) was obtained as a supernatant from infected NIH 3T3 cells. Genomic DNA from Mus Dunni cells infected with these stocks were used to recover proviral sequences of the different MLV strains (below). Plasmid pNCA (gift from S. Goff, University of Columbia) contains a full length, non-permuted copy of the wild type Moloney MLV proviral DNA in a pBR322 based vector (Colicelli, J. & Goff, S. P. J. Mol. Biol. 199, 47–59 (1988)).

Cloning of Envelope Sequences

Genomic DNA was isolated from Mus Dunni infected with Friend or the 292 ecotropic (292 E) MLV strains using the Puregene kit (Gentra Biosystems) and manufacturer's protocols. Primers were designed to amplify Friend and 292E MLV proviral sequences based on the published Moloney MLV sequence (Genbank accession number M76668). The upstream sense primer Mol PolESn straddles the SfiI site in the pol gene which is highly conserved between ecotropic MLV strains. The downstream antisense primer, MolU5as is positioned at the 3' end of the U5 sequence. A NotI site is also included in the 5' tail of this primer (FIG. 1). PCR was performed using reagents from the GeneAmp XL PCR kit (PE Applied Biosystems). Final concentrations of Mg acetate, primers and each dNTP were 1.25 mM, 0.5 uM and 200 uM respectively. PCR fragments from the 292E and Friend amplifications were processed and eventually cloned into a modified pNCA (see below) acceptor backbone using the SfiI and NotI unique sites. Plasmid pNCA was modified by inserting a Not I site just downstream of the 3' LTR of the Moloney MLV sequence. A unique Sfi site exists in the 3' region of the pol gene. Cleavage of the modified pNCA plasmid with Not I and Sfi I excises about 0.5 kb of pol, the entire env and 3' LTR. The remaining backbone then served as an acceptor vector for the cloning of the analogous Friend and 292E MLV fragments. The pNCA thus provided most of the 5' sequence of Moloney MLV while the 3' region of pol and the entire env and 3'LTR were replaced with Friend and 292E sequences. Multiple full-length Friend and 292E clones were then screened for infectious activity One 292E clone and four Friend clones that produced infectious virus were chosen as parental sequences. The four Friend clones (#2, 7, 9, 21) exhibited different relative infectivities on 3T3 and Mus Dunni cells.

Transfections

Transfections were performed by calcium phosphate precipitation using reagents from 5 Prime 3 Prime and manufacturer's protocols. 30 ug of full-length proviral clones or library DNA were transfected into 5×106 293/G1 cells (plated one day prior to transfections) per 100 mm tissue culture dish. The precipitate was allowed to settle on cells for 16–18 hours before being washed off. Sodium Butyrate (Sigma) was added in fresh Dulbecco's Modified Essential Media (Gibco) containing 10% fetal bovine serum (FBS; Hyclone) to a final concentration of 10 mM. After 6–8 hours exposure, the media was removed and replaced with 5 ml of fresh media. This supernatant was collected after 20–24 hours and frozen. Another 5 ml of fresh media was added for a further 20–24 hours and a 2nd supernatant collection was performed. This was pooled with the first collection, filtered through 0.45 uM syringe filters (Gelman) and used for titrations or passaging.

Viral Titrations by Marker Rescue

Cell types used in transfections or passaging of infectious virus contain an integrated retroviral vector expressing the G418 resistance marker. Thus we were able to monitor the infectious activity of fully replicative MLV by titering viral supernatants and selecting for G418 resistance. This also allowed us to compare relative efficiencies of virus infection on various cell types. Briefly, 10 fold serial dilutions of virus supernatants in media containing 8 ug/ml of Polybrene (Sigma) were allowed to infect cells on 6 well plates (plated one day prior at 2–3×10$^5$ cells/well). After incubation at 37 C overnight, the supernatant was replaced with media containing 1 mg/ml of G418 (Calbiochem, La Jolla, Calif.). Selection was continued for 7–10 days. Surviving resistant colonies were stained by with methylene blue/methanol and counted.

Shuffling of Proviral Sequence and Library Construction

These six clones were used as templates for PCR amplification to generate material for shuffling. MolPolESn and pBRas, an antisense primer in the pBR322 vector sequence just downstream of primer MolU5as were used to amplify a specific 3.2 kb product. PCR products from each of the six parents were purified and mixed together in equimolar amounts. This mixture was then digested with DNAse I (Sigma), DNAsed fragments in the size range of 0.7–1.6 kb were purified and used in the shuffling reaction essentially as described before (Crameri, A., Whitehom, E. A., Tate, E. & Stemmer, W. P. C. Nature Biotechnology 14, 315–319 (1996)). The completed shuffling reactions were used as templates for preparative PCR using primers MolPolEsn and MolU5as. Products from this were purified and digested with NotI and SfiI. These fragments were then cloned into similarly digested modified pNCA acceptor backbone and transformed into XL-10 Gold competent cells (Stratagene). Approximately 1×106 colonies were obtained and pooled and used to prepare library plasmid DNA. Several independent colonies were also individually picked and analyzed. Fragments representing the shuffled region were amplified from these clones. These PCR fragments were digested simultaneously with Bgl L, Cla I, Dra I, Dra III and Sac II. The digests were run out on a 1.5% agarose gel and compared to the restriction patterns of the parents. Clones were also assayed for viability.

Library Passaging/Selection for CHO K1 Tropic Virus (FIG. 2)

Library plasmid DNA was transfected into 4 plates of 293/G1 cells as described above. 40 ml of supernatant was collected. About 5 ml of this was used for titering while 10 ml (polybrene was added to 8 ug/ml) was passaged onto a coculture of CHO K1/G1 (90%) and Lec 8/G1 cells (plated at a total density of 5×105 cells/100 mm plate. The coculture cells were exposed to this supernatant for 24–48 hours before being replaced with fresh F12 Ham (Gibco BRL) media with 10% FBS. When the coculture cells had grown to 90–100% confluency, fresh media was added and left on the cells for 48 hours. This supernatant was collected, filtered and used for titering and for passaging onto fresh coculture cells. As a control to account for natural recombination and adaptation, an equimolar mixture of the six parental clones were transfected, passaged and assayed identically to the library supernatant.

Sequencing

Fluorescent DNA sequencing of MLV envelopes was performed using an ABI Prism 310 Genetic Analyzer and reagents supplied in the BigDye Terminator Ready Reaction kit (ABI Prism). Raw sequence collection software(v1.0.4) and sequencing analysis software(v3.0) was also supplied by ABI Prism. Sequencher v3.0 software (Gene Codes Corporation) was used for contig assembly and alignments.

Example 6

Evolution of Hepatitis C Virus (HCV) to Grow in Tissue Culture

Hepatitis C Virus (HCV) represents the predominant cause of transfusion associated non-A, non-B hepatitis. Infection is usually chronic with an estimated 4 million people in the United States and 100 million people worldwide that are chronically infected with HCV. It has a high propensity to cause chronic hepatitis, which could progress to liver cirrhosis and then hepatocellular carcinoma. There is at present no vaccine for HCV and therapy with interferon is only 20–30% efficacious.

The chimpanzee represents the most reliable animal model, although their availability is extremely limited and disease in this species is generally mild. Development of vaccines and therapeutics has been hampered by the lack of efficient replication of HCV in tissue culture in vitro. Although infection of some human tissue culture lines have been reported, there is little evidence for the ability of stable molecular clones to carry out complete replication cycles. The value of evolving such infectious molecular clones of HCV that can replicate in established cell lines will thus be significant. It will greatly facilitate screening for anti-viral therapeutics, allow for the establishment of neutralizing antibody assays and provide systems for vaccine development.

The genome of HCV consists of a 9.5 kb positive stranded RNA with a single large open reading frame (ORF). This functions as the template mRNA from which all viral proteins are translated. The ORF codes for a large polyprotein which is cleaved co- and post-translationally to generate the individual viral proteins. Genomic RNA as well as RNA transcripts from full length cDNA clones should be infectious. However, are multiple blocks that prevent robust replication in vitro one of which is the inefficient translation of HCV transcripts. These blocks are addressed using DNA shuffling followed by selection in target cells such as human liver cell lines. These target cells include those that naturally express the HCV receptor, e.g., CD81, as well as those that either that do not express CD81 or only express it at low levels. To enhance expression of CD81 and thus facilitate infection of cells with evolved HCV variants, cell lines are optionally stably or transiently transfected with a CD81 cDNA expression vector. Cells lines that could be used in the screening, after transfection with CD81, include, but are not limited to, Hela, Cos-1, Cos-7, CHO, 293, U937, HL60, Jijoye, Jurkat, Hep G2, C3A, TF-1, Baf-3. Methods for stable transfection are known to those skilled in the art, and are described for example by van der Merwe et al. (J. Exp. Med. 185, 393–403, 1997) and Lanier et al. (J. Immunol., 154, 97–105, 1995).

Shuffling is performed on the entire genome of HCV or subgenomic portions or both. The size of the HCV genome is within the range of previous sequences that have been successfully shuffled (e.g. adenovirus, with >20 kb shuffled). Furthermore, the genome of HCV is highly heterogeneous with the assignment of at least six HCV types encompassing 11 subtypes. The most divergent HCV isolates differ from each other by more than 30% over the entire genome. Sequence identities lower than this have been successfully shuffled (e.g. Cephalosporinase). Moreover, HCV, like many RNA viruses circulates as a quasispecies, further adding to natural diversity which can be harvested for shuffling.

Protocol for Shuffling and Selection of HCV

Prepare large quantities of genomic and/or subgenomic fragments of multiple species of HCV by PCR or by amplification in bacteria. These are obtained as full length or partial molecular clones, or from clinical samples.

DNA shuffling is performed, including e.g., DNAse I digestion, PCR assembly, (e.g., a long range, high-fidelity PCR protocol). The PCR can be performed such that a promoter such as T7 is incorporated at the 5' end. PCR fragments (full length or subgenomic) are optionally cloned into a HCV genomic cDNA template with a promoter incorporated to reconstitute full length molecular clones. Runoff transcription is performed to generate libraries of potentially infectious transcripts. Pools of RNA transcripts are transfected into target cells. As noted above, target cells include those which express CD81, either naturally, or following transfection with a CD81 coding nucleic acid. Infectious sequences are recovered by PCR, e.g., from virions or negative strain (replicated) RNA by RT-PCR. It is also possible to enrich or select for replicating infectious virus by passaging infected cells or supernatants on target cells. Shuffling and selection steps are repeated as desired.

Example 7

Top Down and Botton Up Shuffling of HIV-1 to Change Viral Tropism

The principal purpose of this example is to apply DNA shuffling technology, or molecular breeding, to the problem of evolving a variant of HIV-1 that can replicate in mouse cells and in transgenic mice expressing hCD4 and hCCR5. There is wide consensus in the field that there is a large unmet need for a small animal model for AIDS in which to test the many emerging small molecule therapeutics that have been discovered recently. Additionally, there is an enormous unmet need for basic research on HIV-1 vaccines. The HIV-1 variants that are evolved to replicate in hCD4+ hCCR5+ double transgenic mice add valuable new tools to meet these urgent biopharmaceutical and human health needs.

An additional goal of this example is to evolve HIV to replicate in macaque cells by methods similar to those being used to evolve the virus to replicate in mouse cells. The motivation for this approach is that there are known to be fewer blocks to HIV replication in macaque cells (for example, transfected molecular clones produce infectious virus), and hence this is easier to achieve. Additionally, the physiology and immune systems of macaques are more similar to the corresponding human systems than are the murine systems, making macaques a good vaccine model.

The recent discoveries of the HIV coreceptors CXCR4 and CCR5 have removed the barriers to infection of murine cells by HIV-1. However, there remain blocks to HIV-1 replication in murine cells. There is not sufficient diversity in available HIV-1 isolates to directly select a mutant virus that can replicate on the murine target cells (Harris Goldstein and colleagues, PNAS 94:14637–14641, 1997). Consequently, a variant capable of serving as a mouse model for AIDS needs multiple mutations to overcome these blocks. DNA shuffling is a method for improving single and multi-gene traits which require many mutations and this method has generated improvements ranging from 10 to 32,000-fold. Neither a priori assumptions nor knowledge of the gene structures are required for successful application of gene shuffling. Thus, the technology is adaptable to the problem of adapting HIV-1 to replicate in non-human cells.

If a virus is evolved or engineered to replicate in murine cells, it will have many mutations relative to wild type HIV-1 which may be unnecessary for replication in murine cells and which will compromise it as a valid model for AIDS. DNA shuffling provides a solution to this problem because one can backcross a mutant of interest with wild type strains. This natural feature of shuffling technology is used to perform in vitro backcrosses of evolved variants with wild type HIV-1 strains of commercial interest. This step will ensure that only those mutations necessary for viral propagation in the mouse are preserved, thereby optimizing the predictive value of this laboratory model for the human disease. These evolved viruses will be used in conjunction with the double transgenic mice to identify novel small molecule drugs and prophylactic and treatment vaccines.

Figure 9:
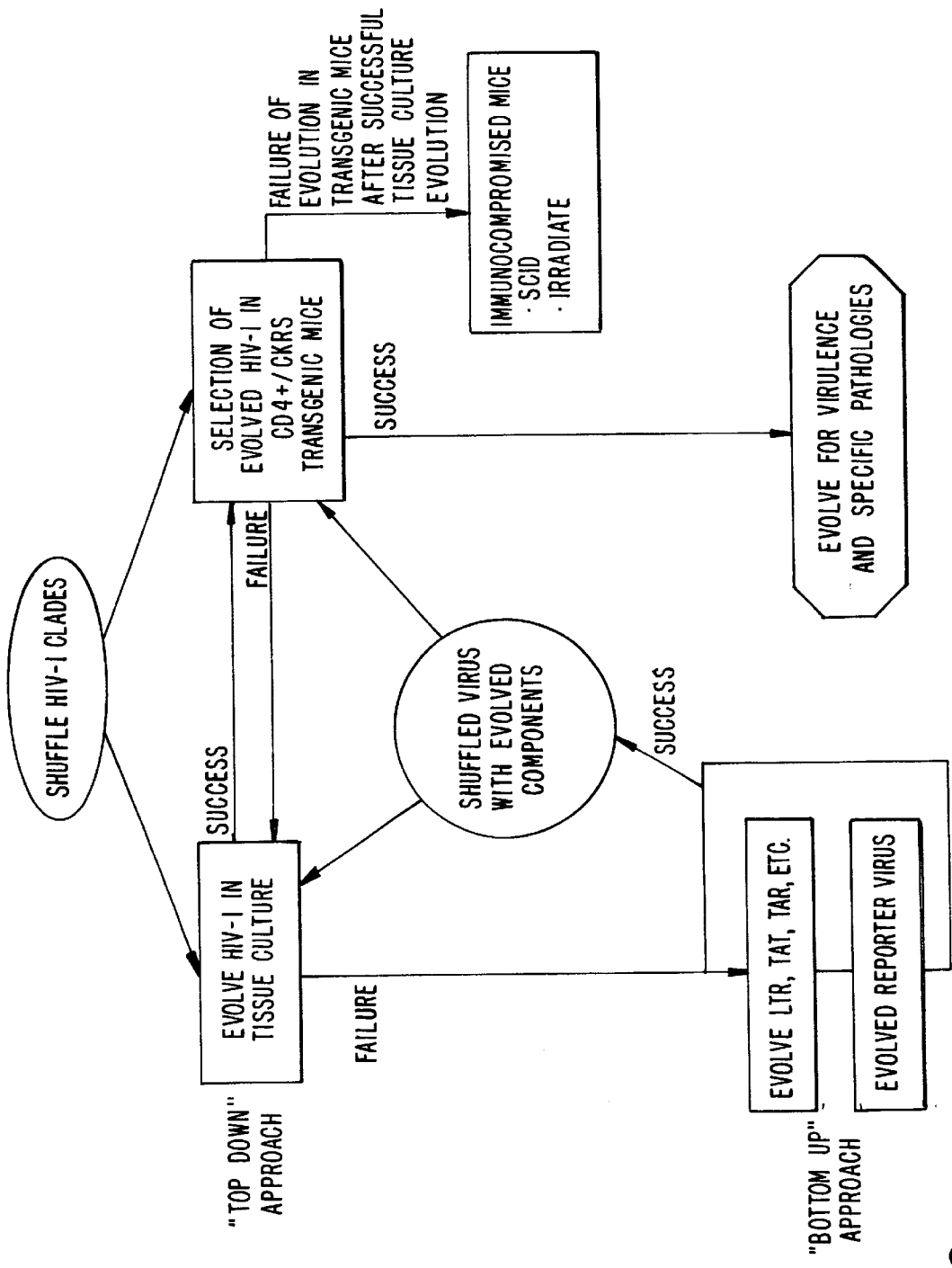
FIG. 9. HIV-1 Evolution Decision Tree.

The experimental strategy is schematized in FIG. 9. HIV-1 is adapted to grow in murine tissue culture cells using both "top down" and "bottom up" approaches. These mutants are further evolved to replicate in hCD4+, hCCR5+ double transgenic mice, and to cause pathogenesis. These mutant HIV-1 isolates are backcrossed to wild type HIV-1 isolates to obtain a virus that can replicate in the transgenic model while being maximally similar to wild type human HIV-1 isolates. FIG. 9 schematizes the strategic choice tree that used to prioritize objectives and to decide when to move on to subsequent modules of HIV shuffling and design.

Top Down Approach

In the top down approach, a mutant virus is identified that can replicate, however weakly, on hCD4+ hCCR5+ murine cells. This is done by testing existing HIV-1 isolates and by constructing libraries of novel HIV-1 recombinants using DNA shuffling. Initial selection is performed in tissue culture cells. Weakly replicating viruses serve as starting points for further evolution. To increase the efficiency of selecting a mutant virus that can be propagated in murine cells, DNA shuffling is used to recombine the diversity that exists in the natural HIV population. Libraries of novel recombinants are generated containing mutants that are capable of replicating in the hCD4+ hCCR5+ murine target cells. Viral replication is quantitated by measuring p24 production and viral reverse transcriptase activity. The goal is to evolve a virus that yields a tissue culture infectious dose-50 (TCID-50) of 1–10% the level produced by wild type HIV-1 on human cells. This approach initially yields weakly replicating virus. Weakly replicating virus obtained directly by DNA shuffling of the natural diversity, is further evolved using recursive application of DNA shuffling and selection for growth on the target murine cells.

Objectives for the "top down" approach are as follows. First, methods for shuffling HIV-1 are established, and efficiently reconstructing infectious viral genomes (i.e. library sizes of >$10^6$). Shuffling of a 10 kb genome is well within the capability of standard DNA shuffling. Second, a mutant virus is obtained that demonstrates measurable ability to replicate on murine cells, as defined by the ability to serially transfer the ability to produce viral antigens or viral RT activity. Third, DNA shuffling is applied to improve on this activity. Viruses with weak replication activity are subjected to recursive DNA shuffling and selection in vitro in tissue culture cells, with the goal of evolving a viral titer that is 0.1%–10% of that of wild type HIV-1 on human cells. These evolved viruses are used for further selection experiments in double transgenic mice.

Bottom Up Approach: Evolution of Viral Components

The top down approach relies on whole HIV-1 genome shuffling to create initial weakly replicating viruses. This is technically challenging because there are multiple blocks to replication. The following approach also utilizes DNA shuffling, but takes a "bottom up" approach to the problem. The overall goal is broken into step-wise objectives, providing an incremental pathway toward the adaptation of HIV-1 to grow in transgenic mice. First, the HIV-1 LTR, tat and tar are evolved for efficient function in mouse cells. Second, the mutants are shuffled into HIV-1 with a reporter GFP construct inserted at the 3' end of the genome and further evolve the reporter virus to efficiently express full length transcripts. Third, mutants are evolved to replicate in mouse tissue culture cells and produce high titer viral stocks. Fourth, if further blocks remain after evolving tat, these are biochemically and genetically identified and reporter assays are designed with which to evolve the components. The rev and vpr genes are examples of individual genes that are optimized for function in mouse cells.

These goals are chosen to define an incremental pathway whereby DNA shuffling is used at each step to overcome blocks in viral replication, and in the end solve a highly complex problem that may require many mutations and hence is not readily accessible by any competing approach. The quantitative objectives for this second approach are as follows. First, a 10–100 fold increase in mouse cell expression is obtained for GFP reporter construct driven by tat, tar and the HIV LTR. Second, mouse cell expression of a GFP reporter gene encoded at the 3' end of the HIV-1 LTR is obtained that is 10–50% of the level expressed by a wild type HIV-1 GFP reporter virus integrated into human cells. Third, viral titers of 1–50% of wild type HIV-1, as quantitated by p24 concentration or quantitative RT-PCR measurements of viral RNA in the supernatant in standard spreading infection assays is obtained. The kinetics of growth are measured with these assays to demonstrate that infectious material exists. Fourth, other replication blocks are characterized as necessary.

Two recent publications affect the strategy herein. Jones and colleagues have recently reported the cloning of a human transcriptional elongation factor that interacts with tat (Cell 92:451–462, Feb. 20, 1998; A Novel CDK9-Associated C-Type Cyclin Interacts Directly with HIV-1 Tat and Mediates Its High-Affinity, Loop-Specific Binding to TAR RNA). The results of this work, presented at the March 1998 Keystone Symposium, showed that human Cyclin T interacts directly with tat in activating polII for elongation of messages driven by the HIV LTR. Jones transfected this gene into mouse cells and showed an increase in tat inducible gene expression. Introduction of this human gene into transgenic mice relieves one of the blocks to HIV replication.

The use of SCID-Hu mice for studying protease and RT inhibitors in vivo has been reported on (J. Infec. Dis. 177:337–346, 1998). HIV can replicate in this system and known RT and protease inhibitors inhibit replication. The broad use of SCID-Hu mice for drug studies is limited by the high cost of producing these mice which have to be individually repopulated with fetal human cells. Additionally, one will not be able to make use of genetic manipulation of the murine immune system, such as CD4 and CD8 knockouts, in this system. This study illustrates the utility of a mouse model for studying HIV. The approach herein has the potential to overcome the limitations of this model.

Evolution of Whole Virus

In one embodiment, the following steps are used to evolve HIV for replication in non-human cells. First, cloning vectors and protocols for shuffling infectious molecular clones in two non-infectious pieces are established. Second, methods for efficiently making large (>$10^6$ complexity) libraries of infectious molecules from shuffled fragments of HIV-1 are established. Third, libraries of HIV-1 recombinants are produced using in vivo recombination pathways. Fourth, synthetic HIV-1 tat genes representing all clades are bred into infectious virus and make large libraries of infectious molecular clones, based on the techniques established in the first and second step. Fifth, CD4+ CCR5+ mouse cells are infected with these libraries and selected for mutants which can replicate and be passaged in tissue culture. Eight consensus tat genes representing all eight HIV-1 clades were synthesized. Sixth, mouse and human reporter cells containing constructs with GFP under the control of an HIV-1 LTR were constructed. Seventh, the transcriptional activation activities of the synthetic tat genes in the reporter cells are validated. Ninth, libraries of shuffled tat genes are constructed in an MLV retroviral vector and introduce them into the reporter cells. Tenth, methods to FACS select libraries for cells with tat induced GFP are established, and the tat genes recovered by PCR, shuffled, and reconstruct new libraries of shuffled genes. Eleventh, evolved tat genes are bred into the context of infectious molecular clones and select for growth on mouse cells. For Macaques, an immortalized macaque cell line is constructed expressing macaque CD4 and CCR5, which are known to support efficient entry of HIV into macaque cells. This cell line is used to select in tissue culture for replication of HIV in macaque cells.

Infectious HIV-1 libraries carrying shuffled gag-proteinase coding sequences were generated. 2.5 kb fragments encoding gag-proteinase coding region were amplified from four clade B isolates and four clade D isolates. After DNaseI digestion, 500–1000 bp and 1000–1500 bp fragments were purified by agarose gel electrophoresis. Assembly reaction was performed using clade B fragments only, clade D fragments only, or a mixture of clade B and D. Because all three reactions yielded similar amounts of assembled products, clade B/D assembled products were used to maximized diversity of libraries. The number of the assembled molecules in the assembly reaction was estimated by semi-quantitative PCR. Serial 10-fold dilutions of the assembled products (from 500–1000 bp and 1000–1500 bp fragments, indicated as S and L, respectively) and the standard (plasmid carrying proviral DNA) were made and amplified by PCR. Approximately $10^{12}$ molecules were detected in both assembly reactions. The one assembled from the smaller (500–1000 bp) fragments was used to maximize the frequency of recombination.

If one can assume all chimeric molecules generated by the above shuffling experiment are different, the maximum library generated from this assembled product is $10^{12}$. However, there is no advantage to make libraries larger than the screening capacity.

The library for is screened for replication in target cells by: Transfection of the library into human 293 cells, Coculture transfected cells with the target cells (monkey lymphocytes), Separate target cells from 293 cells, culture for 2 weeks, and passage the replicating virus. Because the amount of DNA used for transfection is limited (typically 30 $\mu$g), the minimum amount of DNA required for producing one infectious virus determines the appropriate library size that can be analyzed in one transfection/infection. To determine the minimum infectious DNA dose, serial 10-fold dilution of the wild type HIV-1 DNA was used for transfection of human 293 cells in quintuplicate. Transfected cells were cocultured with human lymphoid cell line MT-4, to amplify infectious virus produced from transfected cells. Cultures were kept for 3 weeks to detect the end-point of infectivity. Approximately 10 ng DNA was required to produce one infectious virus. Therefore, libraries containing 3000 clones (30 $\mu$g divided by 10 ng) are adequate.

Based on this result, we decided to generate multiple sublibraries from the same assembly reaction. We made multiple aliquots from the assembly reaction, each of them containing $10^9$ molecules. Presumably, all chimeric molecules from aliquot#1 should be different from any chimeric molecule in aliquot #2 (no redundancy). Each aliquot was amplified by PCR and cloned into the full-length HIV. Because cloning efficiency is not high, sizes of sublibraries are not $10^9$, but range from 5,000 to 100,000. These are large enough because there is no advantage to make libraries larger than 3,000 (see the previous paragraph).

We next examined viability and diversity of one of the sublibraries. Six out of 40 randomly chosen clones were able to replicate in human MT-4 cells. When these clones were analyzed by Dra1 digestion, 13 clones exhibited patterns different from any one of the parental clones. Because Dra1 restriction digestion does not distinguish all parental clones (e.g. ELI, UG15, and Z2Z6 have the same restriction pattern therefore these three and chimeras between them are indistinguishable), recombination rate of 13/40 is very likely to be underestimation. This library has enough viability and diversity for screening.

Modifications can be made to the methods and compositions as herein before described without departing from the spirit or scope of the invention as claimed, and the invention can be put to a number of different uses. Assays kits or systems providing a use of any one of the components, methods or substrates herein before described are also provided. Kits will optionally additionally comprise instructions for performing assays or using the methods or compositions herein, packaging materials, one or more containers which contain compositions, system components, or the like. In a further aspect, the present invention provides for the use of any method, composition or kit herein, for the practice of any method or assay herein, and/or for the use of any composition, method or kit to practice any assay or method herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes, as if each reference were specifically indicated to be incorporated by reference.

What is claimed is:

1. A method for generating a viral polynucleotide sequence having a genotype encoding at least one modified viral phenotype, the method comprising:

contacting a cell or non-human animal which does not naturally support substantial replication of a predetermined virus, with at least one initial infectious virion or replicable genome of said predetermined virus under replication conditions;

recovering a plurality of replicated genome copies of said predetermined virus, either as virions or as viral genomes in polynucleotide form, wherein some or all of the replicated genome copies comprise a mutation relative to the at least one initial infectious virion or replicable genome;

recombining a plurality of said replicated genome copies, so as to shuffle the mutations, thereby generating a collection of recombined replicated genome copies; and selecting or screening said collection of recombined replicated genome copies for at least one recombined replicable viral genome encoding at least one modified viral phenotype.

2. The method of claim 1, wherein the at least one modified viral phenotype is a host range or cell tropism phenotype.

3. The method of claim 2, wherein the host range or cell tropism phenotype is the ability to replicate in mouse or macaque monkey cells.

4. The method of claim 2, wherein the host range or cell tropism phenotype is the ability to replicate in a transgenic mouse expressing a human CD4 protein or HIV co-receptor on lymphocytes.

5. The method of claim 1, wherein the predetermined virus is selected from HIV-1, HIV-2, HCV, HBV, MLV and SIV.

6. The method of claim 5, wherein the virus is an HIV-1 which HIV-1 is a clinical isolate which has been passaged in cell culture for less than 10 passages.

7. The method of claim 1, wherein the at least one modified viral phenotype is an ability to replicate in a transgenic non-human animal expressing human CD4 and human CCR5.

8. The method of claim 7, wherein the transgenic non-human animal also expresses human CXCR4.

9. The method of claim 1, comprising the further step of recombining a plurality of species of viral genomes of said predetermined virus, so as to shuffle the viral genome sequences, thereby generating a collection of recombined replicated genome copies, wherein the further recombining step is conducted prior to contacting the viral genome of at least one of said collection of recombined replicated genome copies with the cell or non-human animal which does not naturally support substantial replication of said predetermined virus.

10. The method of claim 1, which further comprises an iterative cycle of at least one iteration of the contacting, recovering, and recombining steps prior to the selecting or screening step.

11. The method of claim 9, wherein the steps of shuffling and selection or screening are iteratively repeated at least twice.

12. The method of claim 2, wherein the host range or cell tropism phenotype is the ability to replicate in primate cells.

13. The method of claim 1, wherein the predetermined virus is selected from the group of retrovirus, adenovirus, adeno-associated virus, herpesvirus, and lentivirus.

14. The method of claim 1, which further comprises an iterative recycle of at least one iteration of the recombining and selecting or screening steps.

15. The method of claim 1, wherein the at least one modified viral phenotype comprises modified immunogenicity.

16. The method of claim 1, wherein the at least one modified viral phenotype comprises modified drug resistance.

* * * * *